US012006525B2

(12) United States Patent
Pigeon et al.

(10) Patent No.: US 12,006,525 B2
(45) Date of Patent: Jun. 11, 2024

(54) PRODUCTION OF RNA BY YEASTS WITH RECOMBINANT PSEUDO-VIRAL PARTICLES

(71) Applicants: CENTRE NATIONAL DE LA RECHERCHE SCIENTIFIQUE, Paris (FR); UNIVERSITE D'ORLEANS, Orleans (FR)

(72) Inventors: Lucie Pigeon, Olivet (FR); Rachid A. Rahmouni, Germigny des Pre (FR); Harivony Chantal Pichon-Rabenandrasana, St Denis de L'Hôtel (FR); Patrick Midoux, Saint Denis de L'Hôtel (FR)

(73) Assignees: CENTRE NATIONAL DE LA RECHERCHE SCIENTIFIQUE, Paris (FR); UNIVERSITE D'ORLEANS, Orleans (FR)

( * ) Notice: Subject to any disclaimer, the term of this patent is extended or adjusted under 35 U.S.C. 154(b) by 1065 days.

(21) Appl. No.: 16/495,874

(22) PCT Filed: Mar. 21, 2018

(86) PCT No.: PCT/EP2018/025066

§ 371 (c)(1),
(2) Date: Sep. 20, 2019

(87) PCT Pub. No.: WO2018/171946

PCT Pub. Date: Sep. 27, 2018

(65) Prior Publication Data

US 2020/0010866 A1 Jan. 9, 2020

(30) Foreign Application Priority Data

Mar. 21, 2017 (FR) ..................................... 17/52309

(51) Int. Cl.

*C12P 19/34* (2006.01)
*A61K 31/7088* (2006.01)
*C07K 14/395* (2006.01)
*C12N 15/81* (2006.01)

(52) U.S. Cl.

CPC .......... *C12P 19/34* (2013.01); *A61K 31/7088* (2013.01); *C07K 14/395* (2013.01); *C12N 15/81* (2013.01)

(58) Field of Classification Search

CPC ... C12P 19/34; A61K 31/7088; C07K 14/395; C12N 15/81

See application file for complete search history.

(56) References Cited

U.S. PATENT DOCUMENTS

2015/0329858 A1 11/2015 Aburatani et al.

FOREIGN PATENT DOCUMENTS

| | | | |
|---|---|---|---|
| EP | 2377938 | A1 | 10/2011 |
| WO | 2004108943 | A1 | 12/2004 |
| WO | 2007072056 | A2 | 6/2007 |
| WO | 2010084371 | A1 | 7/2010 |
| WO | 2011128444 | A2 | 10/2011 |
| WO | 2016185125 | A1 | 11/2016 |
| WO | 2014077354 | A1 | 1/2017 |

OTHER PUBLICATIONS

Krastanova et al., Ty Elements of the Yeast *Saccharomyces cerevisiae*, Biotechnol. & Biotechnol. Eq. 19/2005/3, p. 19-26, Publication Date:Apr. 15, 2014. (Year: 2014).*

Bowie et al., Deciphering the Message in Protein Sequences: Tolerance to Amino Acid Substitutions, Science, 1990, 247:1306-1310. (Year: 1990).*

Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*

Lazar et al., Transforming Growth Factor ox: Mutation of Aspartic Acid 47 and Leucine 48 Results in Different Biological Activities, Mol. Cell. Biol., 8:1247-1252. (Year: 1988).*

Boeke et al., Yeast Retrotransposons: Finding a Nice Quiet Neighborhood, Cell, vol. 93, 1087-1089, Publication Date: Jun. 26, 1998 (Year: 1998).*

Written Opinion of the International Searching Authority (PCT/ISA/237) issued in PCT/EP2018/025066, dated Jun. 4, 2018.

Mével et al., "Synthesis and Transfection Activity of New Cationic Phosphoramidate Lipids: High Efficiency of an Imidazolium Derivative", ChemBioChem, vol. 9, 2008, pp. 1462-1471.

Mével et al., "Novel neutral imidazole-lipophosphoramides for transfection assays", Chemical Communications, 2008, pp. 3124-3126.

(Continued)

*Primary Examiner* — Peter J Reddig
*Assistant Examiner* — Cheng Lu
(74) *Attorney, Agent, or Firm* — NIXON & VANDERHYE

(57) ABSTRACT

The application relates to the production of RNA of interest, more specifically of messenger RNA of interest or of long non-coding RNA of interest, by yeasts with recombinant pseudo-viral particles. The recombinant yeasts have been genetically modified in order to produce the RNA of interest in the form of a complex, particularly in the form of recombinant pseudo-viral particles. These recombinant pseudo-viral particles are produced from certain elements of yeast Ty retrotransposon, but do not retrotranscribe the RNA that they contain. Thus, the application relates to the components that are thus capable of being implemented or produced, and particularly to the nucleic acid constructs, kits, bacteria cells, yeast cells, culture or transfection media containing them, as well as to a method for producing a pharmaceutical composition, particularly for medical applications, more specifically for vaccines, anti-tumour and pro-regenerative applications.

9 Claims, 8 Drawing Sheets

Specification includes a Sequence Listing.

(56) References Cited

OTHER PUBLICATIONS

Perche et al., "Enhancement of dendritic cells transfection in vivo and of vaccination against B16F10 melanoma with mannosylated histidylated lipopolyplexes loaded with tumor antigen messenger RNA", Nanomedicine: Nanotechnology, Biology, and Medicine, vol. 7, 2011, pp. 445-453.
Perche et al., "Selective gene delivery in dendritic cells with mannosylated and histidylated lipopolyplexes", Journal of Drug Targeting, vol. 19, No. 5, 2011, pp. 315-325.
Rothstein, "One-Step Gene Disruption in Yeast", Methods in Enzymology, vol. 101, 1983, pp. 202-211.
Thomas et al., "Elevated Recombination Rates in Transcriptionally Active DNA", Cell, vol. 56, Feb. 24, 1989, pp. 619-630.
International Search Report, dated Jun. 4, 2018, from corresponding PCT application No. PCT/EP2018/025066.
Pachulska-Wieczorek et al.; Determinants of Genomic RNA encapsidation in the *Saccharomyces cerevisiae* Long Terminal Repeat Retrotransposons Tyl and Ty3; Viruses; Jul. 14, 2019; vol. 8, No. 7.
Cristofari et al.; A 5'-3' long-range interaction in Ty1 RNA controls its reverse transcription and retrotransposition; The EMBO Journal; Aug. 15, 2002; pp. 4368-4379; vol. 21.
Checkley et al.; Ty1 Gag Enhances the Stability and Nuclear Export of Ty1 mRNA; Traffic; Oct. 17, 2012; pp. 57-69; vol. 14, No. 1.
Derrien et al.; The Gencode v7 catalog of human long noncoding RNAs: Analysis of their gene structure, evolution, and expression; Genome Research; Sep. 1, 2012; pp. 1775-1789; vol. 22, No. 9.
Prel et al.; Highly efficient in vitro and in vivo delivery of functional RNAs using new versatile MS2-chimeric retrovirus-like particles; Molecular Theraphy—Methods & Clinical Development; Oct. 21, 2015; pp. 15039; vol. 2.
Liz et al.; IncRNAs and microRNAs with a role in cancer development; Biochimica et Biophysica Acta—Gene Regulatory Mechanisms; Jul. 4, 2015; pp. 169-176; vol. 1859, No. 1; Elsevier; Amsterdam, Netherlands.
Gutschner et al.; The hallmarks of cancer: a long non-coding RNA point of view; RNA Biology; Jun. 1, 2012; pp. 703-719; vol. 9, No. 6.

* cited by examiner

SEQUENCE LISTING

```
<160> NUMBER OF SEQ ID NOS: 45

<210> SEQ ID NO 1
<211> LENGTH: 1356
<212> TYPE: DNA
<213> ORGANISM: Saccharomyces cerevisiae

<400> SEQUENCE: 1

tgatagatct gactagtatg gaatcccaac aattatctaa ttacccacat atatctcatg      60

gtagcgcctg tgcttcggtt acttctaagg aagtccacac aaatcaagat ccgttagacg     120

tttcagcttc caaaattcaa gaatatgata aggcttccac taaggctaac tctcaacaga     180

caacaacacc tgcttcatca gctgttccag agaacccca tcatgcctct cctcaacctg     240

cttcagtacc acctccacag aatgggccgt acccacagca gtgcatgatg acccaaaacc     300

aagccaatcc atctggttgg tcattttacg gacacccatc tatgattccg tatacacctt     360

atcaaatgtc gcctatgtac tttccacctg ggccacaatc acagtttccg cagtatccat     420

catcagttgg aacgcctctg agcactccat cacctgagtc aggtaataca tttactgatt     480

catcctcagc ggactctgat atgacatcca ctaaaaaata tgtcagacca ccaccaatgt     540
```

```
taacctcacc taatgacttt ccaaattggg ttaaaacata catcaaattt ttacaaaact    600

cgaatctcgg tggtattatt ccgacagtaa acggaaaacc cgtacgtccg atcactgatg    660

atgaactcac cttcttgtat aacgcttttc aaatatttgc tccctctcaa ttcctaccta    720

cctgggtcaa agacatccta tccgttgatt atacggatat catgaaaatt ctttccaaaa    780

gtattgaaaa aatgcaatct gatacccaag aggcaaacga cattgtgacc ctggcaaatt    840

tgcaatataa tggcagtaca cctgcagatg catttgaaac aaaagtcaca aacattatcg    900

acagactgaa caataatggc attcatatca ataacaaggt cgcatgtcaa ttaattatga    960

gaggtctatc tggcgaatat aaatttttac gctacacacg tcatcgacat ctaaatatga   1020

cagtcgctga actgttctta gatatccatg ctatttatga agaacaacag ggatcgagaa   1080

acagcaaacc taattacagg agaaatccga gtgatgagaa gaatgattct cgcagctata   1140

cgaatacaac caaacccaaa gttatagctc ggaatcctca aaaaacaaat aattcgaaat   1200

cgaaaacagc cagggctcac aatgtatcca catctaataa ctctcccagc acggacaacg   1260

attccatcag taaatcaact actgaaccga ttcaattgaa caataagcac gaccttcatc   1320

ttaggccaga aacttactga gtcgacggta cctgat                              1356
```

<210> SEQ ID NO 2
<211> LENGTH: 1323
<212> TYPE: DNA
<213> ORGANISM: Saccharomyces cerevisiae

<400> SEQUENCE: 2

```
atggaatccc aacaattatc taattaccca catatatctc atggtagcgc ctgtgcttcg     60

gttacttcta aggaagtcca cacaaatcaa gatccgttag acgtttcagc ttccaaaatt    120

caagaatatg ataaggcttc cactaaggct aactctcaac agacaacaac acctgcttca    180

tcagctgttc cagagaaccc ccatcatgcc tctcctcaac ctgcttcagt accacctcca    240

cagaatgggc cgtacccaca gcagtgcatg atgacccaaa accaagccaa tccatctggt    300

tggtcatttt acggacaccc atctatgatt ccgtatacac cttatcaaat gtcgcctatg    360

tactttccac ctgggccaca atcacagttt ccgcagtatc catcatcagt tggaacgcct    420

ctgagcactc catcacctga gtcaggtaat acatttactg attcatcctc agcggactct    480

gatatgacat ccactaaaaa atatgtcaga ccaccaccaa tgttaacctc acctaatgac    540

tttccaaatt gggttaaaac atacatcaaa tttttacaaa actcgaatct cggtggtatt    600

attccgacag taaacggaaa acccgtacgt ccgatcactg atgatgaact caccttcttg    660

tataacgctt ttcaaatatt tgctccctct caattcctac ctacctgggt caaagacatc    720

ctatccgttg attatacgga tatcatgaaa attctttcca aaagtattga aaaaatgcaa    780

tctgataccc aagaggcaaa cgacattgtg accctggcaa atttgcaata taatggcagt    840

acacctgcag atgcatttga aacaaaagtc acaaacatta tcgacagact gaacaataat    900

ggcattcata tcaataacaa ggtcgcatgt caattaatta tgagaggtct atctggcgaa    960

tataaatttt tacgctacac acgtcatcga catctaaata tgacagtcgc tgaactgttc   1020

ttagatatcc atgctattta tgaagaacaa cagggatcga gaaacagcaa acctaattac   1080

aggagaaatc cgagtgatga gaagaatgat tctcgcagct atacgaatac aaccaaaccc   1140

aaagttatag ctcggaatcc tcaaaaaaca aataattcga aatcgaaaac agccagggct   1200

cacaatgtat ccacatctaa taactctccc agcacggaca acgattccat cagtaaatca   1260

actactgaac cgattcaatt gaacaataag cacgaccttc atcttaggcc agaaacttac   1320
```

tga 1323

<210> SEQ ID NO 3
<211> LENGTH: 440
<212> TYPE: PRT
<213> ORGANISM: Saccharomyces cerevisiae

<400> SEQUENCE: 3

```
Met Glu Ser Gln Gln Leu Ser Asn Tyr Pro His Ile Ser His Gly Ser
1               5                   10                  15

Ala Cys Ala Ser Val Thr Ser Lys Glu Val His Thr Asn Gln Asp Pro
            20                  25                  30

Leu Asp Val Ser Ala Ser Lys Ile Gln Glu Tyr Asp Lys Ala Ser Thr
        35                  40                  45

Lys Ala Asn Ser Gln Gln Thr Thr Thr Pro Ala Ser Ser Ala Val Pro
    50                  55                  60

Glu Asn Pro His His Ala Ser Pro Gln Pro Ala Ser Val Pro Pro Pro
65                  70                  75                  80

Gln Asn Gly Pro Tyr Pro Gln Gln Cys Met Met Thr Gln Asn Gln Ala
                85                  90                  95

Asn Pro Ser Gly Trp Ser Phe Tyr Gly His Pro Ser Met Ile Pro Tyr
            100                 105                 110

Thr Pro Tyr Gln Met Ser Pro Met Tyr Phe Pro Pro Gly Pro Gln Ser
        115                 120                 125

Gln Phe Pro Gln Tyr Pro Ser Ser Val Gly Thr Pro Leu Ser Thr Pro
    130                 135                 140

Ser Pro Glu Ser Gly Asn Thr Phe Thr Asp Ser Ser Ser Ala Asp Ser
145                 150                 155                 160

Asp Met Thr Ser Thr Lys Lys Tyr Val Arg Pro Pro Pro Met Leu Thr
                165                 170                 175

Ser Pro Asn Asp Phe Pro Asn Trp Val Lys Thr Tyr Ile Lys Phe Leu
            180                 185                 190

Gln Asn Ser Asn Leu Gly Gly Ile Ile Pro Thr Val Asn Gly Lys Pro
        195                 200                 205

Val Arg Pro Ile Thr Asp Asp Glu Leu Thr Phe Leu Tyr Asn Ala Phe
    210                 215                 220

Gln Ile Phe Ala Pro Ser Gln Phe Leu Pro Thr Trp Val Lys Asp Ile
225                 230                 235                 240

Leu Ser Val Asp Tyr Thr Asp Ile Met Lys Ile Leu Ser Lys Ser Ile
                245                 250                 255

Glu Lys Met Gln Ser Asp Thr Gln Glu Ala Asn Asp Ile Val Thr Leu
            260                 265                 270

Ala Asn Leu Gln Tyr Asn Gly Ser Thr Pro Ala Asp Ala Phe Glu Thr
        275                 280                 285

Lys Val Thr Asn Ile Ile Asp Arg Leu Asn Asn Asn Gly Ile His Ile
    290                 295                 300

Asn Asn Lys Val Ala Cys Gln Leu Ile Met Arg Gly Leu Ser Gly Glu
305                 310                 315                 320

Tyr Lys Phe Leu Arg Tyr Thr Arg His Arg His Leu Asn Met Thr Val
                325                 330                 335

Ala Glu Leu Phe Leu Asp Ile His Ala Ile Tyr Glu Glu Gln Gln Gly
            340                 345                 350

Ser Arg Asn Ser Lys Pro Asn Tyr Arg Arg Asn Pro Ser Asp Glu Lys
        355                 360                 365
```

```
Asn Asp Ser Arg Ser Tyr Thr Asn Thr Thr Lys Pro Lys Val Ile Ala
    370                 375                 380

Arg Asn Pro Gln Lys Thr Asn Asn Ser Lys Ser Lys Thr Ala Arg Ala
385                 390                 395                 400

His Asn Val Ser Thr Ser Asn Asn Ser Pro Ser Thr Asp Asn Asp Ser
                405                 410                 415

Ile Ser Lys Ser Thr Thr Glu Pro Ile Gln Leu Asn Asn Lys His Asp
            420                 425                 430

Leu His Leu Arg Pro Glu Thr Tyr
        435                 440


<210> SEQ ID NO 4
<211> LENGTH: 18
<212> TYPE: DNA
<213> ORGANISM: Artificial sequence
<220> FEATURE:
<223> OTHER INFORMATION: tag 6His

<400> SEQUENCE: 4

caccaccacc accaccac                                                18


<210> SEQ ID NO 5
<211> LENGTH: 18
<212> TYPE: RNA
<213> ORGANISM: Artificial sequence
<220> FEATURE:
<223> OTHER INFORMATION: tag 6His

<400> SEQUENCE: 5

caccaccacc accaccac                                                18


<210> SEQ ID NO 6
<211> LENGTH: 6
<212> TYPE: PRT
<213> ORGANISM: Artificial sequence
<220> FEATURE:
<223> OTHER INFORMATION: tag 6His

<400> SEQUENCE: 6

His His His His His His
1               5


<210> SEQ ID NO 7
<211> LENGTH: 1359
<212> TYPE: DNA
<213> ORGANISM: Artificial sequence
<220> FEATURE:
<223> OTHER INFORMATION: 6His-Gag of Ty1

<400> SEQUENCE: 7

atgcaccacc accaccacca cggcagcggc agcggcatgg aatcccaaca attatctaat     60

tacccacata tatctcatgg tagcgcctgt gcttcggtta cttctaagga agtccacaca    120

aatcaagatc cgttagacgt ttcagcttcc aaaattcaag aatatgataa ggcttccact    180

aaggctaact ctcaacagac aacaacacct gcttcatcag ctgttccaga gaaccccat    240

catgcctctc ctcaacctgc ttcagtacca cctccacaga atgggccgta cccacagcag    300

tgcatgatga cccaaaacca agccaatcca tctggttggt cattttacgg acacccatct    360

atgattccgt atacacctta tcaaatgtcg cctatgtact ttccacctgg gccacaatca    420

cagtttccgc agtatccatc atcagttgga acgcctctga gcactccatc acctgagtca    480
```

```
ggtaatacat ttactgattc atcctcagcg gactctgata tgacatccac taaaaaatat    540

gtcagaccac caccaatgtt aacctcacct aatgactttc caaattgggt taaaacatac    600

atcaaatttt tacaaaactc gaatctcggt ggtattattc cgacagtaaa cggaaaaccc    660

gtacgtccga tcactgatga tgaactcacc ttcttgtata acgcttttca aatatttgct    720

ccctctcaat tcctacctac ctgggtcaaa gacatcctat ccgttgatta tacggatatc    780

atgaaaattc tttccaaaag tattgaaaaa atgcaatctg atacccaaga ggcaaacgac    840

attgtgaccc tggcaaattt gcaatataat ggcagtacac ctgcagatgc atttgaaaca    900

aaagtcacaa acattatcga cagactgaac aataatggca ttcatatcaa taacaaggtc    960

gcatgtcaat taattatgag aggtctatct ggcgaatata aatttttacg ctacacacgt   1020

catcgacatc taaatatgac agtcgctgaa ctgttcttag atatccatgc tatttatgaa   1080

gaacaacagg gatcgagaaa cagcaaacct aattacagga gaaatccgag tgatgagaag   1140

aatgattctc gcagctatac gaatacaacc aaacccaaag ttatagctcg gaatcctcaa   1200

aaaacaaata attcgaaatc gaaaacagcc agggctcaca atgtatccac atctaataac   1260

tctcccagca cggacaacga ttccatcagt aaatcaacta ctgaaccgat tcaattgaac   1320

aataagcacg accttcatct taggccagaa acttactga                          1359
```

```
<210> SEQ ID NO 8
<211> LENGTH: 452
<212> TYPE: PRT
<213> ORGANISM: Artificial sequence
<220> FEATURE:
<223> OTHER INFORMATION: 6His-Gag of Ty1

<400> SEQUENCE: 8

Met His His His His His His Gly Ser Gly Ser Gly Met Glu Ser Gln
1               5                   10                  15

Gln Leu Ser Asn Tyr Pro His Ile Ser His Gly Ser Ala Cys Ala Ser
            20                  25                  30

Val Thr Ser Lys Glu Val His Thr Asn Gln Asp Pro Leu Asp Val Ser
        35                  40                  45

Ala Ser Lys Ile Gln Glu Tyr Asp Lys Ala Ser Thr Lys Ala Asn Ser
    50                  55                  60

Gln Gln Thr Thr Thr Pro Ala Ser Ser Ala Val Pro Glu Asn Pro His
65                  70                  75                  80

His Ala Ser Pro Gln Pro Ala Ser Val Pro Pro Pro Gln Asn Gly Pro
                85                  90                  95

Tyr Pro Gln Gln Cys Met Met Thr Gln Asn Gln Ala Asn Pro Ser Gly
            100                 105                 110

Trp Ser Phe Tyr Gly His Pro Ser Met Ile Pro Tyr Thr Pro Tyr Gln
        115                 120                 125

Met Ser Pro Met Tyr Phe Pro Pro Gly Pro Gln Ser Gln Phe Pro Gln
    130                 135                 140

Tyr Pro Ser Ser Val Gly Thr Pro Leu Ser Thr Pro Ser Pro Glu Ser
145                 150                 155                 160

Gly Asn Thr Phe Thr Asp Ser Ser Ser Ala Asp Ser Asp Met Thr Ser
                165                 170                 175

Thr Lys Lys Tyr Val Arg Pro Pro Pro Met Leu Thr Ser Pro Asn Asp
            180                 185                 190

Phe Pro Asn Trp Val Lys Thr Tyr Ile Lys Phe Leu Gln Asn Ser Asn
        195                 200                 205
```

```
Leu Gly Gly Ile Ile Pro Thr Val Asn Gly Lys Pro Val Arg Pro Ile
    210                 215                 220

Thr Asp Asp Glu Leu Thr Phe Leu Tyr Asn Ala Phe Gln Ile Phe Ala
225                 230                 235                 240

Pro Ser Gln Phe Leu Pro Thr Trp Val Lys Asp Ile Leu Ser Val Asp
                245                 250                 255

Tyr Thr Asp Ile Met Lys Ile Leu Ser Lys Ser Ile Glu Lys Met Gln
            260                 265                 270

Ser Asp Thr Gln Glu Ala Asn Asp Ile Val Thr Leu Ala Asn Leu Gln
        275                 280                 285

Tyr Asn Gly Ser Thr Pro Ala Asp Ala Phe Glu Thr Lys Val Thr Asn
    290                 295                 300

Ile Ile Asp Arg Leu Asn Asn Asn Gly Ile His Ile Asn Asn Lys Val
305                 310                 315                 320

Ala Cys Gln Leu Ile Met Arg Gly Leu Ser Gly Glu Tyr Lys Phe Leu
                325                 330                 335

Arg Tyr Thr Arg His Arg His Leu Asn Met Thr Val Ala Glu Leu Phe
            340                 345                 350

Leu Asp Ile His Ala Ile Tyr Glu Glu Gln Gln Gly Ser Arg Asn Ser
        355                 360                 365

Lys Pro Asn Tyr Arg Arg Asn Pro Ser Asp Glu Lys Asn Asp Ser Arg
    370                 375                 380

Ser Tyr Thr Asn Thr Thr Lys Pro Lys Val Ile Ala Arg Asn Pro Gln
385                 390                 395                 400

Lys Thr Asn Asn Ser Lys Ser Lys Thr Ala Arg Ala His Asn Val Ser
                405                 410                 415

Thr Ser Asn Asn Ser Pro Ser Thr Asp Asn Asp Ser Ile Ser Lys Ser
            420                 425                 430

Thr Thr Glu Pro Ile Gln Leu Asn Asn Lys His Asp Leu His Leu Arg
        435                 440                 445

Pro Glu Thr Tyr
    450
```

<210> SEQ ID NO 9
<211> LENGTH: 1356
<212> TYPE: DNA
<213> ORGANISM: Artificial sequence
<220> FEATURE:
<223> OTHER INFORMATION: Gag of Ty1 - 6His

<400> SEQUENCE: 9

```
atggaatccc aacaattatc taattaccca catatatctc atggtagcgc ctgtgcttcg      60

gttacttcta aggaagtcca cacaaatcaa gatccgttag acgtttcagc ttccaaaatt     120

caagaatatg ataaggcttc cactaaggct aactctcaac agacaacaac acctgcttca     180

tcagctgttc cagagaaccc ccatcatgcc tctcctcaac ctgcttcagt accacctcca     240

cagaatgggc cgtacccaca gcagtgcatg atgacccaaa accaagccaa tccatctggt     300

tggtcatttt acggacaccc atctatgatt ccgtatacac cttatcaaat gtcgcctatg     360

tactttccac ctgggccaca atcacagttt ccgcagtatc catcatcagt tggaacgcct     420

ctgagcactc catcacctga gtcaggtaat acatttactg attcatcctc agcggactct     480

gatatgacat ccactaaaaa atatgtcaga ccaccaccaa tgttaacctc acctaatgac     540

tttccaaatt gggttaaaac atacatcaaa tttttacaaa actcgaatct cggtggtatt     600

attccgacag taaacggaaa acccgtacgt ccgatcactg atgatgaact caccttcttg     660
```

```
tataacgctt ttcaaatatt tgctccctct caattcctac ctacctgggt caaagacatc    720

ctatccgttg attatacgga tatcatgaaa attctttcca aaagtattga aaaaatgcaa    780

tctgataccc aagaggcaaa cgacattgtg accctggcaa atttgcaata taatggcagt    840

acacctgcag atgcatttga aacaaaagtc acaaacatta tcgacagact gaacaataat    900

ggcattcata tcaataacaa ggtcgcatgt caattaatta tgagaggtct atctggcgaa    960

tataaatttt tacgctacac acgtcatcga catctaaata tgacagtcgc tgaactgttc   1020

ttagatatcc atgctattta tgaagaacaa cagggatcga gaaacagcaa acctaattac   1080

aggagaaatc cgagtgatga gaagaatgat tctcgcagct atacgaatac aaccaaaccc   1140

aaagttatag ctcggaatcc tcaaaaaaca aataattcga aatcgaaaac agccagggct   1200

cacaatgtat ccacatctaa taactctccc agcacggaca acgattccat cagtaaatca   1260

actactgaac cgattcaatt gaacaataag cacgaccttc atcttaggcc agaaacttac   1320

ggcagcggca gcggccacca ccaccaccac cactga                             1356
```

```
<210> SEQ ID NO 10
<211> LENGTH: 451
<212> TYPE: PRT
<213> ORGANISM: Artificial sequence
<220> FEATURE:
<223> OTHER INFORMATION: Gag of Ty1 - 6His

<400> SEQUENCE: 10

Met Glu Ser Gln Gln Leu Ser Asn Tyr Pro His Ile Ser His Gly Ser
1               5                   10                  15

Ala Cys Ala Ser Val Thr Ser Lys Glu Val His Thr Asn Gln Asp Pro
            20                  25                  30

Leu Asp Val Ser Ala Ser Lys Ile Gln Glu Tyr Asp Lys Ala Ser Thr
        35                  40                  45

Lys Ala Asn Ser Gln Gln Thr Thr Thr Pro Ala Ser Ser Ala Val Pro
    50                  55                  60

Glu Asn Pro His His Ala Ser Pro Gln Pro Ala Ser Val Pro Pro Pro
65                  70                  75                  80

Gln Asn Gly Pro Tyr Pro Gln Gln Cys Met Met Thr Gln Asn Gln Ala
                85                  90                  95

Asn Pro Ser Gly Trp Ser Phe Tyr Gly His Pro Ser Met Ile Pro Tyr
            100                 105                 110

Thr Pro Tyr Gln Met Ser Pro Met Tyr Phe Pro Pro Gly Pro Gln Ser
        115                 120                 125

Gln Phe Pro Gln Tyr Pro Ser Ser Val Gly Thr Pro Leu Ser Thr Pro
    130                 135                 140

Ser Pro Glu Ser Gly Asn Thr Phe Thr Asp Ser Ser Ser Ala Asp Ser
145                 150                 155                 160

Asp Met Thr Ser Thr Lys Lys Tyr Val Arg Pro Pro Pro Met Leu Thr
                165                 170                 175

Ser Pro Asn Asp Phe Pro Asn Trp Val Lys Thr Tyr Ile Lys Phe Leu
            180                 185                 190

Gln Asn Ser Asn Leu Gly Gly Ile Ile Pro Thr Val Asn Gly Lys Pro
        195                 200                 205

Val Arg Pro Ile Thr Asp Asp Glu Leu Thr Phe Leu Tyr Asn Ala Phe
    210                 215                 220

Gln Ile Phe Ala Pro Ser Gln Phe Leu Pro Thr Trp Val Lys Asp Ile
225                 230                 235                 240
```

```
Leu Ser Val Asp Tyr Thr Asp Ile Met Lys Ile Leu Ser Lys Ser Ile
                245                 250                 255

Glu Lys Met Gln Ser Asp Thr Gln Glu Ala Asn Asp Ile Val Thr Leu
            260                 265                 270

Ala Asn Leu Gln Tyr Asn Gly Ser Thr Pro Ala Asp Ala Phe Glu Thr
        275                 280                 285

Lys Val Thr Asn Ile Ile Asp Arg Leu Asn Asn Asn Gly Ile His Ile
    290                 295                 300

Asn Asn Lys Val Ala Cys Gln Leu Ile Met Arg Gly Leu Ser Gly Glu
305                 310                 315                 320

Tyr Lys Phe Leu Arg Tyr Thr Arg His Arg His Leu Asn Met Thr Val
                325                 330                 335

Ala Glu Leu Phe Leu Asp Ile His Ala Ile Tyr Glu Glu Gln Gln Gly
            340                 345                 350

Ser Arg Asn Ser Lys Pro Asn Tyr Arg Arg Asn Pro Ser Asp Glu Lys
        355                 360                 365

Asn Asp Ser Arg Ser Tyr Thr Asn Thr Thr Lys Pro Lys Val Ile Ala
    370                 375                 380

Arg Asn Pro Gln Lys Thr Asn Asn Ser Lys Ser Lys Thr Ala Arg Ala
385                 390                 395                 400

His Asn Val Ser Thr Ser Asn Asn Ser Pro Ser Thr Asp Asn Asp Ser
                405                 410                 415

Ile Ser Lys Ser Thr Thr Glu Pro Ile Gln Leu Asn Asn Lys His Asp
            420                 425                 430

Leu His Leu Arg Pro Glu Thr Tyr Gly Ser Gly Ser Gly His His His
        435                 440                 445

His His His
    450
```

```
<210> SEQ ID NO 11
<211> LENGTH: 1392
<212> TYPE: DNA
<213> ORGANISM: Artificial sequence
<220> FEATURE:
<223> OTHER INFORMATION: 6His-Gag of Ty1-6His

<400> SEQUENCE: 11

atgcaccacc accaccacca cggcagcggc agcggcatgg aatcccaaca attatctaat      60

tacccacata tatctcatgg tagcgcctgt gcttcggtta cttctaagga agtccacaca     120

aatcaagatc cgttagacgt ttcagcttcc aaaattcaag aatatgataa ggcttccact     180

aaggctaact ctcaacagac aacaacacct gcttcatcag ctgttccaga gaacccccat     240

catgcctctc ctcaacctgc ttcagtacca cctccacaga atgggccgta cccacagcag     300

tgcatgatga cccaaaacca agccaatcca tctggttggt cattttacgg acacccatct     360

atgattccgt atacacctta tcaaatgtcg cctatgtact ttccacctgg gccacaatca     420

cagtttccgc agtatccatc atcagttgga acgcctctga gcactccatc acctgagtca     480

ggtaatacat ttactgattc atcctcagcg gactctgata tgacatccac taaaaaatat     540

gtcagaccac caccaatgtt aacctcacct aatgactttc caaattgggt taaaacatac     600

atcaaatttt tacaaaactc gaatctcggt ggtattattc cgacagtaaa cggaaaaccc     660

gtacgtccga tcactgatga tgaactcacc ttcttgtata acgcttttca aatatttgct     720

ccctctcaat tcctacctac ctgggtcaaa gacatcctat ccgttgatta tacggatatc     780
```

```
atgaaaattc tttccaaaag tattgaaaaa atgcaatctg atacccaaga ggcaaacgac    840

attgtgaccc tggcaaattt gcaatataat ggcagtacac ctgcagatgc atttgaaaca    900

aaagtcacaa acattatcga cagactgaac aataatggca ttcatatcaa taacaaggtc    960

gcatgtcaat taattatgag aggtctatct ggcgaatata aatttttacg ctacacacgt   1020

catcgacatc taaatatgac agtcgctgaa ctgttcttag atatccatgc tatttatgaa   1080

gaacaacagg gatcgagaaa cagcaaacct aattacagga gaaatccgag tgatgagaag   1140

aatgattctc gcagctatac gaatacaacc aaacccaaag ttatagctcg gaatcctcaa   1200

aaaacaaata attcgaaatc gaaaacagcc agggctcaca atgtatccac atctaataac   1260

tctcccagca cggacaacga ttccatcagt aaatcaacta ctgaaccgat tcaattgaac   1320

aataagcacg accttcatct taggccagaa acttacggca gcggcagcgg ccaccaccac   1380

caccaccact ga                                                       1392
```

```
<210> SEQ ID NO 12
<211> LENGTH: 463
<212> TYPE: PRT
<213> ORGANISM: Artificial sequence
<220> FEATURE:
<223> OTHER INFORMATION: 6His-Gag of Ty1-6His

<400> SEQUENCE: 12

Met His His His His His His Gly Ser Gly Ser Gly Met Glu Ser Gln
1               5                   10                  15

Gln Leu Ser Asn Tyr Pro His Ile Ser His Gly Ser Ala Cys Ala Ser
            20                  25                  30

Val Thr Ser Lys Glu Val His Thr Asn Gln Asp Pro Leu Asp Val Ser
        35                  40                  45

Ala Ser Lys Ile Gln Glu Tyr Asp Lys Ala Ser Thr Lys Ala Asn Ser
    50                  55                  60

Gln Gln Thr Thr Thr Pro Ala Ser Ser Ala Val Pro Glu Asn Pro His
65                  70                  75                  80

His Ala Ser Pro Gln Pro Ala Ser Val Pro Pro Pro Gln Asn Gly Pro
                85                  90                  95

Tyr Pro Gln Gln Cys Met Met Thr Gln Asn Gln Ala Asn Pro Ser Gly
            100                 105                 110

Trp Ser Phe Tyr Gly His Pro Ser Met Ile Pro Tyr Thr Pro Tyr Gln
        115                 120                 125

Met Ser Pro Met Tyr Phe Pro Pro Gly Pro Gln Ser Gln Phe Pro Gln
    130                 135                 140

Tyr Pro Ser Ser Val Gly Thr Pro Leu Ser Thr Pro Ser Pro Glu Ser
145                 150                 155                 160

Gly Asn Thr Phe Thr Asp Ser Ser Ser Ala Asp Ser Asp Met Thr Ser
                165                 170                 175

Thr Lys Lys Tyr Val Arg Pro Pro Pro Met Leu Thr Ser Pro Asn Asp
            180                 185                 190

Phe Pro Asn Trp Val Lys Thr Tyr Ile Lys Phe Leu Gln Asn Ser Asn
        195                 200                 205

Leu Gly Gly Ile Ile Pro Thr Val Asn Gly Lys Pro Val Arg Pro Ile
    210                 215                 220

Thr Asp Asp Glu Leu Thr Phe Leu Tyr Asn Ala Phe Gln Ile Phe Ala
225                 230                 235                 240

Pro Ser Gln Phe Leu Pro Thr Trp Val Lys Asp Ile Leu Ser Val Asp
                245                 250                 255
```

```
Tyr Thr Asp Ile Met Lys Ile Leu Ser Lys Ser Ile Glu Lys Met Gln
            260                 265                 270

Ser Asp Thr Gln Glu Ala Asn Asp Ile Val Thr Leu Ala Asn Leu Gln
        275                 280                 285

Tyr Asn Gly Ser Thr Pro Ala Asp Ala Phe Glu Thr Lys Val Thr Asn
    290                 295                 300

Ile Ile Asp Arg Leu Asn Asn Asn Gly Ile His Ile Asn Asn Lys Val
305                 310                 315                 320

Ala Cys Gln Leu Ile Met Arg Gly Leu Ser Gly Glu Tyr Lys Phe Leu
                325                 330                 335

Arg Tyr Thr Arg His Arg His Leu Asn Met Thr Val Ala Glu Leu Phe
            340                 345                 350

Leu Asp Ile His Ala Ile Tyr Glu Glu Gln Gln Gly Ser Arg Asn Ser
        355                 360                 365

Lys Pro Asn Tyr Arg Arg Asn Pro Ser Asp Glu Lys Asn Asp Ser Arg
    370                 375                 380

Ser Tyr Thr Asn Thr Thr Lys Pro Lys Val Ile Ala Arg Asn Pro Gln
385                 390                 395                 400

Lys Thr Asn Asn Ser Lys Ser Lys Thr Ala Arg Ala His Asn Val Ser
                405                 410                 415

Thr Ser Asn Asn Ser Pro Ser Thr Asp Asn Asp Ser Ile Ser Lys Ser
            420                 425                 430

Thr Thr Glu Pro Ile Gln Leu Asn Asn Lys His Asp Leu His Leu Arg
        435                 440                 445

Pro Glu Thr Tyr Gly Ser Gly Ser Gly His His His His His His
    450                 455                 460
```

<210> SEQ ID NO 13
<211> LENGTH: 1329
<212> TYPE: DNA
<213> ORGANISM: Artificial sequence
<220> FEATURE:
<223> OTHER INFORMATION: addressing sequence (modified Gag)

<400> SEQUENCE: 13

```
aagcttgatg gatcccaaca attatctaat tacccacata tatctcatgg tagcgcctgt     60

gcttcggtta cttctaagga agtccacaca aatcaagatc cgttagacgt ttcagcttcc    120

aaaattcaag aatatgataa ggcttccact aaggctaact ctcaacagac aacaacacct    180

gcttcatcag ctgttccaga gaacccccat catgcctctc ctcaacctgc ttcagtacca    240

cctccacaga atgggccgta cccacagcag tgcatgatga cccaaaacca agccaatcca    300

tctggttggt cattttacgg acacccatct atgattccgt atacacctta tcaaatgtcg    360

cctatgtact ttccacctgg gccacaatca cagtttccgc agtatccatc atcagttgga    420

acgcctctga gcactccatc acctgagtca ggtaatacat ttactgattc atcctcagcg    480

gactctgata tgacatccac taaaaaatat gtcagaccac caccaatgtt aacctcacct    540

aatgactttc caaattgggt taaaacatac atcaaatttt tacaaaactc gaatctcggt    600

ggtattattc cgacagtaaa cggaaaaccc gtacgtccga tcactgatga tgaactcacc    660

ttcttgtata acgcttttca aatatttgct ccctctcaat tcctacctac ctgggtcaaa    720

gacatcctat ccgttgatta tacggatatc atgaaaattc tttccaaaag tattgaaaaa    780

atgcaatctg atacccaaga ggcaaacgac attgtgaccc tggcaaattt gcaatataat    840

ggcagtacac ctgcagatgc atttgaaaca aaagtcacaa acattatcga cagactgaac    900
```

```
aataatggca ttcatatcaa taacaaggtc gcatgtcaat taattatgag aggtctatct    960

ggcgaatata aatttttacg ctacacacgt catcgacatc taaatatgac agtcgctgaa   1020

ctgttcttag atatccatgc tatttatgaa gaacaacagg gatcgagaaa cagcaaacct   1080

aattacagga gaaatccgag tgatgagaag aatgattctc gcagctatac gaatacaacc   1140

aaacccaaag ttatagctcg gaatcctcaa aaaacaaata attcgaaatc gaaaacagcc   1200

agggctcaca atgtatccac atctaataac tctcccagca cggacaacga ttccatcagt   1260

aaatcaacta ctgaaccgat tcaattgaac aataagcacg accttcatct taggccagaa   1320

acttactga                                                           1329
```

```
<210> SEQ ID NO 14
<211> LENGTH: 1329
<212> TYPE: RNA
<213> ORGANISM: Artificial sequence
<220> FEATURE:
<223> OTHER INFORMATION: addressing sequence (modified Gag)

<400> SEQUENCE: 14

aagcuugaug gaucccaaca auuaucuaau uacccacaua uaucucaugg uagcgccugu     60

gcuucgguua cuucuaagga aguccacaca aaucaagauc cguuagacgu uucagcuucc    120

aaaauucaag aauaugauaa ggcuuccacu aaggcuaacu cucaacagac aacaacaccu    180

gcuucaucag cuguuccaga gaaccccau caugccucuc cucaaccugc uucaguacca     240

ccuccacaga augggccgua cccacagcag ugcaugauga cccaaaacca agccaaucca    300

ucugguuggu cauuuuacgg acacccaucu augauuccgu auacaccuua ucaaaugucg    360

ccuauguacu uuccaccugg gccacaauca caguuuccgc aguauccauc aucaguugga    420

acgccucuga gcacuccauc accugaguca gguaauacau uuacugauuc auccucagcg    480

gacucugaua ugacauccac uaaaaaauau gucagaccac caccaauguu aaccucaccu    540

aaugacuuuc caaauugggu uaaaacauac aucaaauuuu uacaaaacuc gaaucucggu    600

gguauuauuc cgacaguaaa cggaaaaccc guacguccga ucacugauga ugaacucacc    660

uucuuguaua acgcuuuuca aauauuugcu cccucucaau uccuaccuac cugggucaaa    720

gacauccuau ccguugauua uacggauauc augaaaauuc uuuccaaaag uauugaaaaa    780

augcaaucug auacccaaga ggcaaacgac auugugaccc uggcaaauuu gcaauauaau    840

ggcaguacac cugcagaugc auuugaaaca aaagucacaa acauuaucga cagacugaac    900

aauaaauggca uucauaucaa uaacaagguc gcaugucaau uaauuaugag aggucuaucu    960

ggcgaauaua aauuuuuacg cuacacacgu caucgacauc uaaauaugac agucgcugaa   1020

cuguucuuag auauccaugc uauuuaugaa gaacaacagg gaucgagaaa cagcaaaccu   1080

aauuacagga gaaauccgag ugaugagaag aaugauucuc gcagcuauac gaauacaacc   1140

aaacccaaag uuauagcucg gaauccucaa aaaacaaaua auucgaaauc gaaaacagcc   1200

agggcucaca auguauccac aucuaauaac ucucccagca cggacaacga uuccaucagu   1260

aaaucaacua cugaaccgau ucaauugaac aauaagcacg accuucaucu uaggccagaa   1320

acuuacuga                                                           1329
```

```
<210> SEQ ID NO 15
<211> LENGTH: 398
<212> TYPE: DNA
<213> ORGANISM: Artificial sequence
<220> FEATURE:
```

<223> OTHER INFORMATION: addressing sequence (Gag fragment)

<400> SEQUENCE: 15

```
ccacagcagt gcatgatgac ccaaaaccaa gccaatccat ctggttggtc attttacgga     60
cacccatcta tgattccgta tacaccttat caaatgtcgc ctatgtactt tccacctggg    120
ccacaatcac agtttccgca gtatccatca tcagttggaa cgcctctgag cactccatca    180
cctgagtcag gtaatacatt tactgattca tcctcagcgg actctgatat gacatccact    240
aaaaaatatg tcagaccacc accaatgtta acctcaccta atgactttcc aaattgggtt    300
aaaacataca tcaaattttt acaaaactcg aatctcggtg gtattattcc gacagtaaac    360
ggaaaacccg tacgtccgat cactgatgat gaactcac                            398
```

<210> SEQ ID NO 16
<211> LENGTH: 398
<212> TYPE: RNA
<213> ORGANISM: Artificial sequence
<220> FEATURE:
<223> OTHER INFORMATION: addressing sequence (Gag fragment)

<400> SEQUENCE: 16

```
ccacagcagu gcaugaugac ccaaaaccaa gccaauccau cugguugguc auuuuacgga     60
cacccaucua ugauuccgua uacaccuuau caaaugucgc cuauguacuu uccaccuggg    120
ccacaaucac aguuuccgca guauccauca ucaguuggaa cgccucugag cacuccauca    180
ccugagucag guaauacauu uacugauuca uccucagcgg acucugauau gacauccacu    240
aaaaaauaug ucagaccacc accaauguua accucaccua augacuuucc aaauuggguu    300
aaaacauaca ucaaauuuuu acaaaacucg aaucucggug guauuauucc gacaguaaac    360
ggaaaacccg uacguccgau cacugaugau gaacucac                            398
```

<210> SEQ ID NO 17
<211> LENGTH: 1068
<212> TYPE: DNA
<213> ORGANISM: Artificial sequence
<220> FEATURE:
<223> OTHER INFORMATION: addressing sequence (Gag fragment)

<400> SEQUENCE: 17

```
ccacagcagt gcatgatgac ccaaaaccaa gccaatccat ctggttggtc attttacgga     60
cacccatcta tgattccgta tacaccttat caaatgtcgc ctatgtactt tccacctggg    120
ccacaatcac agtttccgca gtatccatca tcagttggaa cgcctctgag cactccatca    180
cctgagtcag gtaatacatt tactgattca tcctcagcgg actctgatat gacatccact    240
aaaaaatatg tcagaccacc accaatgtta acctcaccta atgactttcc aaattgggtt    300
aaaacataca tcaaattttt acaaaactcg aatctcggtg gtattattcc gacagtaaac    360
ggaaaacccg tacgtccgat cactgatgat gaactcacct tcttgtataa cgcttttcaa    420
atatttgctc cctctcaatt cctacctacc tgggtcaaag acatcctatc cgttgattat    480
acggatatca tgaaaattct ttccaaaagt attgaaaaaa tgcaatctga tacccaagag    540
gcaaacgaca ttgtgaccct ggcaaatttg caatataatg gcagtacacc tgcagatgca    600
tttgaaacaa aagtcacaaa cattatcgac agactgaaca ataatggcat tcatatcaat    660
aacaaggtcg catgtcaatt aattatgaga ggtctatctg gcgaatataa atttttacgc    720
tacacacgtc atcgacatct aaatatgaca gtcgctgaac tgttcttaga tatccatgct    780
atttatgaag aacaacaggg atcgagaaac agcaaaccta attacaggag aaatccgagt    840
```

gatgagaaga atgattctcg cagctatacg aatacaacca aacccaaagt tatagctcgg 900
aatcctcaaa aaacaaataa ttcgaaatcg aaaacagcca gggctcacaa tgtatccaca 960
tctaataact ctcccagcac ggacaacgat tccatcagta aatcaactac tgaaccgatt 1020
caattgaaca ataagcacga ccttcatctt aggccagaaa cttactga 1068

<210> SEQ ID NO 18
<211> LENGTH: 1068
<212> TYPE: RNA
<213> ORGANISM: Artificial sequence
<220> FEATURE:
<223> OTHER INFORMATION: addressing sequence (Gag fragment)

<400> SEQUENCE: 18
ccacagcagu gcaugaugac ccaaaaccaa gccaauccau cugguugguc auuuuacgga 60
cacccaucua ugauuccgua uacaccuuau caaaugucgc cuauguacuu uccaccuggg 120
ccacaaucac aguuuccgca guauccauca ucaguuggaa cgccucugag cacuccauca 180
ccugagucag guaauacauu uacugauuca uccucagcgg acucugauau gacauccacu 240
aaaaaauaug ucagaccacc accaauguua accucaccua augacuuucc aaauuggguu 300
aaaacauaca ucaaauuuuu acaaaacucg aaucucggug guauuauucc gacaguaaac 360
ggaaaacccg uacguccgau cacugaugau gaacucaccu ucuuguauaa cgcuuuucaa 420
auauuugcuc ccucucaauu ccuaccuacc ugggucaaag acauccuauc cguugauuau 480
acggauauca ugaaaauucu uuccaaaagu auugaaaaaa ugcaaucuga uacccaagag 540
gcaaacgaca uugugacccu ggcaaauuug caauauaaug gcaguacacc ugcagaugca 600
uuugaaacaa aagucacaaa cauuaucgac agacugaaca auaauggcau ucauaucaau 660
aacaaggucg caugucaauu aauuaugaga ggucuaucug gcgaauauaa auuuuuacgc 720
uacacacguc aucgacaucu aaauaugaca gucgcugaac uguucuuaga uauccaugcu 780
auuuaugaag aacaacaggg aucgagaaac agcaaaccua auuacaggag aaauccgagu 840
gaugagaaga augauucucg cagcuauacg aauacaacca aacccaaagu uauagcucgg 900
aauccucaaa aaacaaauaa uucgaaaucg aaaacagcca gggcucacaa uguauccaca 960
ucuaauaacu cucccagcac ggacaacgau uccaucagua aaucaacuac ugaaccgauu 1020
caauugaaca auaagcacga ccuucaucuu aggccagaaa cuuacuga 1068

<210> SEQ ID NO 19
<211> LENGTH: 73
<212> TYPE: DNA
<213> ORGANISM: Artificial sequence
<220> FEATURE:
<223> OTHER INFORMATION: FQ3 primer

<400> SEQUENCE: 19
tagcactagt atgcaccacc accaccacca cggcagcggc agcggcatgg aatcccaaca 60
attatctaat tac 73

<210> SEQ ID NO 20
<211> LENGTH: 31
<212> TYPE: DNA
<213> ORGANISM: Artificial sequence
<220> FEATURE:
<223> OTHER INFORMATION: RQ3 primer

<400> SEQUENCE: 20
gctaaagctt tcagtaagtt tctggcctaa g 31

<210> SEQ ID NO 21
<211> LENGTH: 37
<212> TYPE: DNA
<213> ORGANISM: Artificial sequence
<220> FEATURE:
<223> OTHER INFORMATION: FQ4 primer

<400> SEQUENCE: 21
tagcactagt atggaatccc aacaattatc taattac 37

<210> SEQ ID NO 22
<211> LENGTH: 92
<212> TYPE: DNA
<213> ORGANISM: Artificial sequence
<220> FEATURE:
<223> OTHER INFORMATION: RQ4 primer

<400> SEQUENCE: 22
gctaatgact cgaggtcgac ggtatcgata agctttcagt ggtggtggtg gtggtggccg 60
ctgccgctgc cgtaagtttc tggcctaaga tg 92

<210> SEQ ID NO 23
<211> LENGTH: 23
<212> TYPE: DNA
<213> ORGANISM: Artificial sequence
<220> FEATURE:
<223> OTHER INFORMATION: qGAGF primer

<400> SEQUENCE: 23
gctgtttctc gatccctgtt gtt 23

<210> SEQ ID NO 24
<211> LENGTH: 22
<212> TYPE: DNA
<213> ORGANISM: Artificial sequence
<220> FEATURE:
<223> OTHER INFORMATION: qGAGR primer

<400> SEQUENCE: 24
agaggcaaac gacattgtga cc 22

<210> SEQ ID NO 25
<211> LENGTH: 720
<212> TYPE: DNA
<213> ORGANISM: Bacillus cereus

<400> SEQUENCE: 25
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 26
<211> LENGTH: 720
<212> TYPE: RNA
<213> ORGANISM: Bacillus cereus

<400> SEQUENCE: 26
auggugagca agggcgagga gcuguucacc gggguggugc ccauccuggu cgagcuggac 60
ggcgacguaa acggccacaa guucagcgug uccggcgagg gcgagggcga ugccaccuac 120
ggcaagcuga cccugaaguu caucugcacc accggcaagc ugcccgugcc cuggcccacc 180
cucgugacca cccugaccua cggcgugcag ugcuucagcc gcuaccccga ccacaugaag 240
cagcacgacu ucuucaaguc cgccaugccc gaaggcuacg uccaggagcg caccaucuuc 300
uucaaggacg acggcaacua caagacccgc gccgaggua aguucgaggg cgacacccug 360
gugaaccgca ucgagcugaa gggcaucgac uucaaggagg acggcaacau ccuggggcac 420
aagcuggagu acaacuacaa cagccacaac gucuauauca uggccgacaa gcagaagaac 480
ggcaucaagg ugaacuucaa gauccgccac aacaucgagg acggcagcgu gcagcucgcc 540
gaccacuacc agcagaacac ccccaucggc gacggccccg ugcugcugcc cgacaaccac 600
uaccugagca cccaguccgc ccugagcaaa gaccccaacg agaagcgcga ucacaugguc 660
cugcuggagu ucgugaccgc cgccgggauc acucucggca uggacgagcu guacaaguaa 720

<210> SEQ ID NO 27
<211> LENGTH: 239
<212> TYPE: PRT
<213> ORGANISM: Bacillus cereus

<400> SEQUENCE: 27

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Phe Ile
35 40 45

Cys Thr Thr Gly Lys Leu Pro Val Pro Trp Pro Thr Leu Val Thr Thr
50 55 60

Leu Thr Tyr Gly Val Gln Cys Phe Ser Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

Ile Asp Phe Lys Glu Asp Gly Asn Ile Leu Gly His Lys Leu Glu Tyr
130 135 140

Asn Tyr Asn Ser His Asn Val Tyr Ile Met Ala Asp Lys Gln Lys Asn
145 150 155 160

Gly Ile Lys Val Asn Phe Lys Ile Arg His Asn Ile Glu Asp Gly Ser
165 170 175

Val Gln Leu Ala Asp His Tyr Gln Gln Asn Thr Pro Ile Gly Asp Gly

```
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 28
<211> LENGTH: 1653
<212> TYPE: DNA
<213> ORGANISM: Artificial sequence
<220> FEATURE:
<223> OTHER INFORMATION: Luciferase

<400> SEQUENCE: 28

atggaagacg ccaaaaacat aaagaaaggc ccggcgccat tctatccgct ggaagatgga     60

accgctggag agcaactgca taaggctatg aagagatacg ccctggttcc tggaacaatt    120

gcttttacag atgcacatat cgaggtggac atcacttacg ctgagtactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgggcatt    360

tcgcagccta ccgtggtgtt cgtttccaaa aaggggttgc aaaaaatttt gaacgtgcaa    420

aaaaagctcc caatcatcca aaaaattatt atcatggatt ctaaaacgga ttaccaggga    480

tttcagtcga tgtacacgtt cgtcacatct catctacctc ccggttttaa tgaatacgat    540

tttgtgccag agtccttcga tagggacaag acaattgcac tgatcatgaa ctcctctgga    600

tctactggtc tgcctaaagg tgtcgctctg cctcatagaa ctgcctgcgt gagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttc tgaggagcct tcaggattac    840

aagattcaaa gtgcgctgct ggtgccaacc ctattctcct tcttcgccaa aagcactctg    900

attgacaaat acgatttatc taatttacac gaaattgctt ctggtggcgc tcccctctct    960

aaggaagtcg gggaagcggt tgccaagagg ttccatctgc caggtatcag gcaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcaaag aggcgaactg tgtgtgagag gtcctatgat tatgtccggt   1200

tatgtaaaca atccggaagc gaccaacgcc ttgattgaca aggatggatg gctacattct   1260

ggagacatag cttactggga cgaagacgaa cacttcttca tcgttgaccg cctgaagtct   1320

ctgattaagt acaaaggcta tcaggtggct cccgctgaat tggaatccat cttgctccaa   1380

caccccaaca tcttcgacgc aggtgtcgca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gatcgccgtg taa                                1653


<210> SEQ ID NO 29
```

<211> LENGTH: 1653
<212> TYPE: RNA
<213> ORGANISM: Artificial sequence
<220> FEATURE:
<223> OTHER INFORMATION: Luciferase

<400> SEQUENCE: 29

```
auggaagacg ccaaaaacau aaagaaaggc ccggcgccau ucuauccgcu ggaagaugga     60
accgcuggag agcaacugca uaaggcuaug aagagauacg cccugguucc uggaacaauu    120
gcuuuuacag augcacauau cgagguggac aucacuuacg cugaguacuu cgaaaugucc    180
guucgguugg cagaagcuau gaaacgauau gggcugaaua caaaucacag aaucgucgua    240
ugcagugaaa acucucuuca auucuuuaug ccgguguugg gcgcguuauu uaucggaguu    300
gcaguugcgc ccgcgaacga cauuuauaau gaacgugaau ugcucaacag uaugggcauu    360
ucgcagccua ccguggugu u cguuuccaaa aagggguugc aaaaaauuuu gaacgugcaa    420
aaaaagcucc caaucaucca aaaaauuauu aucauggauu cuaaaacgga uuaccaggga    480
uuucagucga uguacacguu cgucacaucu caucuaccuc ccgguuuuaa ugaauacgau    540
uuugugccag aguccuucga uagggacaag acaauugcac ugaucaugaa cuccucugga    600
ucuacugguc ugccuaaagg ugucgcucug ccucauagaa cugccugcgu gagauucucg    660
caugccagag auccuauuuu uggcaaucaa aucauuccgg auacugcgau uuuaaguguu    720
guuccauucc aucacgguuu uggaauguuu acuacacucg gauauuugau auguggauuu    780
cgagucgucu uaauguauag auuugaagaa gagcuguuuc ugaggagccu ucaggauuac    840
aagauucaaa gugcgcugcu ggugccaacc cuauucuccu ucuucgccaa aagcacucug    900
auugacaaau acgauuuauc uaauuuacac gaaauugcuu cugguggcgc uccccucucu    960
aaggaagucg gggaagcggu ugccaagagg uuccaucugc cagguaucag gcaaggauau   1020
gggcucacug agacuacauc agcuauucug auuacacccg agggggauga uaaaccgggc   1080
gcggucggua aaguuguucc auuuuuugaa gcgaagguug uggaucugga uaccgggaaa   1140
acgcugggcg uuaaucaaag aggcgaacug ugugugagag guccuaugau uauguccggu   1200
uauguaaaca auccggaagc gaccaacgcc uugauugaca aggauggaug gcuacauucu   1260
ggagacauag cuuacuggga cgaagacgaa cacuucuuca ucguugaccg ccugaagucu   1320
cugauuaagu acaaaggcua ucagguggcu cccgcugaau uggaauccau cuugcuccaa   1380
caccccaaca ucuucgacgc aggugucgca ggucuucccg acgaugacgc cggugaacuu   1440
cccgccgccg uuguuguuuu ggagcacgga aagacgauga cggaaaaaga gaucguggau   1500
uacgucgcca gucaaguaac aaccgcgaaa aaguugcgcg gaggaguugu guuuguggac   1560
gaaguaccga aaggucuuac cggaaaacuc gacgcaagaa aaaucagaga gauccucaua   1620
aaggccaaga agggcggaaa gaucgccgug uaa                                1653
```

<210> SEQ ID NO 30
<211> LENGTH: 550
<212> TYPE: PRT
<213> ORGANISM: Artificial sequence
<220> FEATURE:
<223> OTHER INFORMATION: Luciferase

<400> SEQUENCE: 30

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30
```

```
Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445
```

```
Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550


<210> SEQ ID NO 31
<211> LENGTH: 37
<212> TYPE: DNA
<213> ORGANISM: Artificial sequence
<220> FEATURE:
<223> OTHER INFORMATION: FQ5 primer

<400> SEQUENCE: 31

tgatactagt atggaatccc aacaattatc taattac                             37


<210> SEQ ID NO 32
<211> LENGTH: 30
<212> TYPE: DNA
<213> ORGANISM: Artificial sequence
<220> FEATURE:
<223> OTHER INFORMATION: RQ5 primer

<400> SEQUENCE: 32

atcgaattcg taagtttctg gcctaagatg                                     30


<210> SEQ ID NO 33
<211> LENGTH: 55
<212> TYPE: DNA
<213> ORGANISM: Artificial sequence
<220> FEATURE:
<223> OTHER INFORMATION: FQ6 primer

<400> SEQUENCE: 33

tacgactcac tatagggcga attggagctc tagtacggat tagaagccgc cgagc         55


<210> SEQ ID NO 34
<211> LENGTH: 55
<212> TYPE: DNA
<213> ORGANISM: Artificial sequence
<220> FEATURE:
<223> OTHER INFORMATION: RQ6 primer

<400> SEQUENCE: 34

cctcactaaa gggaacaaaa gctgggtacc ggccgcaaat taaagccttc gagcg         55


<210> SEQ ID NO 35
<211> LENGTH: 98
<212> TYPE: DNA
<213> ORGANISM: Artificial sequence
<220> FEATURE:
<223> OTHER INFORMATION: 3MS2

<400> SEQUENCE: 35
```

```
atatccgtac accatcaggg tacgagctag cccatggcgt acaccatcag ggtacgacga     60

gtagatctcg tacaccatca gggtacggaa tcgctgac                             98


<210> SEQ ID NO 36
<211> LENGTH: 98
<212> TYPE: RNA
<213> ORGANISM: Artificial sequence
<220> FEATURE:
<223> OTHER INFORMATION: 3MS2

<400> SEQUENCE: 36

auauccguac accaucaggg uacgagcuag cccauggcgu acaccaucag gguacgacga     60

guagaucucg uacaccauca ggguacggaa ucgcugac                             98


<210> SEQ ID NO 37
<211> LENGTH: 1320
<212> TYPE: DNA
<213> ORGANISM: Saccharomyces cerevisiae

<400> SEQUENCE: 37

atggaatccc aacaattatc taattaccca catatatctc atggtagcgc ctgtgcttcg     60

gttacttcta aggaagtcca cacaaatcaa gatccgttag acgtttcagc ttccaaaatt    120

caagaatatg ataaggcttc cactaaggct aactctcaac agacaacaac acctgcttca    180

tcagctgttc cagagaaccc ccatcatgcc tctcctcaac ctgcttcagt accacctcca    240

cagaatgggc cgtacccaca gcagtgcatg atgacccaaa accaagccaa tccatctggt    300

tggtcatttt acggacaccc atctatgatt ccgtatacac cttatcaaat gtcgcctatg    360

tactttccac ctgggccaca atcacagttt ccgcagtatc catcatcagt tggaacgcct    420

ctgagcactc catcacctga gtcaggtaat acatttactg attcatcctc agcggactct    480

gatatgacat ccactaaaaa atatgtcaga ccaccaccaa tgttaacctc acctaatgac    540

tttccaaatt gggttaaaac atacatcaaa tttttacaaa actcgaatct cggtggtatt    600

attccgacag taaacggaaa acccgtacgt ccgatcactg atgatgaact caccttcttg    660

tataacgctt ttcaaatatt tgctccctct caattcctac ctacctgggt caaagacatc    720

ctatccgttg attatacgga tatcatgaaa attctttcca aaagtattga aaaaatgcaa    780

tctgataccc aagaggcaaa cgacattgtg accctggcaa atttgcaata taatggcagt    840

acacctgcag atgcatttga aacaaaagtc acaaacatta tcgacagact gaacaataat    900

ggcattcata tcaataacaa ggtcgcatgt caattaatta tgagaggtct atctggcgaa    960

tataaatttt tacgctacac acgtcatcga catctaaata tgacagtcgc tgaactgttc   1020

ttagatatcc atgctattta tgaagaacaa cagggatcga gaaacagcaa acctaattac   1080

aggagaaatc cgagtgatga gaagaatgat tctcgcagct atacgaatac aaccaaaccc   1140

aaagttatag ctcggaatcc tcaaaaaaca aataattcga aatcgaaaac agccagggct   1200

cacaatgtat ccacatctaa taactctccc agcacggaca acgattccat cagtaaatca   1260

actactgaac cgattcaatt gaacaataag cacgaccttc atcttaggcc agaaacttac   1320


<210> SEQ ID NO 38
<211> LENGTH: 2371
<212> TYPE: DNA
<213> ORGANISM: Artificial sequence
<220> FEATURE:
<223> OTHER INFORMATION: GAG of Ty1 - eGFP - 6His - 3MS2

<400> SEQUENCE: 38
```

```
actagttcta tggaatccca acaattatct aattacccac atatatctca tggtagcgcc     60
tgtgcttcgg ttacttctaa ggaagtccac acaaatcaag atccgttaga cgtttcagct    120
tccaaaattc aagaatatga taaggcttcc actaaggcta actctcaaca gacaacaaca    180
cctgcttcat cagctgttcc agagaacccc catcatgcct ctcctcaacc tgcttcagta    240
ccacctccac agaatgggcc gtacccacag cagtgcatga tgacccaaaa ccaagccaat    300
ccatctggtt ggtcatttta cggacaccca tctatgattc cgtatacacc ttatcaaatg    360
tcgcctatgt actttccacc tgggccacaa tcacagtttc cgcagtatcc atcatcagtt    420
ggaacgcctc tgagcactcc atcacctgag tcaggtaata catttactga ttcatcctca    480
gcggactctg atatgacatc cactaaaaaa tatgtcagac caccaccaat gttaacctca    540
cctaatgact ttccaaattg ggttaaaaca tacatcaaat ttttacaaaa ctcgaatctc    600
ggtggtatta ttccgacagt aaacggaaaa cccgtacgtc cgatcactga tgatgaactc    660
accttcttgt ataacgcttt tcaaatattt gctccctctc aattcctacc tacctgggtc    720
aaagacatcc tatccgttga ttatacggat atcatgaaaa ttctttccaa aagtattgaa    780
aaaatgcaat ctgataccca agaggcaaac gacattgtga ccctggcaaa tttgcaatat    840
aatggcagta cacctgcaga tgcatttgaa acaaaagtca caaacattat cgacagactg    900
aacaataatg gcattcatat caataacaag gtcgcatgtc aattaattat gagaggtcta    960
tctggcgaat ataaattttt acgctacaca cgtcatcgac atctaaatat gacagtcgct   1020
gaactgttct tagatatcca tgctatttat gaagaacaac agggatcgag aaacagcaaa   1080
cctaattaca ggagaaatcc gagtgatgag aagaatgatt ctcgcagcta tacgaataca   1140
accaaaccca aagttatagc tcggaatcct caaaaaacaa ataattcgaa atcgaaaaca   1200
gccagggctc acaatgtatc cacatctaat aactctccca gcacggacaa cgattccatc   1260
agtaaatcaa ctactgaacc gattcaattg aacaataagc acgaccttca tcttaggcca   1320
gaaacttacg aattgatatc aagcttaatg gtgagcaagg gcgaggagct gttcaccggg   1380
gtggtgccca tcctggtcga gctggacggc gacgtaaacg gccacaagtt cagcgtgtcc   1440
ggcgagggcg agggcgatgc cacctacggc aagctgaccc tgaagttcat ctgcaccacc   1500
ggcaagctgc ccgtgccctg gcccaccctc gtgaccaccc tgacctacgg cgtgcagtgc   1560
ttcagccgct accccgacca catgaagcag cacgacttct tcaagtccgc catgcccgaa   1620
ggctacgtcc aggagcgcac catcttcttc aaggacgacg gcaactacaa gacccgcgcc   1680
gaggtgaagt tcgagggcga caccctggtg aaccgcatcg agctgaaggg catcgacttc   1740
aaggaggacg gcaacatcct ggggcacaag ctggagtaca actacaacag ccacaacgtc   1800
tatatcatgg ccgacaagca gaagaacggc atcaaggtga acttcaagat ccgccacaac   1860
atcgaggacg gcagcgtgca gctcgccgac cactaccagc agaacacccc catcggcgac   1920
ggccccgtgc tgctgcccga caaccactac ctgagcaccc agtccgccct gagcaaagac   1980
cccaacgaga agcgcgatca catggtcctg ctggagttcg tgaccgccgc cgggatcact   2040
ctcggcatgg acgagctgta caagcggcag cggcagcgcc atcatcatca tcatcattaa   2100
gcggccgctg taattagtta tgtcacgctt acattcacgc cctccatatc cgtacaccat   2160
cagggtacga gctagcccat ggcgtacacc atcagggtac gacgagtaga tctcgtacac   2220
catcagggta cggaatcgct gacgtacctt taatatagtg tgatttttaa aaactttcga   2280
acaagaatca gtaatataat atatataatt aataaaacta atggaatttg tttaattgaa   2340
```

cttgacaccc gagaagtgcg gccgcggtac c 2371

<210> SEQ ID NO 39
<211> LENGTH: 2101
<212> TYPE: DNA
<213> ORGANISM: Artificial sequence
<220> FEATURE:
<223> OTHER INFORMATION: GAG of Ty1 - eGFP - 6His

<400> SEQUENCE: 39
ctagttctat ggaatcccaa caattatcta attacccaca tatatctcat ggtagcgcct 60
gtgcttcggt tacttctaag gaagtccaca caaatcaaga tccgttagac gtttcagctt 120
ccaaaattca agaatatgat aaggcttcca ctaaggctaa ctctcaacag acaacaacac 180
ctgcttcatc agctgttcca gagaaccccc atcatgcctc tcctcaacct gcttcagtac 240
cacctccaca gaatgggccg tacccacagc agtgcatgat gacccaaaac caagccaatc 300
catctggttg gtcattttac ggacacccat ctatgattcc gtatacacct tatcaaatgt 360
cgcctatgta ctttccacct gggccacaat cacagtttcc gcagtatcca tcatcagttg 420
gaacgcctct gagcactcca tcacctgagt caggtaatac atttactgat tcatcctcag 480
cggactctga tatgacatcc actaaaaaat atgtcagacc accaccaatg ttaacctcac 540
ctaatgactt tccaaattgg gttaaaacat acatcaaatt tttacaaaac tcgaatctcg 600
gtggtattat tccgacagta aacggaaaac ccgtacgtcc gatcactgat gatgaactca 660
ccttcttgta taacgctttt caaatatttg ctccctctca attcctacct acctgggtca 720
aagacatcct atccgttgat tatacggata tcatgaaaat tctttccaaa agtattgaaa 780
aaatgcaatc tgatacccaa gaggcaaacg acattgtgac cctggcaaat ttgcaatata 840
atggcagtac acctgcagat gcatttgaaa caaaagtcac aaacattatc gacagactga 900
acaataatgg cattcatatc aataacaagg tcgcatgtca attaattatg agaggtctat 960
ctggcgaata taaattttta cgctacacac gtcatcgaca tctaaatatg acagtcgctg 1020
aactgttctt agatatccat gctatttatg aagaacaaca gggatcgaga aacagcaaac 1080
ctaattacag gagaaatccg agtgatgaga agaatgattc tcgcagctat acgaatacaa 1140
ccaaacccaa agttatagct cggaatcctc aaaaaacaaa taattcgaaa tcgaaaacag 1200
ccagggctca caatgtatcc acatctaata actctcccag cacggacaac gattccatca 1260
gtaaatcaac tactgaaccg attcaattga acaataagca cgaccttcat cttaggccag 1320
aaacttacga attgatatca agcttaatgg tgagcaaggg cgaggagctg ttcaccgggg 1380
tggtgcccat cctggtcgag ctggacggcg acgtaaacgg ccacaagttc agcgtgtccg 1440
gcgagggcga gggcgatgcc acctacggca agctgaccct gaagttcatc tgcaccaccg 1500
gcaagctgcc cgtgccctgg cccaccctcg tgaccaccct gacctacggc gtgcagtgct 1560
tcagccgcta ccccgaccac atgaagcagc acgacttctt caagtccgcc atgcccgaag 1620
gctacgtcca ggagcgcacc atcttcttca aggacgacgg caactacaag acccgcgccg 1680
aggtgaagtt cgagggcgac accctggtga accgcatcga gctgaagggc atcgacttca 1740
aggaggacgg caacatcctg gggcacaagc tggagtacaa ctacaacagc cacaacgtct 1800
atatcatggc cgacaagcag aagaacggca tcaaggtgaa cttcaagatc cgccacaaca 1860
tcgaggacgg cagcgtgcag ctcgccgacc actaccagca gaacaccccc atcggcgacg 1920
gccccgtgct gctgcccgac aaccactacc tgagcaccca gtccgccctg agcaaagacc 1980
ccaacgagaa gcgcgatcac atggtcctgc tggagttcgt gaccgccgcc gggatcactc 2040

```
tcggcatgga cgagctgtac aagcggcagc ggcagcgcca tcatcatcat catcattaag   2100

c                                                                    2101


<210> SEQ ID NO 40
<211> LENGTH: 696
<212> TYPE: PRT
<213> ORGANISM: Artificial sequence
<220> FEATURE:
<223> OTHER INFORMATION: GAG of Ty1 - eGFP - 6His

<400> SEQUENCE: 40

Met Glu Ser Gln Gln Leu Ser Asn Tyr Pro His Ile Ser His Gly Ser
1               5                   10                  15

Ala Cys Ala Ser Val Thr Ser Lys Glu Val His Thr Asn Gln Asp Pro
            20                  25                  30

Leu Asp Val Ser Ala Ser Lys Ile Gln Glu Tyr Asp Lys Ala Ser Thr
        35                  40                  45

Lys Ala Asn Ser Gln Gln Thr Thr Thr Pro Ala Ser Ser Ala Val Pro
    50                  55                  60

Glu Asn Pro His His Ala Ser Pro Gln Pro Ala Ser Val Pro Pro Pro
65                  70                  75                  80

Gln Asn Gly Pro Tyr Pro Gln Gln Cys Met Met Thr Gln Asn Gln Ala
                85                  90                  95

Asn Pro Ser Gly Trp Ser Phe Tyr Gly His Pro Ser Met Ile Pro Tyr
            100                 105                 110

Thr Pro Tyr Gln Met Ser Pro Met Tyr Phe Pro Pro Gly Pro Gln Ser
        115                 120                 125

Gln Phe Pro Gln Tyr Pro Ser Ser Val Gly Thr Pro Leu Ser Thr Pro
    130                 135                 140

Ser Pro Glu Ser Gly Asn Thr Phe Thr Asp Ser Ser Ser Ala Asp Ser
145                 150                 155                 160

Asp Met Thr Ser Thr Lys Lys Tyr Val Arg Pro Pro Pro Met Leu Thr
                165                 170                 175

Ser Pro Asn Asp Phe Pro Asn Trp Val Lys Thr Tyr Ile Lys Phe Leu
            180                 185                 190

Gln Asn Ser Asn Leu Gly Gly Ile Ile Pro Thr Val Asn Gly Lys Pro
        195                 200                 205

Val Arg Pro Ile Thr Asp Asp Glu Leu Thr Phe Leu Tyr Asn Ala Phe
    210                 215                 220

Gln Ile Phe Ala Pro Ser Gln Phe Leu Pro Thr Trp Val Lys Asp Ile
225                 230                 235                 240

Leu Ser Val Asp Tyr Thr Asp Ile Met Lys Ile Leu Ser Lys Ser Ile
                245                 250                 255

Glu Lys Met Gln Ser Asp Thr Gln Glu Ala Asn Asp Ile Val Thr Leu
            260                 265                 270

Ala Asn Leu Gln Tyr Asn Gly Ser Thr Pro Ala Asp Ala Phe Glu Thr
        275                 280                 285

Lys Val Thr Asn Ile Ile Asp Arg Leu Asn Asn Asn Gly Ile His Ile
    290                 295                 300

Asn Asn Lys Val Ala Cys Gln Leu Ile Met Arg Gly Leu Ser Gly Glu
305                 310                 315                 320

Tyr Lys Phe Leu Arg Tyr Thr Arg His Arg His Leu Asn Met Thr Val
                325                 330                 335

Ala Glu Leu Phe Leu Asp Ile His Ala Ile Tyr Glu Glu Gln Gln Gly
```

```
            340                 345                 350

Ser Arg Asn Ser Lys Pro Asn Tyr Arg Arg Asn Pro Ser Asp Glu Lys
        355                 360                 365

Asn Asp Ser Arg Ser Tyr Thr Asn Thr Thr Lys Pro Lys Val Ile Ala
    370                 375                 380

Arg Asn Pro Gln Lys Thr Asn Asn Ser Lys Ser Lys Thr Ala Arg Ala
385                 390                 395                 400

His Asn Val Ser Thr Ser Asn Asn Ser Pro Ser Thr Asp Asn Asp Ser
                405                 410                 415

Ile Ser Lys Ser Thr Thr Glu Pro Ile Gln Leu Asn Asn Lys His Asp
            420                 425                 430

Leu His Leu Arg Pro Glu Thr Tyr Glu Leu Ile Ser Ser Leu Met Val
        435                 440                 445

Ser Lys Gly Glu Glu Leu Phe Thr Gly Val Val Pro Ile Leu Val Glu
    450                 455                 460

Leu Asp Gly Asp Val Asn Gly His Lys Phe Ser Val Ser Gly Glu Gly
465                 470                 475                 480

Glu Gly Asp Ala Thr Tyr Gly Lys Leu Thr Leu Lys Phe Ile Cys Thr
                485                 490                 495

Thr Gly Lys Leu Pro Val Pro Trp Pro Thr Leu Val Thr Thr Leu Thr
            500                 505                 510

Tyr Gly Val Gln Cys Phe Ser Arg Tyr Pro Asp His Met Lys Gln His
        515                 520                 525

Asp Phe Phe Lys Ser Ala Met Pro Glu Gly Tyr Val Gln Glu Arg Thr
    530                 535                 540

Ile Phe Phe Lys Asp Asp Gly Asn Tyr Lys Thr Arg Ala Glu Val Lys
545                 550                 555                 560

Phe Glu Gly Asp Thr Leu Val Asn Arg Ile Glu Leu Lys Gly Ile Asp
                565                 570                 575

Phe Lys Glu Asp Gly Asn Ile Leu Gly His Lys Leu Glu Tyr Asn Tyr
            580                 585                 590

Asn Ser His Asn Val Tyr Ile Met Ala Asp Lys Gln Lys Asn Gly Ile
        595                 600                 605

Lys Val Asn Phe Lys Ile Arg His Asn Ile Glu Asp Gly Ser Val Gln
    610                 615                 620

Leu Ala Asp His Tyr Gln Gln Asn Thr Pro Ile Gly Asp Gly Pro Val
625                 630                 635                 640

Leu Leu Pro Asp Asn His Tyr Leu Ser Thr Gln Ser Ala Leu Ser Lys
                645                 650                 655

Asp Pro Asn Glu Lys Arg Asp His Met Val Leu Leu Glu Phe Val Thr
            660                 665                 670

Ala Ala Gly Ile Thr Leu Gly Met Asp Glu Leu Tyr Lys Arg Gln Arg
        675                 680                 685

Gln Arg His His His His His His
    690                 695
```

<210> SEQ ID NO 41
<211> LENGTH: 2058
<212> TYPE: DNA
<213> ORGANISM: Artificial sequence
<220> FEATURE:
<223> OTHER INFORMATION: GAG of Ty1 - eGFP

<400> SEQUENCE: 41

```
atggaatccc aacaattatc taattaccca catatatctc atggtagcgc ctgtgcttcg      60
```

```
gttacttcta aggaagtcca cacaaatcaa gatccgttag acgtttcagc ttccaaaatt    120
caagaatatg ataaggcttc cactaaggct aactctcaac agacaacaac acctgcttca    180
tcagctgttc cagagaaccc ccatcatgcc tctcctcaac ctgcttcagt accacctcca    240
cagaatgggc cgtacccaca gcagtgcatg atgacccaaa accaagccaa tccatctggt    300
tggtcatttt acggacaccc atctatgatt ccgtatacac cttatcaaat gtcgcctatg    360
tactttccac ctgggccaca atcacagttt ccgcagtatc catcatcagt tggaacgcct    420
ctgagcactc catcacctga gtcaggtaat acatttactg attcatcctc agcggactct    480
gatatgacat ccactaaaaa atatgtcaga ccaccaccaa tgttaacctc acctaatgac    540
tttccaaatt gggttaaaac atacatcaaa tttttacaaa actcgaatct cggtggtatt    600
attccgacag taaacggaaa acccgtacgt ccgatcactg atgatgaact caccttcttg    660
tataacgctt ttcaaatatt tgctccctct caattcctac ctacctgggt caaagacatc    720
ctatccgttg attatacgga tatcatgaaa attctttcca aaagtattga aaaaatgcaa    780
tctgataccc aagaggcaaa cgacattgtg accctggcaa atttgcaata taatggcagt    840
acacctgcag atgcatttga aacaaaagtc acaaacatta tcgacagact gaacaataat    900
ggcattcata tcaataacaa ggtcgcatgt caattaatta tgagaggtct atctggcgaa    960
tataaatttt tacgctacac acgtcatcga catctaaata tgacagtcgc tgaactgttc   1020
ttagatatcc atgctattta tgaagaacaa cagggatcga gaaacagcaa acctaattac   1080
aggagaaatc cgagtgatga gaagaatgat tctcgcagct atacgaatac aaccaaaccc   1140
aaagttatag ctcggaatcc tcaaaaaaca aataattcga aatcgaaaac agccagggct   1200
cacaatgtat ccacatctaa taactctccc agcacggaca acgattccat cagtaaatca   1260
actactgaac cgattcaatt gaacaataag cacgaccttc atcttaggcc agaaacttac   1320
gattcgatat caagcttaat ggtgagcaag ggcgaggagc tgttcaccgg ggtggtgccc   1380
atcctggtcg agctggacgg cgacgtaaac ggccacaagt tcagcgtgtc cggcgagggc   1440
gagggcgatg ccacctacgg caagctgacc ctgaagttca tctgcaccac cggcaagctg   1500
cccgtgccct ggcccaccct cgtgaccacc ctgacctacg gcgtgcagtg cttcagccgc   1560
taccccgacc acatgaagca gcacgacttc ttcaagtccg ccatgcccga aggctacgtc   1620
caggagcgca ccatcttctt caaggacgac ggcaactaca agacccgcgc cgaggtgaag   1680
ttcgagggcg acaccctggt gaaccgcatc gagctgaagg gcatcgactt caaggaggac   1740
ggcaacatcc tggggcacaa gctggagtac aactacaaca gccacaacgt ctatatcatg   1800
gccgacaagc agaagaacgg catcaaggtg aacttcaaga tccgccacaa catcgaggac   1860
ggcagcgtgc agctcgccga ccactaccag cagaacaccc ccatcggcga cggccccgtg   1920
ctgctgcccg acaaccacta cctgagcacc cagtccgccc tgagcaaaga ccccaacgag   1980
aagcgcgatc acatggtcct gctggagttc gtgaccgccg ccgggatcac tctcggcatg   2040
gacgagctgt acaagtaa                                                 2058
```

<210> SEQ ID NO 42
<211> LENGTH: 685
<212> TYPE: PRT
<213> ORGANISM: Artificial sequence
<220> FEATURE:
<223> OTHER INFORMATION: GAG of Ty1 - eGFP

<400> SEQUENCE: 42

```
Met Glu Ser Gln Gln Leu Ser Asn Tyr Pro His Ile Ser His Gly Ser
1               5                   10                  15

Ala Cys Ala Ser Val Thr Ser Lys Glu Val His Thr Asn Gln Asp Pro
            20                  25                  30

Leu Asp Val Ser Ala Ser Lys Ile Gln Glu Tyr Asp Lys Ala Ser Thr
        35                  40                  45

Lys Ala Asn Ser Gln Gln Thr Thr Thr Pro Ala Ser Ser Ala Val Pro
    50                  55                  60

Glu Asn Pro His His Ala Ser Pro Gln Pro Ala Ser Val Pro Pro Pro
65                  70                  75                  80

Gln Asn Gly Pro Tyr Pro Gln Gln Cys Met Met Thr Gln Asn Gln Ala
                85                  90                  95

Asn Pro Ser Gly Trp Ser Phe Tyr Gly His Pro Ser Met Ile Pro Tyr
            100                 105                 110

Thr Pro Tyr Gln Met Ser Pro Met Tyr Phe Pro Pro Gly Pro Gln Ser
        115                 120                 125

Gln Phe Pro Gln Tyr Pro Ser Ser Val Gly Thr Pro Leu Ser Thr Pro
    130                 135                 140

Ser Pro Glu Ser Gly Asn Thr Phe Thr Asp Ser Ser Ser Ala Asp Ser
145                 150                 155                 160

Asp Met Thr Ser Thr Lys Lys Tyr Val Arg Pro Pro Pro Met Leu Thr
                165                 170                 175

Ser Pro Asn Asp Phe Pro Asn Trp Val Lys Thr Tyr Ile Lys Phe Leu
            180                 185                 190

Gln Asn Ser Asn Leu Gly Gly Ile Ile Pro Thr Val Asn Gly Lys Pro
        195                 200                 205

Val Arg Pro Ile Thr Asp Asp Glu Leu Thr Phe Leu Tyr Asn Ala Phe
    210                 215                 220

Gln Ile Phe Ala Pro Ser Gln Phe Leu Pro Thr Trp Val Lys Asp Ile
225                 230                 235                 240

Leu Ser Val Asp Tyr Thr Asp Ile Met Lys Ile Leu Ser Lys Ser Ile
                245                 250                 255

Glu Lys Met Gln Ser Asp Thr Gln Glu Ala Asn Asp Ile Val Thr Leu
            260                 265                 270

Ala Asn Leu Gln Tyr Asn Gly Ser Thr Pro Ala Asp Ala Phe Glu Thr
        275                 280                 285

Lys Val Thr Asn Ile Ile Asp Arg Leu Asn Asn Asn Gly Ile His Ile
    290                 295                 300

Asn Asn Lys Val Ala Cys Gln Leu Ile Met Arg Gly Leu Ser Gly Glu
305                 310                 315                 320

Tyr Lys Phe Leu Arg Tyr Thr Arg His Arg His Leu Asn Met Thr Val
                325                 330                 335

Ala Glu Leu Phe Leu Asp Ile His Ala Ile Tyr Glu Glu Gln Gln Gly
            340                 345                 350

Ser Arg Asn Ser Lys Pro Asn Tyr Arg Arg Asn Pro Ser Asp Glu Lys
        355                 360                 365

Asn Asp Ser Arg Ser Tyr Thr Asn Thr Thr Lys Pro Lys Val Ile Ala
    370                 375                 380

Arg Asn Pro Gln Lys Thr Asn Asn Ser Lys Ser Lys Thr Ala Arg Ala
385                 390                 395                 400

His Asn Val Ser Thr Ser Asn Asn Ser Pro Ser Thr Asp Asn Asp Ser
                405                 410                 415

Ile Ser Lys Ser Thr Thr Glu Pro Ile Gln Leu Asn Asn Lys His Asp
```

```
            420                 425                 430

Leu His Leu Arg Pro Glu Thr Tyr Asp Ser Ile Ser Ser Leu Met Val
        435                 440                 445

Ser Lys Gly Glu Glu Leu Phe Thr Gly Val Val Pro Ile Leu Val Glu
    450                 455                 460

Leu Asp Gly Asp Val Asn Gly His Lys Phe Ser Val Ser Gly Glu Gly
465                 470                 475                 480

Glu Gly Asp Ala Thr Tyr Gly Lys Leu Thr Leu Lys Phe Ile Cys Thr
                485                 490                 495

Thr Gly Lys Leu Pro Val Pro Trp Pro Thr Leu Val Thr Thr Leu Thr
            500                 505                 510

Tyr Gly Val Gln Cys Phe Ser Arg Tyr Pro Asp His Met Lys Gln His
        515                 520                 525

Asp Phe Phe Lys Ser Ala Met Pro Glu Gly Tyr Val Gln Glu Arg Thr
    530                 535                 540

Ile Phe Phe Lys Asp Asp Gly Asn Tyr Lys Thr Arg Ala Glu Val Lys
545                 550                 555                 560

Phe Glu Gly Asp Thr Leu Val Asn Arg Ile Glu Leu Lys Gly Ile Asp
                565                 570                 575

Phe Lys Glu Asp Gly Asn Ile Leu Gly His Lys Leu Glu Tyr Asn Tyr
            580                 585                 590

Asn Ser His Asn Val Tyr Ile Met Ala Asp Lys Gln Lys Asn Gly Ile
        595                 600                 605

Lys Val Asn Phe Lys Ile Arg His Asn Ile Glu Asp Gly Ser Val Gln
    610                 615                 620

Leu Ala Asp His Tyr Gln Gln Asn Thr Pro Ile Gly Asp Gly Pro Val
625                 630                 635                 640

Leu Leu Pro Asp Asn His Tyr Leu Ser Thr Gln Ser Ala Leu Ser Lys
                645                 650                 655

Asp Pro Asn Glu Lys Arg Asp His Met Val Leu Leu Glu Phe Val Thr
            660                 665                 670

Ala Ala Gly Ile Thr Leu Gly Met Asp Glu Leu Tyr Lys
        675                 680                 685


<210> SEQ ID NO 43
<211> LENGTH: 3208
<212> TYPE: DNA
<213> ORGANISM: Artificial sequence
<220> FEATURE:
<223> OTHER INFORMATION: Lucifirase - EngGAG - 3MS2

<400> SEQUENCE: 43

atggaagacg ccaaaaacat aaagaaaggc ccggcgccat tctatccgct ggaagatgga      60

accgctggag agcaactgca taaggctatg aagagatacg ccctggttcc tggaacaatt     120

gcttttacag atgcacatat cgaggtggac atcacttacg ctgagtactt cgaaatgtcc     180

gttcggttgg cagaagctat gaaacgatat gggctgaata caaatcacag aatcgtcgta     240

tgcagtgaaa actctcttca attctttatg ccggtgttgg gcgcgttatt tatcggagtt     300

gcagttgcgc ccgcgaacga catttataat gaacgtgaat tgctcaacag tatgggcatt     360

tcgcagccta ccgtggtgtt cgtttccaaa aaggggttgc aaaaaatttt gaacgtgcaa     420

aaaaagctcc caatcatcca aaaaattatt atcatggatt ctaaaacgga ttaccaggga     480

tttcagtcga tgtacacgtt cgtcacatct catctacctc ccggttttaa tgaatacgat     540

tttgtgccag agtccttcga tagggacaag acaattgcac tgatcatgaa ctcctctgga     600
```

-continued

```
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc caggtatcag gcaaggatat   1020
gggctcactg agactacatc agctattctg attacacccg agggggatga taaaccgggc   1080
gcggtcggta aagttgttcc atttttgaa gcgaaggttg tggatctgga taccgggaaa   1140
acgctgggcg ttaatcaaag aggcgaactg tgtgtgagag gtcctatgat tatgtccggt   1200
tatgtaaaca atccggaagc gaccaacgcc ttgattgaca aggatggatg gctacattct   1260
ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gatcgccgtg taattctaga gtcggggcgg ccggccgctt   1680
cgagcagaca tgataagata cattgatgag tttggacaaa ccacaactag aatgcagcat   1740
atgccacagc agtgcatgat gacccaaaac caagccaatc catctggttg gtcattttac   1800
ggacacccat ctatgattcc gtatacacct tatcaaatgt cgcctatgta ctttccacct   1860
gggccacaat cacagtttcc gcagtatcca tcatcagttg gaacgcctct gagcactcca   1920
tcacctgagt caggtaatac atttactgat tcatcctcag cggactctga tatgacatcc   1980
actaaaaaat atgtcagacc accaccaatg ttaacctcac ctaatgactt tccaaattgg   2040
gttaaaacat acatcaaatt tttacaaaac tcgaatctcg gtggtattat tccgacagta   2100
aacggaaaac ccgtacgtcc gatcactgat gatgaactca ccttcttgta taacgctttt   2160
caaatatttg ctccctctca attcctacct acctgggtca aagacatcct atccgttgat   2220
tatacggata tcatgaaaat tctttccaaa agtattgaaa aaatgcaatc tgatacccaa   2280
gaggcaaacg acattgtgac cctggcaaat ttgcaatata atggcagtac acctgcagat   2340
gcatttgaaa caaaagtcac aaacattatc gacagactga acaataatgg cattcatatc   2400
aataacaagg tcgcatgtca attaattatg agaggtctat ctggcgaata taaattttta   2460
cgctacacac gtcatcgaca tctaaatatg acagtcgctg aactgttctt agatatccat   2520
gctatttatg aagaacaaca gggatcgaga aacagcaaac ctaattacag gagaaatccg   2580
agtgatgaga agaatgattc tcgcagctat acgaatacaa ccaaacccaa agttatagct   2640
cggaatcctc aaaaaacaaa taattcgaaa tcgaaaacag ccagggctca caatgtatcc   2700
acatctaata actctcccag cacggacaac gattccatca gtaaatcaac tactgaaccg   2760
attcaattga acaataagca cgaccttcat cttaggccag aaacttactg agcggccgct   2820
gtaattagtt atgtcacgct tacattcacg ccctccatat ccgtacacca tcagggtacg   2880
agctagccca tggcgtacac catcagggta cgacgagtag atctcgtaca ccatcagggt   2940
```

```
acggaatcgc tgacggtacc tttaatatag tgtgattttt aaaaactttc gaacaagaat   3000

cagtaatata atatatataa ttaataaaac taatggaatt tgtttaattg aacttgacac   3060

ccgagaagga aggagttaga caacctgaag tctaggtccc tatttatttt tttatagtta   3120

tgttagtatt aagaacgtta tttatatttc aaatttttct tttttttctg tacagacgcg   3180

tgtacgcatg taacattgcg gccgccct                                      3208
```

<210> SEQ ID NO 44
<211> LENGTH: 2822
<212> TYPE: DNA
<213> ORGANISM: Artificial sequence
<220> FEATURE:
<223> OTHER INFORMATION: Lucifirase - EndGAG

<400> SEQUENCE: 44

```
atggaagacg ccaaaaacat aaagaaaggc ccggcgccat tctatccgct ggaagatgga     60

accgctggag agcaactgca taaggctatg aagagatacg ccctggttcc tggaacaatt    120

gcttttacag atgcacatat cgaggtggac atcacttacg ctgagtactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgggcatt    360

tcgcagccta ccgtggtgtt cgtttccaaa aaggggttgc aaaaaatttt gaacgtgcaa    420

aaaaagctcc caatcatcca aaaaattatt atcatggatt ctaaaacgga ttaccaggga    480

tttcagtcga tgtacacgtt cgtcacatct catctacctc ccggttttaa tgaatacgat    540

tttgtgccag agtccttcga tagggacaag acaattgcac tgatcatgaa ctcctctgga    600

tctactggtc tgcctaaagg tgtcgctctg cctcatagaa ctgcctgcgt gagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttc tgaggagcct tcaggattac    840

aagattcaaa gtgcgctgct ggtgccaacc ctattctcct tcttcgccaa aagcactctg    900

attgacaaat acgatttatc taatttacac gaaattgctt ctggtggcgc tcccctctct    960

aaggaagtcg gggaagcggt tgccaagagg ttccatctgc caggtatcag gcaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcaaag aggcgaactg tgtgtgagag gtcctatgat tatgtccggt   1200

tatgtaaaca atccggaagc gaccaacgcc ttgattgaca aggatggatg gctacattct   1260

ggagacatag cttactggga cgaagacgaa cacttcttca tcgttgaccg cctgaagtct   1320

ctgattaagt acaaaggcta tcaggtggct cccgctgaat tggaatccat cttgctccaa   1380

caccccaaca tcttcgacgc aggtgtcgca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gatcgccgtg taattctaga gtcggggcgg ccggccgctt   1680
```

```
cgagcagaca tgataagata cattgatgag tttggacaaa ccacaactag aatgcagcat   1740

atgccacagc agtgcatgat gacccaaaac caagccaatc catctggttg gtcattttac   1800

ggacacccat ctatgattcc gtatacacct tatcaaatgt cgcctatgta ctttccacct   1860

gggccacaat cacagtttcc gcagtatcca tcatcagttg gaacgcctct gagcactcca   1920

tcacctgagt caggtaatac atttactgat tcatcctcag cggactctga tatgacatcc   1980

actaaaaaat atgtcagacc accaccaatg ttaacctcac ctaatgactt tccaaattgg   2040

gttaaaacat acatcaaatt tttacaaaac tcgaatctcg gtggtattat tccgacagta   2100

aacggaaaac ccgtacgtcc gatcactgat gatgaactca ccttcttgta taacgctttt   2160

caaatatttg ctccctctca attcctacct acctgggtca aagacatcct atccgttgat   2220

tatacggata tcatgaaaat tctttccaaa agtattgaaa aaatgcaatc tgatacccaa   2280

gaggcaaacg acattgtgac cctggcaaat ttgcaatata atggcagtac acctgcagat   2340

gcatttgaaa caaaagtcac aaacattatc gacagactga acaataatgg cattcatatc   2400

aataacaagg tcgcatgtca attaattatg agaggtctat ctggcgaata taaattttta   2460

cgctacacac gtcatcgaca tctaaatatg acagtcgctg aactgttctt agatatccat   2520

gctatttatg aagaacaaca gggatcgaga aacagcaaac ctaattacag gagaaatccg   2580

agtgatgaga agaatgattc tcgcagctat acgaatacaa ccaaacccaa agttatagct   2640

cggaatcctc aaaaaacaaa taattcgaaa tcgaaaacag ccagggctca caatgtatcc   2700

acatctaata actctcccag cacggacaac gattccatca gtaaatcaac tactgaaccg   2760

attcaattga acaataagca cgaccttcat cttaggccag aaacttactg agcggccgct   2820

gt                                                                  2822

<210> SEQ ID NO 45
<211> LENGTH: 63
<212> TYPE: DNA
<213> ORGANISM: Artificial sequence
<220> FEATURE:
<223> OTHER INFORMATION: DNA compliment to Luciferase

<400> SEQUENCE: 45

tccatcttcc agcggataga atggcgccgg gcctttcttt atgtttttgg cgtcttccat     60

aaa                                                                   63
```

PRODUCTION OF RNA BY YEASTS WITH RECOMBINANT PSEUDO-VIRAL PARTICLES

INCORPORATION BY REFERENCE

The text file named New SEQ, created on Jun. 14, 2023, and sized 81,714 bytes, which contains sequence ID listings, is herein expressly incorporated by reference.

TECHNICAL FIELD

The application relates to the production of RNA of interest, more particularly messenger RNA (mRNA) of interest or long non-coding RNA (lncRNA) of interest, by recombinant yeasts, more particularly by yeasts with recombinant pseudo-viral particles.

The application concerns these yeasts, as well as the pseudo-viral particles produced thereof.

The application also relates to means for their production, including nucleic acid vectors and kits, as well as medical applications, more particularly vaccine, anti-tumor, anti-infectious and pro-regenerative.

BACKGROUND

Different methods of producing RNA are known in the art. These methods comprise in vitro synthesis methods that use in particular RNA polymerases.

The production of RNA, in particular mRNA, which are competent for the translation into proteins in mammalian cells, poses the particular problem of post-transcriptional modifications such as the presence of a polyA tail at the 3' end, a 7-methylguanosine (m7G) cap at the 5' end, or even certain methylations of adenines and cytosines.

In vitro synthesis methods of the prior art, for example, propose placing cap analogs in the transcriptional mixture, such as m7G5'ppp5'G. In order to stimulate the incorporation of the dinucleotide at the beginning of the chain, the in vitro synthesis methods of the prior art also propose to reduce the concentration of guanosine triphosphate (GTP) in the transcriptional mixture relative to the other nucleoside triphosphates (NTPs), which decreases transcription efficiency. In addition, the cap analog can then be incorporated in both orientations resulting in 50% poorly capped RNA. These methods of in vitro synthesis of RNA are therefore not very effective.

Other in vitro synthesis methods propose to use a chimeric enzyme comprising the catalytic domains of an RNA triphosphatase, a guanylyltransferase, an N7-guanine methyltransferase, and a DNA-dependent RNA polymerase (cf. for example, WO 2011/128444 in the name of EUKARYS). These in vitro RNA synthesis methods nevertheless remain expensive.

RNA recombinant production methods have been further developed. For example, one method proposes using the machinery of the mitochondria, to make it an RNA production and storage unit (see for example WO 2010/084371 in the name of MITOPROD). The RNA thus produced do not, however, have a cap at the 5' end, which limits their medical applications.

The application provides means for producing RNA that do not have all the drawbacks of the prior art.

SUMMARY

The application relates to the production of RNA, more particularly messenger RNA (mRNA) or long non-coding RNA (lncRNA), by recombinant yeasts, more particularly by yeasts with recombinant pseudo-viral particles. Yeasts have been genetically engineered to produce recombinant virus-like particles that contain this RNA, and do not retro-transcribe this RNA or retro-integrate it into their genome.

The RNA thus produced can advantageously have a polyA tail at the 3' end and a 7-methylguanosine (m7G) cap at the 5' end. They may therefore be competent for possible translation into mammalian cells. In addition, RNA can be produced in relatively large amounts.

The demand concerns these yeasts, as well as the pseudo-viral particles that they produce.

The application also relates to means for their production, including nucleic acid vectors and kits, as well as medical applications, more particularly vaccine, anti-tumor and pro-regenerative.

Recombinant virus-like particles are produced from certain yeast Ty retrotransposon elements, but do not retro-transcribe the RNA they contain. The yeast Ty retrotransposon elements used comprise in particular:

- a Gag protein of a yeast Ty retrotransposon, as well as
- a fragment of the RNA which corresponds to this protein, in this case a fragment of this RNA which does not comprise the start codon of translation [start] of this RNA sequence.

This RNA fragment is not intended to be translated into protein in yeast: it serves as an addressing sequence, which guides the RNA (of interest) to the Gag protein, thereby forming a complex between this RNA and Gag protein. This complex takes the form of a particle, in this case a recombinant pseudo-viral particle, which is formed by the polymerization of the Gag protein, and in which the RNA is encapsulated.

The yeast Ty retrotransposon elements used do not comprise the Ty reverse transcription means. More particularly, they do not comprise the integrase means of Ty, or more generally the precursor protein means Pol of Ty.

BRIEF DESCRIPTION OF THE FIGURES

Some of the figures in the application are in color. The application as filed contains the color version of these figures, which can therefore be viewed by inspection of the application file as filed.

WT=wild *S. paradoxus*; ΔSpt21=*S. paradoxus* deleted for the Spt21 gene; ΔSrb2=*S. paradoxus* deleted for the Srb2 gene.

Figure 2A:
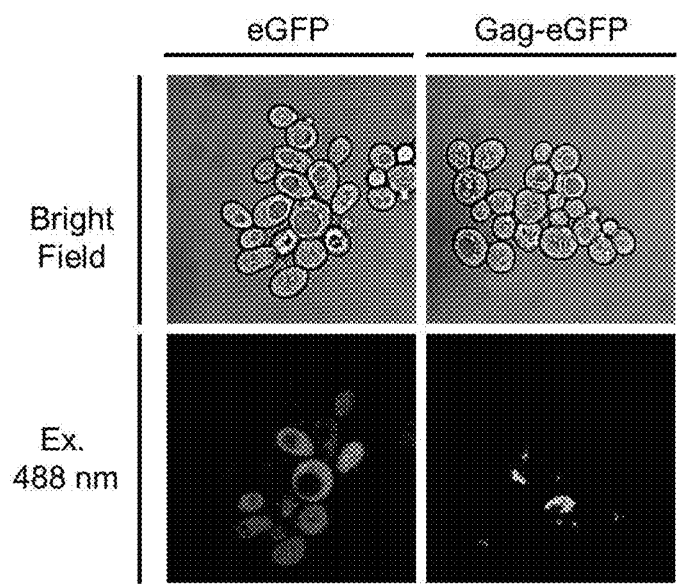

FIG. 2A illustrates the confocal fluorescence microscopy analyzes of eGFP expression and Gag-eGFP fusion protein in yeast *S. paradoxus*. eGFP=Enriched Green Fluorescent Protein; bright field=transmitted light exposure; Ex. 488 nm=exposure at 488 nm wavelength.

Figure 2B:
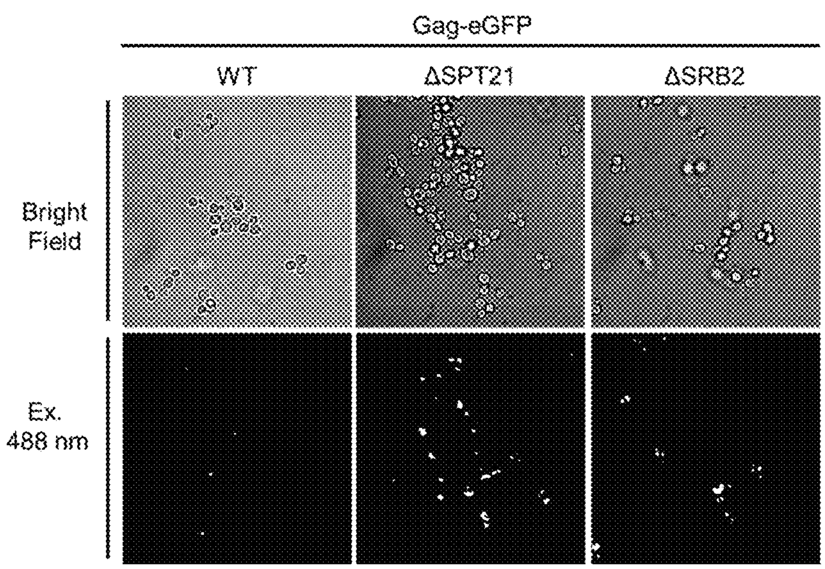

FIG. 2B illustrates the confocal fluorescence microscopy analyzes of the expression of the Gag-eGFP fusion protein in wild *S. paradoxus* yeast (WT), and the ΔSpt21 and ΔSrb2 transcriptional mutants.

WT=wild *S. paradoxus*; ΔSpt21=*S. paradoxus* deleted for the Spt21 gene; ΔSrb2=*S. paradoxus* deleted for the Srb2 gene.

Figure 2C:
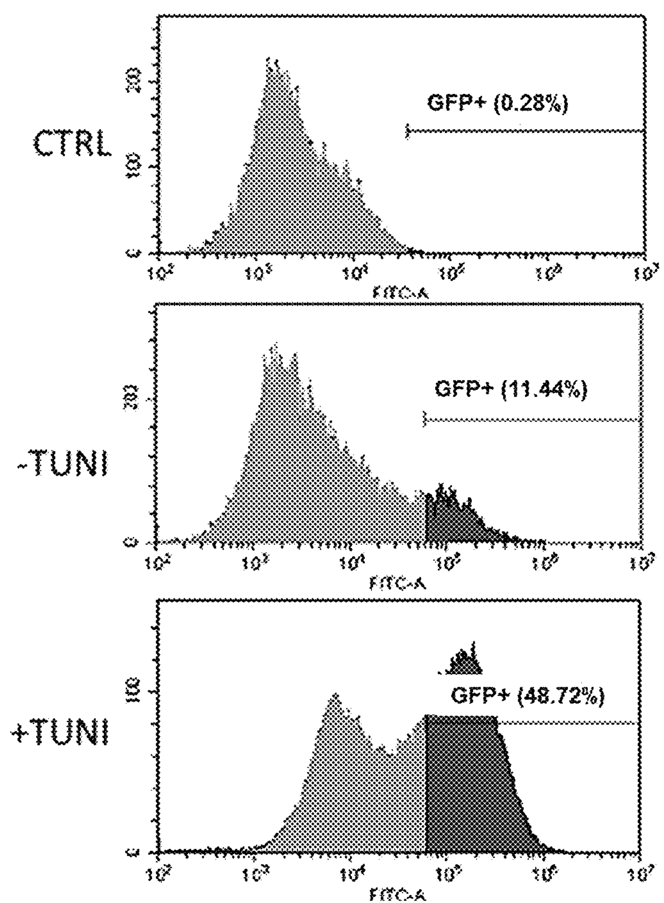

FIG. 2C illustrates the flow cytometric analysis of the expression of T-bodies eGFP (Gag-eGFP fusion protein) in the transcriptional mutant of *S. paradoxus* ΔSrb2 yeast after an 8 hours treatment at the tunicamycin (TUNI). T-bodies expression is under the control of a galactose inducible promoter. CTRL=control; −TUNI=without tunicamycin; +TUNI=with tunicamycin.

Figure 3A:
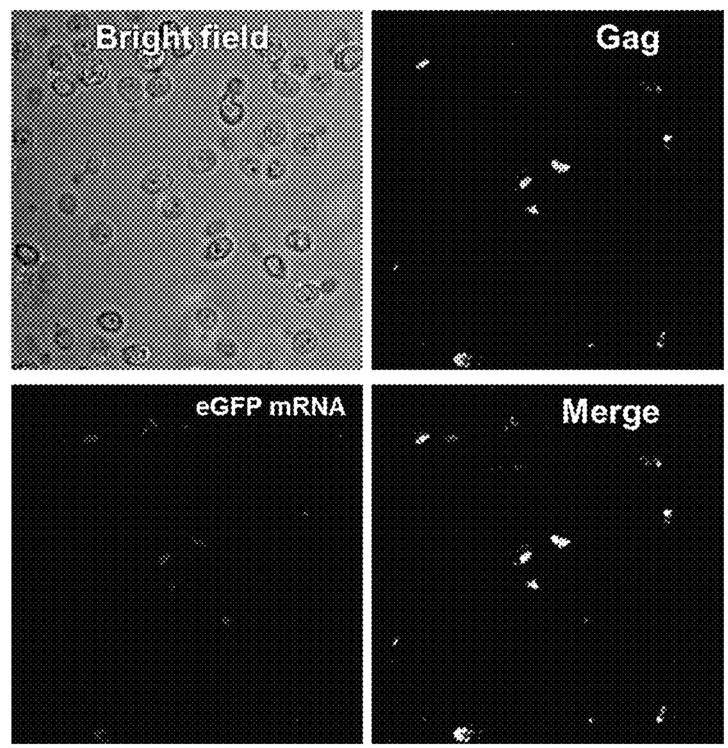

FIG. 3A: FIG. 3A illustrates FISH (fluorescence in situ hybridization) experiments for locating model mRNAs encoding the eGFP protein, by using primers addressing eGFP mRNA labeled with the Cy5 fluorophore on yeast *S. paradoxus* ΔSrb2 transformed with a Gag-eGFP fusion plasmid.

Bright field=transmitted light exposure; Merge=combination of images.

Figure 3B:
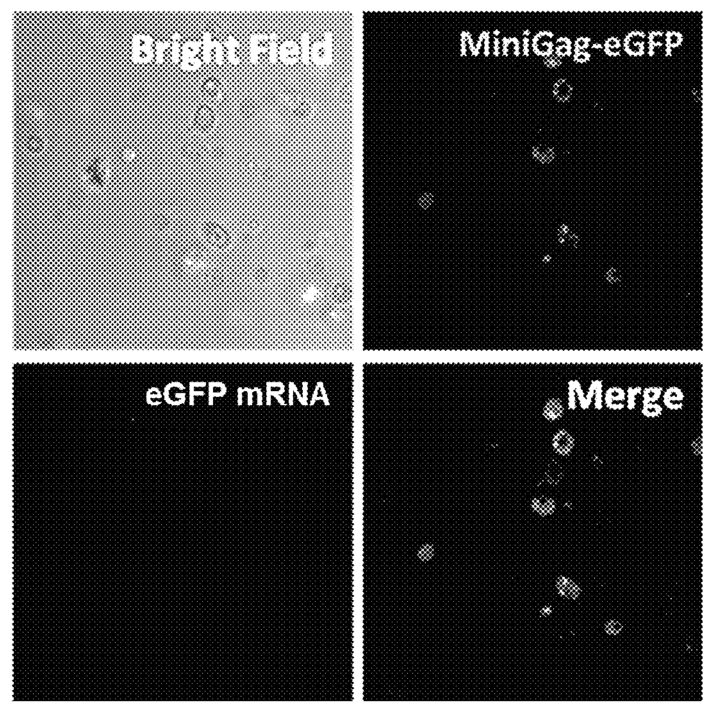

FIG. 3B: FIG. 3B illustrates FISH (fluorescence in situ hybridization) experiments for locating the mRNAs encoding the eGFP protein (mRNA models), by using primers addressing eGFP mRNA labeled with Cy5 fluophore on yeast *S. paradoxus* ΔSrb2 transformed with a MiniGag-eGFP fusion plasmid.

Bright field=transmitted light exposure; Merge=combination of images.

FIG. 4 illustrates the transmission electron microscopy image of T-bodies following the protein extraction by two different techniques (left: the pellet obtained by the method of lysis by the beads, on the right the pellet obtained by the method of sonication). The samples were stained with 2% uranyl acetate.

Figure 5A:
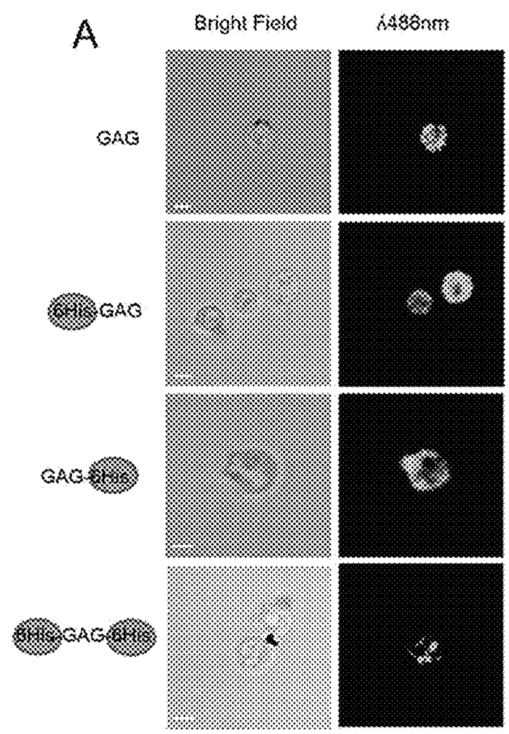

FIG. 5A illustrates the confocal fluorescence microscopy observation of T-bodies by immunofluorescence (anti-Ty1/GAG antibody) in the *S. paradoxus* ΔSrb2 yeast expressing the Gag protein, the 6His-Gag fusion protein, Gag-6His, 6His-Gag-6His. Bright field=transmitted light exposure; λ488 nm=exposure at a wavelength of 488 nm.

Figure 5B:
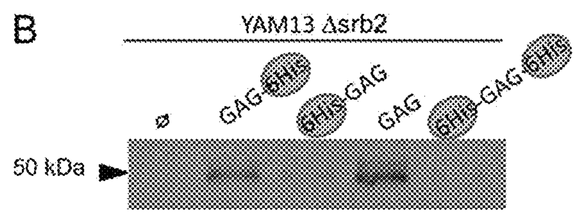

FIG. 5B illustrates the detection of the expression of the Gag protein by western blot (anti-Ty1/Gag antibody) in *S. paradoxus* ΔSrb2 yeast expressing the Gag protein, the 6His-Gag fusion protein, Gag-6His, 6His-Gag-6His. YAM13 ΔSrb2=*S. paradoxus* YAM13 yeast strain deleted for the Srb2 gene.

Figure 5C:
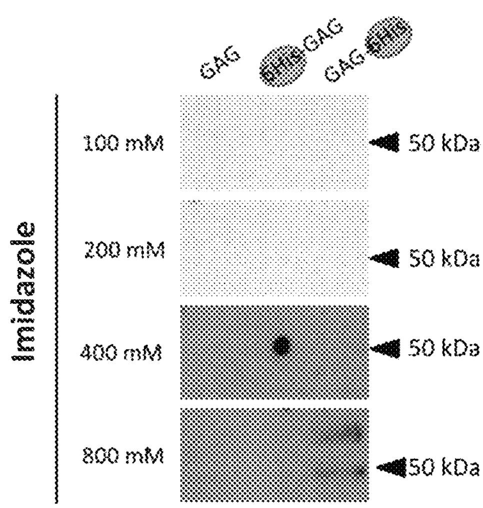

FIG. 5C illustrates western blot analysis (anti-Ty1/GAG antibody) of fractions eluted with imidazole increasing concentration buffers (100 mM, 200 mM, 400 mM, 800 mM). These fractions correspond to the T-bodies extracted from yeast strains expressing Gag, 6His-Gag and Gag-6His and then purified on a column loaded with nickel.

Figure 6A:
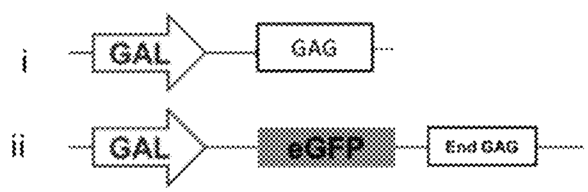

FIG. 6A is a schematic representation of transformed constructs in yeast *S. paradoxus* A Srb2. The first construction is responsible for the formation of T-bodies (i), the second is a plasmid allowing the transcription of an eGFP RNA having a "EndGAG" sequence at the 3' end allowing the addressing of RNA within the T-bodies (ii).

GAL=galactose promoter; EndGAG=mini-GAG (=sequence of addressing to the retro some).

Figure 6B:
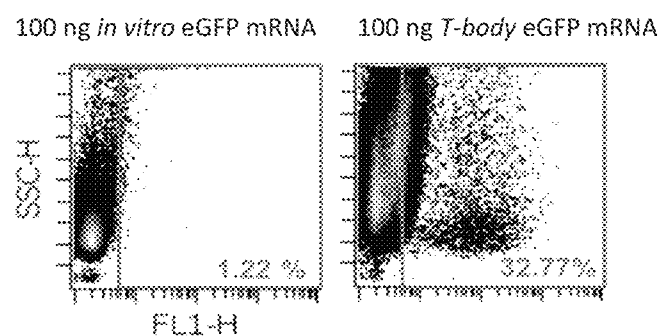

FIG. 6B illustrates the flow cytometric analysis of mouse dendritic cells (DC2.4 line) expressing eGFP after 24 hours of transfection using an eGFP RNA that is produced by in vitro transcription (FIG. left) is produced from T-bodies and vectorized with cationic liposomes (Lip100).

SSC−H=diffraction height of light; FL1−H=intensity measured in green.

Figures 7A, 7B:
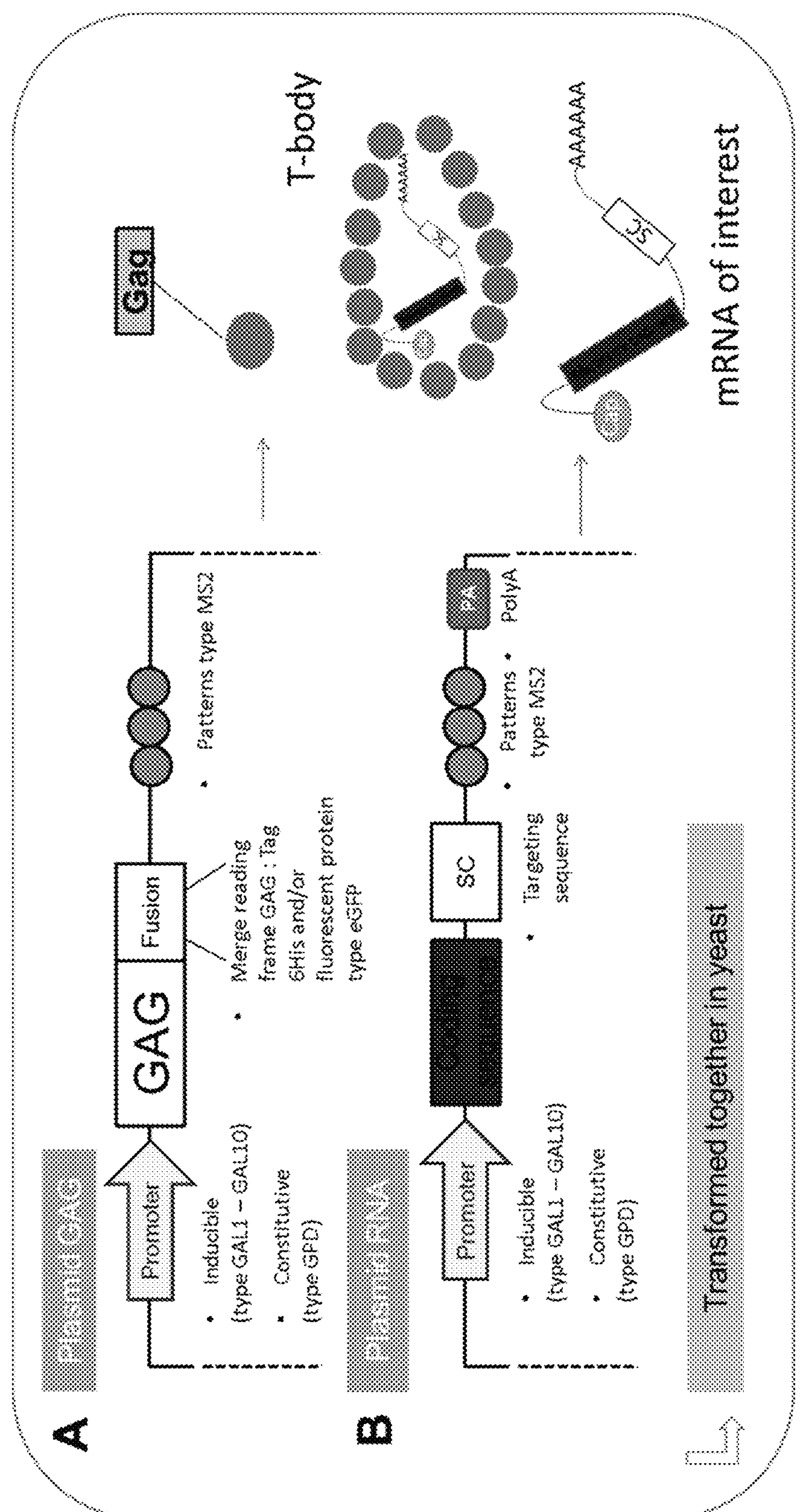
Figure 7C:
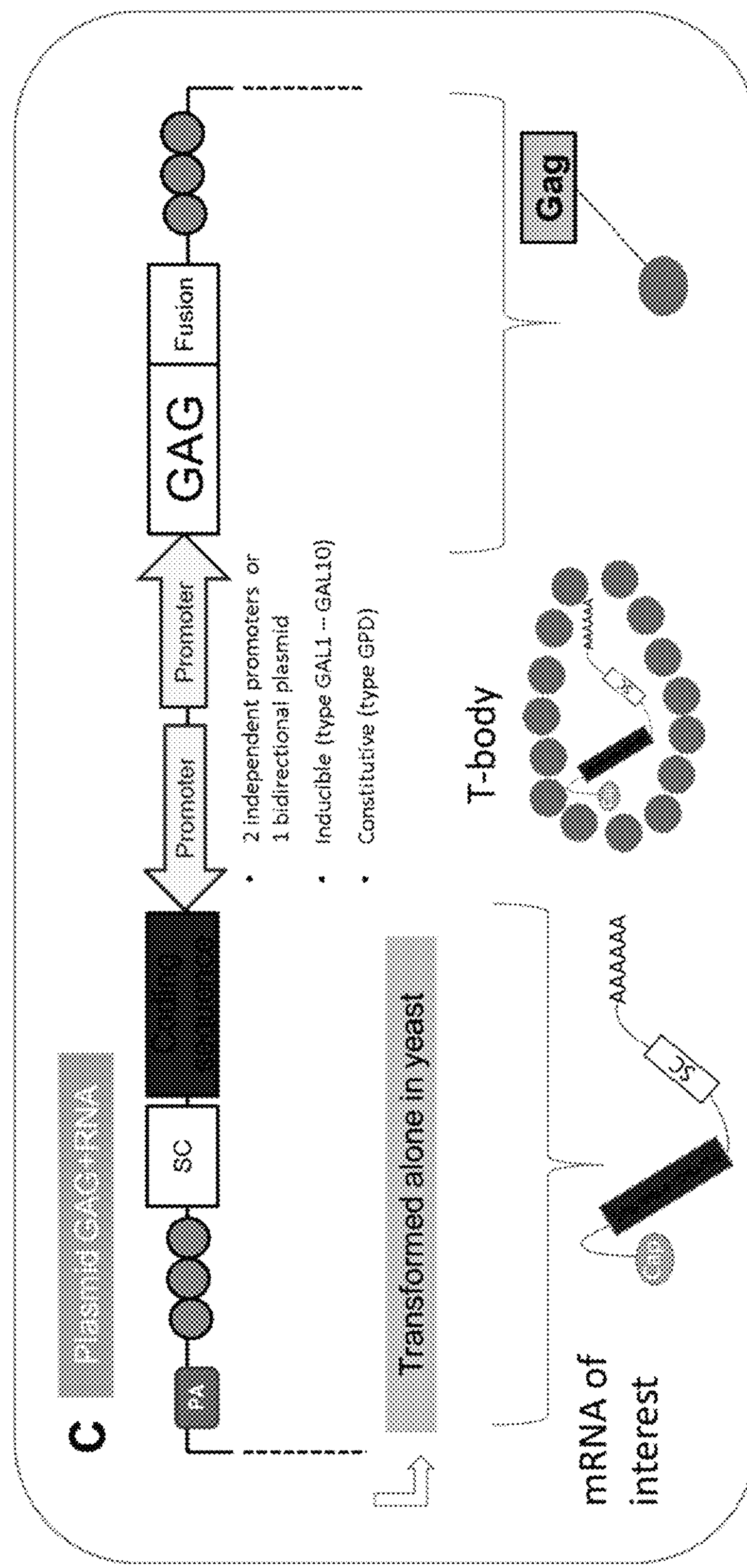

FIGS. 7A, 7B and 7C: The figures are a schematic representation of the plasmids necessary for the formation of T-bodies loaded with (m)RNA of interest used to modify the Ty-negative yeast strain (*S. paradoxus* for example). The GAG plasmid (FIG. 7A) and the RNA plasmid (FIG. 7B) are used together to transform the Ty-negative yeast strain. The sequence coding for the Gag protein (FIG. 7A) may optionally be linked to a sequence encoding a purification tag (poly-histidine tag or 6His tag), or a detection tag (for example the eGFP fluorescent protein). MS2=sequence of bacteriophage MS2 (purification label).

The expression of the two plasmids allows the synthesis of the Gag protein and the (m)RNA of interest. The SC signal sequence on the RNA plasmid is a retrosomal addressing sequence that allows the formation of the mRNA/Gag protein complex, which is called the T retrosome (or T-body). This retrosomal addressing sequence may for example be a GAG sequence modified to no longer encode the Gag protein, in particular by deleting the transcription start codon [start] at the beginning of the sequence («miniGag» or «End Gag» sequence).

The plasmid GAG+RNA (FIG. 7C) allows both the synthesis of the Gag protein and the mRNA of interest.

Figure 8:
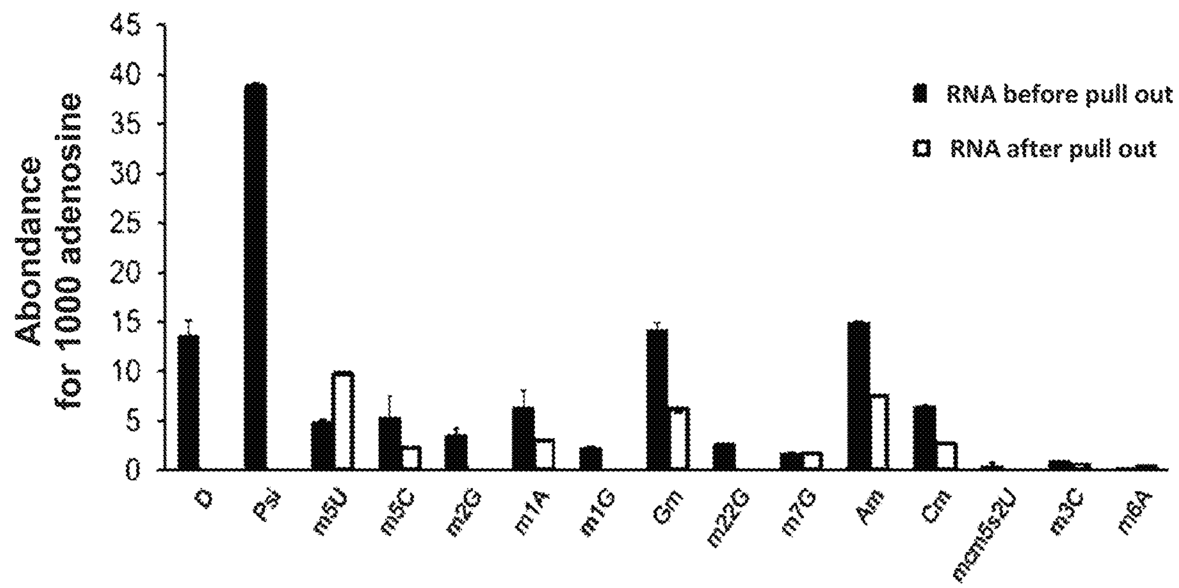

FIG. 8 illustrates the mass spectrometric study of the chemical changes present at the level of messenger RNA bioproduced. This technique is based on mass spectrometry (LC-MS) analysis of the fragments obtained after complete RNase T1 hydrolysis of the RNA studied. The bars of black histograms (RNA before «pull out») correspond to the average of 2 samples of RNAs extracted from T-bodies resulting from mechanical lysis. The white histogram bars (RNA after «pull out») correspond to the average of 2 samples of RNAs extracted from T-bodies resulting from a mechanical lysis followed by a «pull out» protocol allowing the exclusive purification of the RNA of interest.

Figure 9:
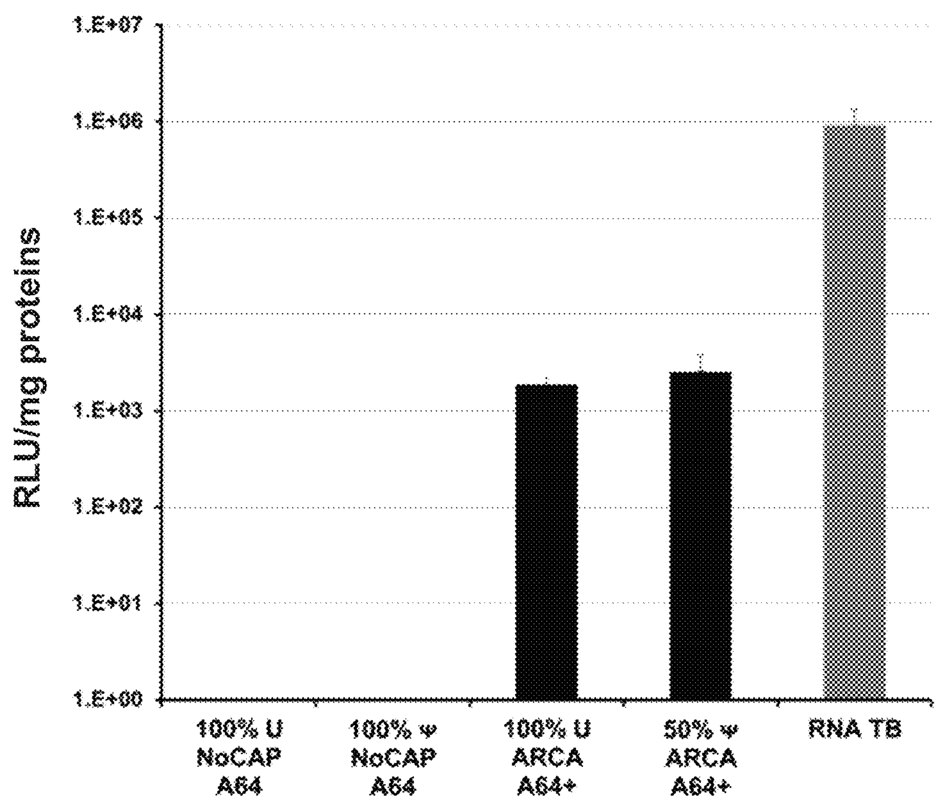

FIG. 9 illustrates the measurement of luciferase activity (RLU/mg protein) on DC2.4 cells after 20 h of transfection with 50 ng of RNA Luciferase produced in vitro (black bar) and bioproduced (RNA TB, bar gray) vectorized with Lipofectamine Messenger Max (LFM). RNAs synthesized in vitro:

have not undergone modifications: U=uridine; NoCAP=no cap and A64=no additional polyadenylation reaction; or have undergone modifications: ARC A=addition of an ARC A cap; ψ=incorporation of 50 to 100% of pseudouridine residues and A64+=additional polyadenylation reaction.

ABBREVATIONS

D=dihydrouridine; Psi=pseudouridine; m5U=5-methyluridine; m5C=5-methylcytidine; m2G=N2-methylguanosine; mlA=1-methyladenosine; m1G=1-methylguanosine; Gm=2'-O-methylguanosine; m22G=N2, N2-dimethylguanosine; m7G=7-methylguanosine; Am=2'-O-methyladenosine; Cm=2'-O-methylcytidine; mcm5s2U=5-methoxycarbonylmethyl-2-thiouridine; m3C=3-methylcytidine and m6A=N6-methyladenosine.

DETAILED DESCRIPTION

The application describes the objects defined in the claims as filed, the objects described below and the objects illustrated in part «examples».

The application relates in particular to a method for producing (recombinant) RNA, to a method for producing a pharmaceutical composition, and to products that may be used or produced in these methodes, in particular nucleic acids (more particularly nucleic acid vectors, such as plasmids), kits, recombinant bacteria cells, recombinant yeast cells, as well as recombinant pseudo-viral complexes, granules or particles.

The application implements some Ty retrotransposon elements of yeast (but not all elements of this retrotransposon). It implements in particular yeast genetic modification means, which derive from the Gag protein of a yeast Ty retrotransposon and the RNA of this protein. However, the application does not implement the reverse transcript Ty reverse transcription means.

The application makes it possible in particular to produce RNAs, especially messenger RNAs (mRNAs) or long non-coding RNAs (lncRNAs), which have a polyA tail at the 3' end and/or a 7-methylguanosine (m7G) cap at the 5' end, or even methylation of adenine and/or cytosine and/or pseudouridine residue (s). The means of demand also make it possible to produce these RNAs in a relatively large amount, and at a reduced cost. The means of the request therefore make it possible to clinically access the medical applications of RNAs (such as mRNA and lncRNA), particularly in the field of immunotherapy and gene therapy.

The application is thus related to a method for (recombinant) RNA production, said method comprising:

culturing yeast cells, which have been genetically modified to produce this RNA, and collecting this RNA.

This RNA advantageously comprises an addressing sequence, namely a sequence which enables it to be addressed to a Gag protein of a yeast Ty retrotransposon. In addition to the addressing sequence, the RNA may in particular comprise at least one RNA of interest, such as at least one prokaryotic RNA (especially bacteria), viruses (especially Zika or Influenza), or eukaryotic, in particular of eukaryote other than yeast (for example of human), and/or at least one artificial or non-natural RNA (for example an RNA whose translation is a sequence which comprises various epitopes of viruses and/or bacteria), This RNA can advantageously be an mRNA or a lncRNA, more particularly an mRNA.

This RNA can be a yeast-heterologous RNA that produces it, or even a heterologous yeast in general.

The genetic modifications that have been made to the yeast cells to produce this RNA comprise in particular the transfer into these yeast cells (in particular by transfection or transformation) of a nucleic acid construct which codes for a Gag protein of a yeast Ty retrotransposon.

Alternatively or additionally, and more particularly additionally, the genetic modifications that have been made to the yeast cells to produce this RNA comprise in particular the transfer into these yeast cells (in particular by transfection or transformation) of a nucleic acid construct whose transcript ARN comprises:

said addressing sequence and/or the RNA sequence of interest, more particularly whose RNA transcript comprises at least said addressing sequence, more particularly whose RNA transcript comprises the sequence of an RNA of interest linked to the addressing sequence which addresses (or guides) this RNA to a Gag protein of a yeast Ty retrotransposon.

RNA (more particularly mRNA or lncRNA) is produced by yeast cells with a Gag protein of a yeast Ty retrotransposon, in the form of a structure that can be described as complex, granule or pseudo-viral particle.

One or more different RNAs can thus be produced.

The, or at least one, of the transferred nucleic acid construct (s) may be integrated into the genome, or may not be integrated into the genome but may be present in the nucleus or cytoplasm, for example as an episome.

For example, a nucleic acid construct that encodes the yeast Ty retrotransposon Gag protein can be integrated into the yeast genome, while the nucleic acid construct of which the RNA transcript comprises said addressing sequence and/or the RNA sequence of interest, may not be integrated into the chromosome (but be present in the nucleus and/or the cytoplasm, especially in the form of an episome).

Alternatively, there may be only one construct that contains the two nucleic acids (nucleic acid encoding Gag, and nucleic acid whose RNA transcript comprises said addressing sequence and/or the RNA sequence of interest) and this construct may be integrated into the yeast genome, or may be present in the nucleus or cytoplasm (e.g. as an episome).

The application is thus related to a method for producing RNA (more particularly mRNA or lncRNA) of interest, said method comprising:

culturing yeast cells, which have been genetically modified to produce pseudo-viral (recombinant) particles which comprise an RNA whose sequence comprises said addressing sequence and/or the RNA of interest, more particularly which comprises said addressing sequence linked to said RNA of interest, and collecting the RNA which is contained in the pseudo-viral (recombinant) particles thus formed.

The term prokaryotic is understood according to its usual meaning in the field. It relates more particularly to a bacteria, especially a bacteria with potential infectious and/or pathogenic for the human species.

The term virus is understood according to its usual meaning in the field. It relates more particularly to a virus, in particular a virus with potential infectious and/or pathogenic for the human species, in particular Zika or Influenza.

The term eukaryotic is understood according to its usual meaning in the field. When it relates to the RNA, the mRNA or the mRNA of the application, it relates more particularly to a eukaryotic other than yeast, more particularly a multicellular eukaryote such as a mammal (more particularly a human or a non-human mammal), more particularly a human.

The term Ty is understood according to its usual meaning in the field. It relates more particularly to a Ty1, Ty2, Ty3, Ty4 or Ty5 retrotransposon, more particularly a Ty1, Ty2 or Ty3 retrotransposon, more particularly a Ty1 retrotransposon.

The term yeast is understood according to its usual meaning in the field.

It relates more particularly to a yeast of the genus *Saccharomyces* or the genus *Pichia*, more particularly of the genus *Saccharomyces*.

Among the yeasts of the genus *Saccharomyces*, the species *paradoxus* and *cerevisiae*, in particular the species *paradoxus*, are more particularly targeted.

Among the yeasts of the genus *Pichia*, the species *P. pastoris* is particularly targeted. An example of *S. paradoxus* strain is the strain that is accessible from ATCC under the number 76528™. ATCC® is the American Type Culture Collection (10801 University Blvd.; Manassas, Virginia 20110-2209; USA.).

An example of *S. cerevisiae* strain is strain YAM510, which does not contain functional Ty1 retrotransposon, and which has been described in Rothstein et al. 1983 and Thomas et al. 1989.

In addition to having been genetically modified to produce virus-like (recombinant) particles, the yeast cells of the application are yeast cells which:

is naturally devoid of Ty1 retrotransposon, or which is naturally provided with Ty1 retrotransposon, but whose Ty1 retrotransposon sequence has been modified so as not to produce or be deficient in the T retrosome. Alternatively or additionally, the yeast can be free of Ty2 and Ty3 retrotransposon, or else (naturally provided with but) was genetically modified to not produce a T-retrosome that would be encoded by a Ty2 or Ty3 retrotransposon.

Alternatively or additionally, the yeast can be devoid of Ty2, Ty3, Ty4 and Ty5 retrotransposon, or (although it is naturally provided with it) has been genetically modified so as not to produce a T retrosome which would be encoded by a Ty2, Ty3, Ty4 or Ty5 retrotransposon.

Advantageously, the yeast is a yeast which is (naturally) devoid of retro-transposon Ty, or is a yeast which is naturally provided in one or more retro-transposon Ty but whose sequence of these or these retro-transposons Ty has been genetically modified so as not to produce a T-retrosome.

Advantageously, the yeast is devoid of retro-transposon Ty, or has been genetically modified so as not to produce a T-retrosome.

The fact of using a yeast which is devoid of this (these) retrotransposon(s) Ty, or which does not produce this (these) Ty retrosome (s), makes it possible in particular to limit or avoid that the RNA (mRNA or lncRNA) produced is retrotransposed (into cDNA) (and thus to limit or avoid the «loss» of mRNA or lncRNA by unwanted cDNA backtranscription).

The yeast *Saccharomyces paradoxus* is an example of yeast which is naturally devoid of Ty retrotransposon, in particular Ty1 retrotransposon. *S. paradoxus* can therefore be directly implemented for the transfer of nucleic acids from i. and/or ii. The yeast *Pichia pastoris* is a yeast which is naturally free of Ty retrotransposon, and can therefore be directly used for transferring nucleic acids from i. and/or ii.

The yeast *Saccharomyces cerevisiae* is an example of yeast which is naturally provided with Ty retrotransposons, in particular a Ty1 retrotransposon. It must therefore be genetically modified so as not to produce a Ty retrosome, in particular a Ty1 retrosome.

A genetic modification that makes it possible not to produce Ty retrosome (s) may, for example, comprise the deletion (in the chromosome of the yeast) of the expression promoter of the Ty retrotransposon (s), and/or a mutation of this chromosome (by deletion and/or replacement and/or insertion of one or more nucleotides) interrupting at least one of the open reading frames of the Ty retrotransposon (s).

In accordance with the application, the genetic modifications made to the yeast cells for producing said pseudo-viral (recombinant) particles comprise transfection or transformation of these yeast cells by:

i. a nucleic acid comprising a first nucleotide sequence, and/or, preferably and, ii. a nucleic acid comprising a second nucleotide sequence, wherein:

the first nucleotide sequence comprises or is a DNA sequence which encodes the expression of the Gag protein of a yeast Ty retrotransposon, the second nucleotide sequence comprises or is a DNA sequence whose RNA transcript comprises:

a. the sequence of said RNA (mRNA or lncRNA) of interest, and/or b. said addressing sequence, more particularly whose RNA transcript comprises at least said addressing sequence, more particularly whose RNA transcript comprises:

a. the sequence of said RNA (mRNA or lncRNA) of interest, linked to b. said addressing sequence.

The nucleic acid of i. may for example be in the form of episomes that replicate autonomously or be integrated with the chromosomes of the yeast.

The nucleic acid of ii. may for example be in the form of episomes that replicate autonomously or be integrated with the chromosomes of the yeast.

The nucleic acid of i. code the expression of the Gag protein which will form the pseudo-viral particle, or be comprised in the protein polymer which forms this particle (cf. FIGS. 7A, 7B and 7C).

The nucleic acid of ii. «encodes» the transcription of the RNA which contains the RNA of interest to be produced, linked to an addressing RNA sequence which guides this RNA of interest towards the Gag protein of the pseudo-viral particle in formation (cf. FIGS. 7A, 7B and 7C).

The combination of nucleic acids of i. and ii. thus produces a pseudo-viral particle containing the RNA of interest (for example an mRNA or lncRNA) (cf. FIGS. 7A, 7B and 7C).

The nucleic acid of ii. (or each of the sequences it contains) is therefore intended to be transcribed into RNA in yeast, but it is not particularly intended to be translated into protein. The nucleic acid of ii. (or each of the sequences it contains) can therefore be a sequence which, in a yeast, cannot be translated into protein (or polypeptide). On the other hand, the RNA thus transcribed and produced in the yeast cell may be an RNA which encodes the expression of a protein (or a polypeptide) in a mammalian cell (for example an RNA which encodes expression of one or more antigens in a mammalian cell).

The Gag protein may especially be:

that of the Ty 1 retrotransposon of *S. cerevisiae*, that is to say the protein of sequence SEQ ID NO: 3, or a sequence which is at least 90% identical to the sequence of SEQ ID NO: 3 [the percentage of identity being calculated over the longest of the two sequences].

For example, the Gag protein may in particular be a Gag protein of another yeast retrotransposon other than the Ty1 retrotransposon of *S. cerevisiae* (retrotransposon of *S. cerevisiae* other than Ty1, and/or retrotransposon of yeast other than *S. cerevisiae*, for example yeast Ty1 retrotransposon other than *S. cerevisiae*), the sequence of which is at least 90% identical to the sequence of SEQ ID NO: 3.

The Gag protein of a yeast Ty retrotransposon may thus be in particular a protein whose sequence is the sequence of SEQ ID NO: 3 or a sequence which is at least 90% (more particularly at least 95%) identical to the sequence of SEQ ID NO: 3, and which is a Gag protein of a yeast Ty1, Ty2 or Ty3 retrotransposon.

In the second nucleotide sequence, the "b. sequence" has the particular function of addressing the "a. sequence" (in this case, the RNA of interest) to the Ty retrotransposon Gag protein which is produced by the first nucleotide sequence, more particularly to address it to a protein polymer containing this Gag protein which is synthesized in the yeast cell genetically modified.

The second nucleotide sequence is intended to be transcribed into RNA, but it is not particularly intended to be translated into protein in yeast. It is indeed in RNA form that it carries out its addressing or guide function. The second nucleotide sequence may therefore be advantageously devoid of a reading frame whose first codon would be the start codon of translation [start] (ATG). Advantageously, the addressing sequence or "b. sequence" comprises a fragment of the RNA sequence whose translation into amino acids is the sequence of said Gag protein of a yeast Ty retrotransposon.

This fragment may comprise a fragment of at least 150 nucleotides, more particularly at least 200 nucleotides, more particularly at least 250 nucleotides, more particularly at least 300 nucleotides, more particularly at least 350 nucleotides, more particularly at least 398 nucleotides, more particularly at least 500 nucleotides, more particularly at least 1000 nucleotides, more particularly at least 1078 nucleotides. In what follows, the expression «at least 150 nucleotides» explicitly comprises each of the upper thresholds that are above indicated (at least 200 nucleotides, etc.).

This fragment can in particular be the fragment of an RNA sequence whose translation into amino acids would be:

- the sequence of the Gag protein of a yeast Ty retrotransposon of *S. cerevisiae*, namely the protein of SEQ ID NO: 3, or
- the sequence of the Gag protein of another retrotransposon of yeast (retrotransposon other than Ty1, for example Ty2 or Ty3, and/or yeast other than *S. cerevisiae*) which is at least 90% identical with the sequence of SEQ ID NO: 3 (the percentage of identity being calculated over the length of the longest of the two sequences).

This fragment of at least 150 nucleotides can in particular comprise or be:

- the sequence of SEQ ID NO: 16 (398 nucleotides), or
- a (sub) fragment of at least 150 nucleotides of the sequence of SEQ ID NO: 16.

For example, the fragment may comprise:

- the sequence of SEQ ID NO: 18 (1078 nucleotides), or
- a sequence which is at least 90% identical with the sequence of SEQ ID NO: 18 (and which comprises a fragment of at least 150 nucleotides of the RNA sequence whose amino acid translation is the sequence of said Gag protein of yeast Ty retrotransposon, more particularly which comprises the sequence of SEQ ID NO: 16 or a (sub) fragment of at least 150 nucleotides of the sequence of SEQ ID NO: 16) [the percentage of identity being calculated on the basis of length of the longest of the two sequences].

Advantageously, the "b. sequence" does not comprise the [start] translation start codon (AUG) of the RNA sequence of said Gag protein of yeast Ty retrotransposon. In the RNA sequence whose translation would be the sequence of SEQ ID NO: 3 (*S. cerevisiae* Ty1 Gag protein), this start codon is the AUG codon which is the transcript of the ATG codon at the 1-3 positions of the sequence SEQ ID NO: 2. This translation start codon may be deleted, or may be mutated to a codon other than «start», for example a stop codon (UAA, UAG or AGA).

More generally, the RNA fragment that is comprised in said b. addressing sequence and which is a fragment of the RNA sequence whose translation into amino acids would be the sequence of said Gag protein of a yeast Ty retrotransposon, does not advantageously comprise a reading frame whose first codon would be a translation start codon (AUG). More generally, this RNA fragment does not comprise a reading frame which, in a yeast, would be an open reading frame (this sequence is intended to be transcribed into RNA in yeast, but it is not particularly intended to be translated into protein).

More generally, the b. addressing sequence advantageously does not comprise a reading frame whose first codon would be the translation start codon (AUG). More generally, it does not comprise a reading frame which, in a yeast, would be an open reading frame (this sequence is intended to be transcribed into RNA in yeast, but it is not particularly intended to be translated into protein).

For example, the "b. sequence" can be or comprises:

- the sequence of SEQ ID NO: 14 or
- a sequence which is at least 90% identical to the sequence of SEQ ID NO: 14 (and which comprises a fragment of at least 150 nucleotides of the RNA sequence whose amino acid translation would be the sequence of said Gag protein of yeast Ty retrotransposon, more particularly which comprises the sequence of SEQ ID NO: 16 or a (sub) fragment of at least 150 nucleotides of the sequence of SEQ ID NO: 16) [the percentage of identity being calculated on the basis of length of the longest of the two sequences], without comprising the start codon (AUG) of the RNA sequence of said Gag protein of yeast Ty retrotransposon, more generally without including a reading frame whose first codon would be an AUG translation start codon, more generally without including a frame open reading.

Complementarily to the absence of this translation start codon, the "b. sequence" may comprise one or more stop codons (UAA, UAG, or AGA) in at least one, if not all, of the three reading frames.

More generally, the second nucleotide sequence advantageously does not comprise a reading frame whose first codon would be the translation start codon [ATG], more generally it does not comprise a reading frame which, in a yeast, would be an open frame of reading (this sequence is intended to be transcribed into RNA in yeast, but it is not particularly intended to be translated into protein).

Advantageously, the nucleic acid of ii. does not comprise a DNA sequence that encodes a complete RNA sequence of said Gag protein of a yeast Ty retrotransposon.

The nucleic acid of i. and the nucleic acid of ii. encode the formation, in (the cytoplasm of said) yeast cells, of complexes which comprise:

- (a protein polymer that comprises) the Gag protein translated from the first nucleotide sequence and
- the RNA (mRNA or lncRNA) transcribed from the second nucleotide sequence.

More particularly, the nucleic acid of i. and the nucleic acid of ii. encode the formation, in (the cytoplasm of said) yeast cells, of granules (recombinants) or virus-like particles (VLPs or VLPs) (recombinant) which:

- are formed by (a protein polymer which comprises) the Gag protein translated from the first nucleotide sequence, and
- encapsulate the RNA (mRNA or lncRNA), transcribed from the second nucleotide sequence.

The term «encode» (and its grammatical equivalents) is understood in its usual meaning in the field. This term is applied both to the expression of a DNA sequence in protein, that is to say its transcription and its translation (DNA codons transcribed in RNA codons, then translated into amino acids according to the universal genetic code, and taking due account of the degeneracy of this code).

For simplicity, this term can here also be applied to the (simple) transcription of a DNA sequence in RNA sequence (for example, nucleotides A, T, G and C transcribed in nucleotides A, U, G and C, respectively), or the (simple) translation of an RNA sequence into amino acids (according to the universal genetic code, and with due regard to the degeneracy of this code). The expression «code the expression» or «code transcription» may be understood by the person skilled in the art as implying the presence in the DNA sequence of sequence (s) allowing to induce, in particular to initiate, transcription, by example the presence of the sequence of (at least) a promoter.

The first nucleotide sequence thus advantageously comprises a DNA sequence (or cDNA, or gDNA) which is the coding sequence [CDS] of the open reading frame of the Gag protein of a yeast Ty retrotransposon, under the control of a promoter for the expression of this open framework.

The DNA sequence of the second nucleotide sequence advantageously comprises a DNA sequence which is the retro-transcript of an RNA sequence which comprises the RNA (mRNA or lncRNA) of interest, under the control of a promoter for the transcription of this DNA (but preferably without comprising reading frame, which, in a yeast, would be an open reading frame).

Advantageously, the nucleic acid of i. and the nucleic acid of ii. are nucleic acid vectors, more particularly nucleic acid vectors adapted to the transfer of nucleic acids into yeast cells, for example suitable for transfection or transformation of these yeast cells. Nucleic acid i. and the nucleic acid of ii. can (each independently of each other) be or not be integrative (that is to say, be or not be intended to integrate with the chromosome of the cell that receives them in transfer).

The term «nucleic acid vector» is intended in accordance with its usual meaning in the art. It relates more particularly to a plasmid, more particularly a replicative plasmid or an episomal plasmid. Thus, the nucleic acid of i. and the nucleic acid of ii. may each independently of one another be plasmids, especially episomal plasmids or replicative plasmids.

The nucleic acid of i. may for example be a nucleic acid vector, in particular a plasmid (episomal or non-integrative), which comprises the first insert nucleotide sequence for its transcription and its translation into a yeast cell.

The nucleic acid of ii. may for example be a nucleic acid vector, in particular a plasmid (episomal or non-integrative), which comprises the second insert nucleotide sequence for its transcription in a yeast cell. For example, the nucleic acid of i. is an episomal plasmid, while the nucleic acid of ii. is a non-integrative plasmid, more particularly a replicative vector.

The nucleic acid of i. and the nucleic acid of ii. can be a single molecule, or be two distinct or separate molecules. For example, the nucleic acid of i. and the nucleic acid of ii. can be a single nucleic acid vector, in particular a single plasmid, or be two distinct or distinct nucleic acid vectors, in particular two distinct or separate plasmids.

Advantageously, the nucleic acid of i. and the nucleic acid of ii. are each (independently of each other) present in multiple copies. Advantageously, the number of copies of the nucleic acid of ii. is greater (for example 2, 3, 4, 5 or 6 times greater) than the number of copies of the nucleic acid of i. The first nucleotide sequence can be integrated into the yeast genome that has received the nucleic acid of i. in transfer, or not to be integrated.

The second nucleotide sequence can be integrated into the genome of the yeast that has received the nucleic acid of ii. in transfer, or not to be integrated.

For example, the first nucleotide sequence is integrated into the genome of the yeast, and the second nucleotide sequence is not integrated (but is present in the nucleus and/or cytoplasm, for example by being comprised in the nucleic acid of the yeast. ii.).

Thus, according to the application, the genetic modifications made to the yeast cells for producing said pseudo-viral (recombinant) particles comprise the insertion into these yeast cells (for example by transfection or transformation) of:

i. a nucleic acid comprising a first nucleotide sequence, and/or, preferably and, ii. a nucleic acid comprising a second nucleotide sequence, wherein:

- the nucleic acid of i. and the nucleic acid of ii. are one and the same molecule, or two distinct or separate molecules,
- the first nucleotide sequence comprises or is a DNA sequence which encodes the expression of the Gag protein of a yeast Ty retrotransposon;
- the second nucleotide sequence comprises or is a DNA sequence which encodes the transcription of an RNA the sequence of which comprises (i.e., a DNA sequence of which the RNA transcript comprises) an (addressing) sequence which comprises a fragment of at least 150 nucleotides of the RNA sequence of said yeast retrotransposon Gag protein, but which does not comprise the AUG start codon of the RNA sequence of this protein (more generally which does not comprise a reading frame whose first codon would be the translation start codon AUG, more generally which does not comprise framework of reading which, in yeast, would be an open reading frame),
- the nucleic acid of ii. does not comprise a DNA sequence encoding a complete RNA sequence of said yeast Ty retrotransposon Gag protein,
- the nucleic acid of i. and the nucleic acid of ii. do not comprise a sequence encoding a reverse transcriptase of a yeast Ty retrotransposon.

The nucleic acid of i. and the nucleic acid of ii. thereby encoding the formation, in (the cytoplasm of said) yeast cells, of a pseudo-viral particle which is formed by a protein polymer which comprises the translated Gag protein from the first nucleotide sequence, and which encapsulates said RNA (mRNA or lncRNA) of interest transcribed from the second nucleotide sequence.

In addition to the DNA sequence which encodes the expression of the Gag protein of a yeast Ty retrotransposon, the first nucleotide sequence, the nucleic acid of i, may comprise a DNA sequence which encodes the expression of a marker. for the detection of the Gag protein (e.g., a DNA sequence which encodes a fluorescent label, e.g. a fluorescent marker linked to or fused to a green fluorescent protein (GFP), especially an eGFP) and/or the expression of a label for the purification of the Gag protein (for example, a DNA sequence which encodes a poly-histidine tag and/or the bacteriophage MS2 sequence, fused the Gag protein) (cf. FIGS. 7A, 7B and 7C).

In addition to the addressing sequence, the second nucleotide sequence advantageously comprises an RNA (mRNA or lncRNA) of interest linked to this addressing sequence. The second nucleotide sequence may further comprise a DNA tag purification sequence, such as one or more (e.g., three) copies of the bacteriophage MS2 sequence (cf. FIGS. 7A, 7B and 7C).

The nucleic acid of i. can be integrated into the genome of the yeast, or not be integrated in the genome but be present in the nucleus and/or the cytoplasm of the yeast, for example in the form of an episome.

The nucleic acid of ii. can be integrated in the genome of yeast, or not be integrated into the genome but be present in the nucleus and/or cytoplasm of the yeast.

For example, the nucleic acid of i. can be integrated into the genome of yeast, and the nucleic acid of ii. may not be integrated into the genome but be present in the nucleus and/or cytoplasm of the yeast, for example as an episome.

For example, the nucleic acid of i. and the nucleic acid of ii. can both be integrated into the yeast genome (they can then be one and the same nucleic acid molecule).

More particularly, the second nucleotide sequence comprises or is a DNA sequence which encodes the transcription of an RNA whose sequence comprises (i.e. a DNA sequence whose RNA transcript comprises):

- a. the sequence of said RNA (mRNA or lncRNA) of interest, linked to
- b. an (addressing) sequence which comprises a fragment of at least 150 nucleotides of the RNA sequence of said yeast retrotransposon Gag protein, but which does not comprise the AUG start codon of the RNA sequence of this protein (more generally, which does not comprise a reading frame whose first codon would be the start codon of AUG translation, more generally which does not comprise a reading frame which, in yeast, would be an open reading frame).

Most generally, the nucleic acid of i. and the nucleic acid of ii. are each DNA. Most generally, the first nucleotide sequence and the second nucleotide sequence are each a DNA sequence, more particularly cDNA. The first nucleotide sequence is (or comprises) a DNA sequence that encodes the expression of the Gag protein of a yeast Ty retrotransposon. It therefore comprises, or is, an open reading frame that encodes the sequence of this protein.

Most generally, in the second nucleotide sequence, the bond between the sequence a. said RNA (mRNA or lncRNA) of interest, and the b. addressing sequence, is a covalent bond, or a direct bond, or a covalent and direct bond. This binding may in particular be at the 5' or 3' end of the sequence of the RNA of interest. For example, the b. addressing sequence is covalently linked to the 5' end of the sequence of the RNA of interest. For example, the b. addressing sequence is linked directly and covalently to the 3' end of the sequence of the RNA of interest.

The first nucleotide sequence advantageously contains (at least) a promoter for its expression, or for the transcription and translation of the open reading frame that it contains. The first nucleotide sequence may therefore comprise an open reading frame that encodes the sequence of the Gag protein of a yeast Ty retrotransposon, under the control of a promoter for the transcription and translation of this open reading frame into a yeast cell.

The second nucleotide sequence advantageously contains (at least) a promoter for its transcription, in particular for its transcription in a yeast cell.

The promoter of the first nucleotide sequence may be the same as that of the second nucleotide sequence, or it may be different promoters.

These promoters may each independently of one another be a constitutive promoter or an inducible promoter (e.g., a galactose-inducible promoter).

These promoters can each independently of one another be a strong promoter, that is to say a promoter to which the transcription complex (and in particular the RNA polymerase) can bind to initiate transcription, without which there must necessarily be additional factors (such as the sigma factor). For example, the promoter of the second nucleotide sequence may be a strong promoter.

Advantageously, the promoter of the first nucleotide sequence is a promoter for the expression of this first nucleotide sequence in a eukaryotic cell, more particularly a yeast cell (more particularly, for transcription and translation, in a eukaryotic cell, especially in a yeast cell, of the open reading frame which is contained in this first nucleotide sequence).

Advantageously, the promoter of the second nucleotide sequence is a promoter for the transcription of the second nucleotide sequence in a eukaryotic cell, more particularly a yeast cell.

Any inducible or constitutive promoter that the person skilled in the art considers appropriate may be implemented. Examples of inducible promoters comprise in particular promoters Gal1, Gal10, Tet07, Met.

Examples of constitutive promoters comprise, in particular, the promoters ADH, CYC, PGK1, GPD.

Advantageously, the first nucleotide sequence contains (at least) an origin for its replication, or for the replication of the open reading frame that it contains.

Likewise, the second nucleotide sequence advantageously contains (at least) an origin for its replication.

The origin of replication contained in the first nucleotide sequence is advantageously an origin of replication in prokaryote and eukaryote, more particularly an origin of replication in bacteria and yeast.

Similarly, the origin of replication contained in the second nucleotide sequence is advantageously a prokaryotic and eukaryotic origin of replication, more particularly an origin of replication in bacteria and yeast.

Advantageously, the yeast cells are yeast cells which do not comprise a nucleotide sequence which would allow the retrotransposition of the RNA (mRNA or lncRNA) of interest. One objective here is to limit or avoid the loss of RNA (mRNA or lncRNA) produced by their retro-transcription into cDNA.

Thus, advantageously, the nucleic acid of i. and the nucleic acid of ii. do not comprise a sequence encoding a reverse transcriptase of a yeast Ty retrotransposon, more generally any sequence encoding the expression of a reverse transcriptase.

In other words, the sequence of the nucleic acid of i. and the sequence of the nucleic acid of ii. are advantageously:

- without an open reading frame, which would encode the reverse transcriptase of a yeast Ty retrotransposon, or more generally a reverse transcriptase, and/or
- they lack an expression promoter of such a transcriptase.

Alternatively or additionally, the nucleic acid of i. and the nucleic acid of ii. may be devoid of sequence encoding the expression of an integrase of a yeast Ty retrotransposon, more generally any sequence coding the expression of an integrase. In other words, the sequence of the nucleic acid of i. and the sequence of the nucleic acid of ii. may lack an open reading frame, which encodes the integrase of a yeast Ty retrotransposon, or more generally an integrase, and/or they may be devoid of an expression promoter of such an integrase.

The nucleic acid of i. and the nucleic acid of ii. may furthermore be devoid of a sequence encoding the expression of a protease of the yeast Ty retrotransposon, more generally any sequence encoding the expression of a protease. In other words, the sequence of the nucleic acid of i. and the sequence of the nucleic acid of ii. may be devoid of an open reading frame, which encodes the protease of a yeast Ty retrotransposon, or more generally a protease, and/or they may be devoid of an expression promoter of such a protease.

The nucleic acid of i. and the nucleic acid of ii. may therefore be devoid of sequence encoding the expression of the Pol protein of the yeast Ty retrotransposon, more generally any sequence encoding the expression of a Pol protein.

In other words, the sequence of the nucleic acid of i. and the sequence of the nucleic acid of ii. may be devoid of an open reading frame, which encodes the Pol protein of a yeast Ty retrotransposon, or more generally a Pol protein, and/or they may be devoid of an expression promoter of such a Pol protein.

Said RNA (mRNA or lncRNA) of interest may in particular be the yeast strain implemented, or even all yeasts.

Said RNA (mRNA or lncRNA) of interest can in particular be:

- a prokaryotic RNA (mRNA or lncRNA), in particular of bacteria.
- an RNA (mRNA or lncRNA) of viruses, in particular of Zika or Influenza, or
- a eukaryotic RNA (mRNA or lncRNA) other than yeast, in particular from humans, or
- an artificial or non-natural RNA, such as for example an RNA whose translation is a polypeptide or protein comprising epitopes of proteins of different microorganisms (for example epitopes of different bacteria and/or viruses), in particular antigen epitopes (including epitopes of proteins of different microorganisms, which are antigenic in humans), an artificial or non-natural RNA, such as for example a RNA whose translation is a polypeptide or protein comprising different epitopes of at least one protein the same microorganism (for example epitopes of bacteria and/or viruses), in particular epitopes of antigens (in particular protein epitopes of a microorganism, which are antigenic in humans, more particularly

- an RNA (mRNA or lncRNA) of viruses, in particular of Zika or Influenza, or
- a eukaryotic RNA (mRNA or lncRNA) other than yeast, in particular from humans,
- an artificial or non-natural RNA, such as, for example, an RNA whose translation is a polypeptide or protein comprising epitopes of proteins of different microorganisms (for example epitopes of different bacteria and/or viruses), in particular antigen epitopes (including protein epitopes of different microorganisms, which are antigenic in humans), more particularly a eukaryotic RNA (mRNA or lncRNA) other than yeast, in particular human.

Said RNA (mRNA or lncRNA) of interest may comprise at least 120 nucleotides, in particular at least 150 nucleotides, in particular at least 180 nucleotides, in particular at least 210 nucleotides, in particular at least 240 nucleotides, in particular at least 270 nucleotides, in particular at least 2300 nucleotides.

Alternatively or additionally, said RNA (mRNA or lncRNA) to be produced may comprise less than 6000 nucleotides, less than 5800 nucleotides, in particular less than 5000 nucleotides, in particular less than 4000 nucleotides, in particular less than 3000 nucleotides, in particular less than 2000 nucleotides, in particular less than 1800 nucleotides. All combinations of minimum number and maximum number of nucleotides are here explicitly targeted. Said RNA (mRNA or lncRNA) of interest may for example comprise at least 150 nucleotides and less than 2000 nucleotides.

Said RNA (mRNA or lncRNA) of interest can in particular code (that is to say the protein translation of its sequence can be that of):

- a bacteria protein or polypeptide,
- a genomic editing enzyme (such as Cas9, transposase),
- a virus protein or polypeptide,
- a transcription factor (of eukaryote other than yeast, in particular human),
- a growth factor (of eukaryote other than yeast, in particular human),
- a CFTR protein (Cystic fibrosis transmembrane conductance regulator) (human),
- an antibody (polyclonal or monoclonal), or antibody fragment (in particular Fv, Fab or F(ab')2)), in particular an intra-antibody [intrabody] or a humanized antibody, or
- a polypeptide comprising at least one epitope (bacteria or viral), in particular several epitopes (bacteria and/or viral) optionally separated by spacer sequences, more particularly

- a virus protein or polypeptide,
- a transcription factor (of eukaryote other than yeast, in particular human),
- a growth factor (of eukaryote other than yeast, in particular human),
- a CFTR protein (Cystic fibrosis transmembrane conductance regulator) (human),
- an antibody (polyclonal or monoclonal), or antibody fragment (in particular Fv, Fab or F(ab')2)), in particular an intrabody [intrabody] or a humanized antibody, more particularly
- a transcription factor (of eukaryote other than yeast, in particular human),
- a growth factor (of eukaryote other than yeast, in particular human),
- a CFTR protein (Cystic fibrosis transmembrane conductance regulator) (human),
- an antibody (polyclonal or monoclonal), or antibody fragment (in particular Fv, Fab or F(ab')2)), in particular an intrabody or a humanized antibody, more particularly a transcription factor (d eukaryote other than yeast, in particular of human) or a growth factor (of eukaryote other than yeast, in particular of human)

Several different RNAs (mRNA or lncRNA) can be produced in the same yeast recombinant cell. Each of these different RNAs has a second nucleotide sequence of its own (DNA sequence whose RNA transcript comprises the RNA sequence of interest linked to an addressing sequence). Each of these second nucleotide sequences may be comprised or carried on the same nucleic acid molecule of ii, or on separate nucleic acid molecules of ii. The yeast which has been genetically modified to produce the complexes, granules or pseudo-viral (recombinant) particles of the application may advantageously have genetic mutations, in particular chromosomal mutations, which are intended to stimulate or increase the production of these pseudo-viral particles.

It may for example be one or more yeast gene mutations, which comprise one or more mutations chosen from:

- replacing one or more codons each with another codon or with another triplet of nucleotides, and
- the deletion of one or more nucleotides.

The yeast genes may for example be one or more genes among the Rpb1, Spt21, Srb2 and Srb5 genes.

For example, the Rpb1 gene may comprise a codon substitution that confers the amino acid mutation C67Y, C70Y or H80Y. For example, the Rpb1 gene of the strain may be replaced by the Rpb1 gene of another yeast strain, in particular another yeast strain which belongs to the same genus of yeast, and which carries at least one of these substitutions of codons. For example, the Rpb1 gene of *S. paradoxus* can be replaced by the Rpb1 gene of *S. cerevisiae*, into which one or more of the codon mutations that confer the amino acid mutations C67Y, C70Y and H80Y have been introduced.

For example, one or more of the Spt21, Srb2 and Srb5 genes may be (at least partially) deleted [ΔSpt21, ΔSrb2 and ΔSrb5].

For example, the yeast may be a yeast of which:

the Rpb1 gene comprises the replacement of codon (s) by a codon (s) which confers (s) one (or more) of the amino acid mutations C67Y, C70Y and H80Y (or has been replaced by the Rpb1 gene of another yeast strain, in which at least one of these replacements has been performed), and one or more of the Spt21, Srb2 and Srb5 genes are deleted (at least partially deleted, at least sufficiently deleted to no longer produce protein).

For example, the yeast may be a strain of *S. paradoxus* (which is naturally free of Ty1 in particular Ty1 (strain TyO)), which is:

Rpb1 C67Y,
Rpb1 C70Y,
Rpb1 H80Y,
ΔSrb2,
ΔSpt21,
ΔSrb2 and ΔSpt21,
C67Y ΔSrb2,
C70Y ΔSrb2,
Rpb1 H80Y ΔSrb2,
Rpb1 C61Y ΔSpt21,
Rpb1C70Y ΔSpt21,
Rpb1 H80Y ΔSpt21,
Rpb1 C67Y ΔSrb2 ΔSpt21,
Rpb1 C70Y ΔSrb2 ΔSpt21, or
Rpb1 H80Y ΔSrb2 ΔSpt21.

It may for example be a strain of *S. cerevisiae* (which has been genetically modified not to produce T retrosomes (strain TyO), and) which is (further) genetically modified to be:

Rpb1 C67Y,
Rpb1 C70Y,
Rpb1 H80Y,
ΔSrb2,
ΔSpt21,
ΔSrb2 ΔSpt21,
C67Y ΔSrb2,
C70Y ΔSrb2,
Rpb1 H80Y ΔSrb2,
Rpb1 C67Y ΔSpt21,
Rpb1 C70Y ΔSpt21,
Rpb1 H80Y ΔSpt21,
Rpb1 C67Y ΔSrb2 ΔSpt21,
Rpb1 C70Y ΔSrb2 ΔSpt21, or
Rpb1 H80Y ΔSrb2 ΔSpt21.

Alternatively or additionally to genetic mutations, including chromosomal mutations, which are intended to stimulate or increase the production of these pseudo-viral particles, one or more products may be used to stimulate or increase this production. This or these products may in particular be present in the transfection or culture medium in which the yeast is placed.

Yeast (recombinant) cells which have been genetically modified to comprise nucleic acids of i. and ii. can be placed under conditions allowing the nucleic acid of i. (at the first nucleotide sequence) to express the Gag protein that it encodes, and to the nucleic acid of ii. (at the second nucleotide sequence) to transcribe the AR that it codes. They can in particular be placed on or in a culture medium adapted to the growth or multiplication of yeast (cf. below). If the first nucleotide sequence and/or the second nucleotide sequence carry inducible promoters, this medium may especially comprise any compound or product that would be necessary for the induction of the promoter (s).

The complexes, granules, or virus-like particles produced by the (recombinant) yeast cells are collected, for example by lysis of the cells, in particular by chemical or mechanical lysis (by beads, rather than by sonication), and the RNA contained in these complexes, granules or pseudo-viral particles, and in particular the mRNA or lncRNA thus contained, are purified.

Alternatively, the RNAs contained in these complexes, granules or pseudo-viral (recombinant) particles, and in particular the mRNAs or lncRNAs contained therein, are directly extracted or purified from the yeast cells, without extraction or prior collection of the complexes, granules or pseudo-viral particles that contain them. Large amounts of RNA (mRNA or lncRNA) can thus be produced, for example at least 0.9 gram of RNA (mRNA or lncRNA) per liter of yeast culture.

Advantageously, the RNA, which is present or produced in the complex, granulates, pseudo-viral particle of the application, comprises post-transcriptional modifications that make it competent for translation into mammalian cells.

Advantageously, the complex RNA, granule, pseudo-viral particle of the application can be provided with a polyA tail at the 3' end.

Advantageously, the complex RNA, granule, pseudo-viral particle of the application can be provided with a cap at the 5' end, more particularly a cap as known to those skilled in the art, more particularly a cap which comprises a 7-methylguanosine (linked to the mRNA by three phosphates in 5'-5' configuration). This cap may block the action of exonucleases and may be necessary to stimulate the (future) translation of the RNA of interest (mRNA or lncRNA) into mammalian cells.

Advantageously, the complex RNA, granule, pseudo-viral particle of the application can be methylated, especially at one or more of its adenine and/or cytosine and/or pseudouridine residue(s), especially at one or more of its adenine and/or cytosine residue(s).

Advantageously, the RNA, which is present or produced in the complex, granulates, the pseudo-viral particle of the application, comprises post-transcriptional modifications such as methylation of cytosine and/or adenine and/or pseudouridine residue(s), more particularly of cytosine and/or adenine residue(s) which increase its translational efficiency in mammalian cells.

The means of the application are therefore particularly suitable for the production of RNA (mRNA or lncRNAc) which is intended for administration in a eukaryote, in particular a multicellular eukaryote, in particular a mammal, in particular a human.

Several examples of yeast strains according to the application have been filed with the CNCM (see below).

The application also relates to each of the means implemented or produced by the RNA production method described herein, so that for their use the production of mRNA or lncRNA exhibiting a polyA tail at the 3' end and/or a 7-methylguanosine (m7G) cap at the 5' end (or methylation of adenine and/or cytosine and/or pseudouridine residue(s), including adenine and/or cytosine residue(s)).

The application is thus relative to the nucleic acid of i. as described herein.

The application also relates to the nucleic acid of ii. as described herein.

The application is thus related to the association of the nucleic acid of i. and the nucleic acid of ii. as described herein, and their combination for simultaneous, separate or delayed use, more particularly for their simultaneous, separate or delayed use in the transfection or transformation of yeast cells, more particularly yeast as described.

More particularly, the application relates to a kit which comprises a nucleic acid i. and/or, preferably and, a nucleic acid ii. as here described. This kit is especially adapted to the recombinant production of RNA, in particular mRNA or lncRNA, as described here.

Advantageously, the kit does not comprise a protein or nucleic acid allowing retrotransposition of the mRNA or lncRNA to produce, more particularly its retrotransposition in a yeast cell.

Advantageously, the kit does not comprise a reverse transcriptase of a yeast Ty retrotransposon, or nucleic acid encoding such a reverse transcriptase.

Alternatively or additionally, the kit does not comprise an integrase of a yeast Ty retrotransposon, or nucleic acid encoding such an integrase.

Advantageously, the kit does not comprise a protease of a yeast Ty retrotransposon, or nucleic acid encoding such a protease.

More generally, the kit may not comprise a reverse transcriptase or nucleic acid encoding a reverse transcriptase.

More generally, the kit may not comprise an integrase or nucleic acid encoding an integrase.

More generally, the kit may not comprise a protease or nucleic acid encoding a protease.

The application is thus related to a kit (which is specially adapted to the implementation of the recombinant method of producing the RNA of the application), which comprises:

i. at least one nucleic acid comprising a first nucleotide sequence and/or, preferably and, ii. at least one nucleic acid comprising a second nucleotide sequence, as described herein, more particularly for simultaneous, deferred or separate use in time.

More particularly, the nucleic acid of i. and/or (preferably and) the nucleic acid of ii. of the kit can be defined as follows:

- the first nucleotide sequence comprises a DNA sequence which encodes the expression of the Gag protein of a yeast Ty retrotransposon,
- the Gag protein of a yeast Ty retrotransposon is a Gag protein of a yeast Ty2 or Ty3 retrotransposon, (Ty of yeast, in particular Ty1, Ty2 or Ty3 of yeast, especially Ty1, Ty2, Ty3, Ty4 or Ty5 of yeast), and the sequence of this Gag protein is the sequence of SEQ ID NO: 3 or a sequence which is identical to minus 90% to the sequence of SEQ ID NO: 3,
- the second nucleotide sequence comprises a DNA sequence which comprises the sequence of SEQ ID NO: 16 or a fragment of at least 150 nucleotides of the sequence of SEQ ID NO: 16, and advantageously does not comprise a frame of reading, the first of which codon would be the translation start codon (ATG) (or more generally, does not comprise a reading frame that, in yeast, would be an open reading frame)
- the nucleic acid which comprises the second nucleotide sequence does not comprise a DNA sequence whose RNA transcript is the complete RNA sequence of said yeast retrotransposon Gag protein, and
- the nucleic acid which comprises the first nucleotide sequence and the nucleic acid which comprises the second nucleotide sequence are one and the same molecule, or two distinct or separate molecules.

The kit may not comprise yeast retrotransposon reverse transcriptase, or nucleic acid encoding such a reverse transcriptase, or nucleic acid comprising a sequence encoding such a reverse transcriptase.

A kit of the application may further comprise one or more cells of a yeast as described here, more particularly one or more cells of a yeast:

- which is devoid of Ty1 retrotransposon or which is naturally provided with a Ty1 retrotransposon sequence but whose Ty1 retrotransposon sequence has been genetically modified so as not to produce a T-retrosome, or more generally a yeast
- which is devoid of Ty retrotransposon or which has been genetically modified so as not to produce a T-retrosome.

The yeast cell(s) of the kit may advantageously not comprise a protein which would allow the retrotransposition of the RNA (mRNA or lncRNA) to be produced (reverse transcriptase, in particular), or of nucleic acid which would code such a protein.

Advantageously, the yeast cell(s) of the kit do not comprise a reverse transcriptase of a yeast Ty retrotransposon, or nucleic acid encoding such a reverse transcriptase.

Alternatively or additionally, the yeast cell(s) of the kit do not comprise an integrase of the yeast Ty retrotransposon or nucleic acid encoding such an integrase.

Advantageously, the yeast cell or cells of the kit do not comprise a protease of a yeast Ty retrotransposon, or nucleic acid encoding such a protease.

More generally, the yeast cell (s) of the kit may not comprise a reverse transcriptase or nucleic acid encoding a reverse transcriptase.

More generally, the yeast cell (s) of the kit may not comprise an integrase or nucleic acid encoding an integrase.

More generally, the yeast cell (s) of the kit may not comprise a protease or nucleic acid encoding a protease.

Of course, the yeast of the kit may comprise one or more copies of at least one of the nucleic acid of i. and the nucleic acid of ii.

A kit of the request can for example comprise:

- one or more cells of a yeast as described here, which cell(s) comprise the first (integrated) nucleotide sequence in its chromosomes; and in distinct or separate form,
- the nucleic acid of ii. (or the second nucleotide sequence), for example in the form of a non-integrative vector, more particularly a replicative vector.

The kit may further comprise a leaflet containing instructions for its use in the transfection or transformation of yeast cells, and/or for its use in the (recombinant) production of RNA, more particularly mRNA or lncRNA, such as described here, especially for this production in yeast cells.

The kit may in particular comprise a leaflet containing instructions for genetically modifying cells of a yeast, in particular yeast as described here (or, where appropriate, as contained in the kit), these genetic modifications comprising the transfection or transformation of these yeast cells by nucleic acids i. and ii. of the kit.

The kit may advantageously be used for the production of mRNA or lncRNA exhibiting a polyA tail at the 3' end and/or a 7-methylguanosine (m7G) cap at the 5' end (or even a methylation of adenine and/or cytosine and/or pseudouridine residue(s), especially adenine and/or cytosine residues(s)).

The application also relates to a bacteria cell that has been genetically engineered to comprise the nucleic acid of i. and/or, preferably, and the nucleic acid of ii. as described herein, in particular to comprise them in its cytoplasm.

The application also relates to a plurality of such bacteria cells, and in particular to a strain of bacteria whose cells comprise or are such cells. The bacteria may for example be *Escherichia*, especially *E. coli*, for example the bacteria *E. coli* DH5a, which is accessible from the ATCC under the number 67877™. The bacteria cell or cells may advantageously be used to amplify the nucleic acids of i. and/or ii, for example before transferring them to a yeast cell.

The application also relates to a culture medium for microorganisms, in particular to an artificial medium for culturing bacteria, which comprises at least one bacteria cell of the application or at least one strain of bacteria of the application.

This medium may for example be in liquid or solid form.

The composition of this culture medium may be that of a culture medium suitable for bacteria growth or multiplication. In particular, it comprises one or more elements among tryptone, yeast extract and NaCl, more particularly at least yeast extract, more particularly at least yeast extract and tryptone. For example, the composition of this culture medium may in particular be or comprise that of a SOB medium (Super Optimal Broth), a SOC medium (Super Optimal Broth with Catabolite Repression), or an LB medium (Lysogeny Broth). This type of culture medium composition is well known to those skilled in the art. A SOB medium may for example comprise tryptone and yeast extract, for example: 2% w/v tryptone, 0.5% w/v yeast extract, 8.56 to 10 mM NaCl, 2.5 mM KCl 10 mM $MgCl_2$, 10 mM $MgSO_4$, $H_2O$ qsp 1000 mL.

A SOC medium may differ from a SOB medium only by the addition of a sugar, for example glucose, for example 20 mM glucose.

An LB medium may for example comprise tryptone, yeast extract and NaCl.

The culture medium may advantageously be used for the production of mRNA or lncRNA having a polyA tail at the 3' end and/or a 7-methylguanosine (m7G) cap at the 5' end (or even a methylation of adenine and/or cytosine and/or pseudouridine, especially adenine and/or cytosine residue(s)).

The application also relates to a yeast cell that has been genetically modified to comprise the nucleic acid of i. and/or, preferably, and the nucleic acid of ii. as described herein, especially to comprise these nucleic acids in its nucleus (including its chromosomes) and/or its cytoplasm.

The application thus relates to a yeast cell (recombinant) (which is specially adapted to the implementation of the recombinant method of producing the RNA of the application), and which is characterized in that:

- the yeast cell is devoid of Ty1, Ty2 and Ty3 retrotransposon, (Ty1, more particularly Ty1, Ty2 and Ty3, more particularly Ty1, Ty2, Ty3, Ty4 and Ty5 retrotransposons of yeast, more particularly of any retrotransposon of yeast), and
- the yeast cell does not comprise a reverse transcriptase of a yeast Ty retrotransposon, nor nucleic acid encoding such a reverse transcriptase, nor nucleic acid comprising a sequence encoding such a reverse transcriptase, nor nucleic acid comprising a sequence coding such a reverse transcriptase,
- the yeast cell has been genetically modified to comprise:
  - i. at least one nucleic acid comprising a first nucleotide sequence and/or, preferably and,
  - ii. at least one nucleic acid comprising a second nucleotide sequence, as described here.

More particularly, in the yeast cell, the nucleic acid of i. and/or the nucleic acid of ii. can be defined as follows:

- the first nucleotide sequence comprises a DNA sequence which encodes the expression of the Gag protein of a yeast Ty retrotransposon,
- the Gag protein of a yeast Ty retrotransposon is a Gag protein of a yeast Ty1 Ty2 or Ty3 retrotransposon (Ty of yeast, in particular Ty1, Ty2 or Ty3 of yeast, in particular Ty1, Ty2, Ty3, Ty4 or Ty5 of yeast), and the sequence of this Gag protein is the sequence of SEQ ID NO: 3 or a sequence which is at least 90% identical to the sequence of SEQ ID NO: 3,
- the second nucleotide sequence comprises a DNA sequence whose RNA transcript comprises the sequence of SEQ ID NO: 16 or a fragment of at least 150 nucleotides of the sequence of SEQ ID NO: 16, and advantageously does not comprise a reading frame whose first codon would be the translation start codon (ATG) (or, more generally, does not comprise a reading frame which, in yeast, would be an open reading frame),
- the nucleic acid which comprises the second nucleotide sequence does not comprise a DNA sequence whose RNA transcript would be the complete RNA sequence of said Gag protein of a yeast Ty retrotransposon, and
- the nucleic acid which comprises the first nucleotide sequence and the nucleic acid which comprises the second nucleotide sequence are one and the same molecule, or two distinct or separate molecules.

For example, the yeast cell may comprise the first nucleotide sequence, more particularly the first nucleotide sequence integrated into its chromosomes. This yeast cell may further comprise the nucleic acid of i. in its nucleus and/or cytoplasm, in non-integrated form to its chromosomes, for example in the form of a replicative plasmid.

Advantageously, this yeast cell is a cell of a yeast:

- which is (naturally) devoid of Ty1 retrotransposon, or which is naturally provided with a Ty1 retrotransposon sequence but whose Ty1 retrotransposon sequence has been genetically modified so as not to produce a T retrosome, or more generally
- which is (naturally) devoid of Ty retrotransposon or which has been genetically modified so as not to produce a T-retrosome.

The yeast cell may advantageously not comprise a protein which would allow the retrotransposition of the mRNA or lncRNA to be produced (reverse transcriptase, in particular), or nucleic acid which would encode such a protein.

Advantageously, the yeast cell does not comprise a reverse transcriptase of a yeast Ty retrotransposon, or nucleic acid encoding such a reverse transcriptase.

Alternatively or additionally, the yeast cell does not comprise an integrase of a yeast Ty retrotransposon or nucleic acid encoding such an integrase.

Advantageously, the yeast cell does not comprise a protease of a yeast Ty retrotransposon, or nucleic acid encoding such a protease.

More generally, the yeast cell may not comprise a reverse transcriptase or nucleic acid encoding a reverse transcriptase.

More generally, the yeast cell may not comprise an integrase or nucleic acid encoding an integrase. More generally, the yeast cell may not comprise a protease or nucleic acid encoding a protease.

The yeast cell (s) may advantageously be used for the production of mRNA or lncRNA having a polyA tail at the 3' end and/or a 7-methylguanosine (m7G) cap at the 5' end (or even a methylation of cytosine and/or adenine and/or pseudouridine residue(s), more particularly cytosine and/or adenine residue(s)).

The application also relates to a plurality of such yeast cells, and in particular to a yeast strain whose cells comprise or are such cells. The yeast cell or strain of the application is especially adapted to the (recombinant) production of RNA, especially RNA heterologous to this yeast, more particularly mRNA or lncRNA heterologous to this yeast.

A yeast strain of the application can in particular be the strain I-5171 which was deposited with the CNCM under the Budapest Treaty on Feb. 24, 2017 (strain «TB16»). This yeast is a strain of *S. paradoxus*, whose Rpb1 gene has been replaced by a mutated version of the *S. cerevisiae* Rpb1 gene (ie a C67Y version of the *S. cerevisiae* Rpb1 gene), and in which a nucleic acid of i. has been transferred. This nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA].

A yeast strain of the application may in particular be the strain I-5172 which was deposited with the CNCM under the Budapest Treaty on Feb. 24, 2017 (strain «TB17»). This yeast is a strain of *S. paradoxus*, whose Rpb1 gene has been replaced by a mutated version of the *S. cerevisiae* Rpb1 gene (ie a C70Y version of the *S. cerevisiae* Rpb1 gene), and in which a nucleic acid of i. has been transferred. This nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA].

A yeast strain of the application may in particular be the strain 1-5173 which was deposited with the CNCM under the Budapest Treaty on Feb. 24, 2017 (strain «TB18»). This yeast is a strain of *S. paradoxus*, whose Rpb1 gene has been replaced by a mutated version of the *S. cerevisiae* Rpb1 gene (namely an H80Y version of the *S. cerevisiae* Rpb1 gene), and in which a nucleic acid of i. has been transferred. This nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA].

A yeast strain of the application may in particular be the strain I-5174 which was deposited with the CNCM under the Budapest Treaty on Feb. 24, 2017 (strain «TB21»). This yeast is a strain of *S. paradoxus*, whose Srb2 gene has been deleted, whose Rpb1 gene has been replaced by a mutated version of the *S. cerevisiae* Rpb1 gene (namely an H80Y version of the *S. cerevisiae* Rpb1 gene), and in which a nucleic acid of i. has been transferred. This nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA].

A yeast strain of the application may in particular be the strain I-5175 which was deposited with the CNCM under the Budapest Treaty on Feb. 24, 2017 (strain «TB32»). This yeast is a strain of *S. paradoxus*, whose Srb2 gene has been deleted, and in which a nucleic acid of i. has been transferred. This nucleic acid of i. is integrated into the genome of yeast, and comprises a sequence encoding the Gag-eGFP-6His-3MS2 fusion protein (Ty1 Gag, in this case Gag of SEQ ID NO: 3, eGFP of SEQ ID NO: 27; 6His of SEQ ID NO: 6; 3MS2=3 copies of the bacteriophage MS2 sequence, as a purification tag) under the influence of a galactose (Gal) promoter [selective medium URA].

A yeast strain of the application may in particular be the strain I-5176 which was deposited with the CNCM under the Budapest Treaty on Feb. 24, 2017 (strain «TBScl»).

This yeast is a strain of *S. cerevisiae*, which is virgin of Ty elements (TyO), and which has been transformed by an episomal plasmid containing a nucleic acid of i., In this case a nucleic acid allowing the expression of a Gag-eGFP fusion protein (Gag of SEQ ID NO: 3, eGFP of SEQ ID NO: 27) under the influence of a galactose (Gal) promoter [selective medium URA].

The CNCM is the National Collection of Culture of Microorganisms (Institut Pasteur, 28 rue du Dr Roux, 75724 Paris Cedex 15, France).

A yeast strain of the application may also be one of I-5171 to I-5176, wherein a nucleic acid of ii. has been transferred, for example in the form of a plasmid, in particular a non-integrative plasmid, more particularly a replicative plasmid.

A yeast strain of the application may especially be the I-5293 strain which was deposited with the CNCM under the Budapest Treaty on Mar. 15, 2018 (strain «TB53»).

This yeast is a *S. paradoxus* strain whose Srb2 gene has been deleted, and in which a nucleic acid of i. and ii have been transferred. The nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA].

The nucleic acid ii., meanwhile, corresponds to a non-integrative plasmid allowing the expression of a Luciferase model RNA (SEQ ID NO: 29) having in 3' of a complete mutated addressing sequence (GAGm=SEQ ID NO: 14) RNA in T-bodies under the influence of a galactose promoter (GAL) [Selective Medium LEU].

A yeast strain of the application can in particular be the strain I-5294 which was deposited with the CNCM under the Budapest Treaty on Mar. 15, 2018 (strain «TB54»).

This yeast is a *S. paradoxus* strain whose Srb2 gene has been deleted, and in which a nucleic acid of i. and ii. have been transferred. The nucleic acid of i. is integrated in the genome of yeast, and comprises a sequence coding for the Gag-eGFP fusion protein (Ty1 Gag, in this case Gag of SEQ ID NO: 3, eGFP of SEQ ID NO: 27) under the influence a galactose promoter (Gal) [selective medium URA]. The nucleic acid ii., Meanwhile, corresponds to a non-integrative plasmid allowing the expression of a luciferase model RNA (SEQ ID NO: 29) having a partial (or minimal) addressing sequence (SEQ ID NO: 18) RNA in T-bodies under the influence of a galactose promoter (GAL) [Selective Medium LEU].

The CNCM is the National Collection of Culture of Microorganisms (Institut Pasteur, 28 rue du Dr Roux, 75724 Paris Cedex 15, France).

A cell of the application can in particular be a cell of one of these strains.

The yeast cell (s) may advantageously be used for the production of mRNA or lncRNA exhibiting a polyA tail at the 3' end and/or a 7-methylguanosine (m7G) cap at the 5' end (or even a methylation of adenine and/or cytosine and/or pseudouridine residue(s), especially of adenine and/or cytosine residue(s)).

The application also relates to a microorganism culture medium, in particular to an artificial microorganism culture medium, which comprises at least one yeast cell of the application or at least one yeast strain of the application. This medium may for example be in liquid form.

The composition of this culture medium may be that of a medium adapted to the growth or multiplication of yeast cells. It may in particular comprise one or more elements among yeast extract, glucose, peptone and NaCl, more particularly at least yeast extract and/or glucose, more particularly at least yeast extract.

This medium may in particular further comprise a compound or product that would be necessary for the induction of promoter (s).

The culture medium can advantageously be used for the production of mRNA or lncRNA exhibiting a polyA tail at the 3' end and/or a 7-methylguanosine (m7G) cap at the 5' end (or even a methylation of adenine and/or cytosine and/or or pseudouridine residue(s), especially adenine and/or cytosine residue(s)).

The application also relates to a medium for transfection or transformation of microorganisms, especially yeast, more particularly to an artificial medium for transfection or transformation of microorganisms, especially yeast. The transfection or demand transformation medium comprises at least one yeast cell of the application or at least one yeast strain of the application. This medium may be in liquid form, in particular in the form of a suspension.

The composition of this transfection or transformation medium may in particular comprise polyethylene glycol (PEG), in particular PEG 50, and may further optionally comprise denatured salmon DNA and/or lithium acetate.

The transfection or transformation medium may advantageously be used for the production of mRNA or lncRNA having a polyA tail at the 3' end and/or a 7-methylguanosine (m7G) cap at the 5' end (or even a methylation of adenine and/or cytosine and/or pseudouridine residue(s), especially of adenine and/or cytosine residue(s).

The application also relates to a complex, a granule, a particle or a virus-like particle (VLP) (recombinant). This complex, granule, pseudo-viral particle (recombinant) is likely to be produced during the implementation of the method of production (recombinant) AR demand (and by collecting the complex, granule, pseudo-particle viral thus produced). This complex, granule, pseudo-viral particle comprises an RNA complexed with, or encapsulated by, a protein polymer, wherein the protein polymer comprises the Gag protein of a yeast Ty retrotransposon.

The nucleotide sequence of the RNA comprises said addressing sequence («b. sequence») and/or the sequence of a molecule of an RNA (in particular an mRNA or lncRNA) of interest ("sequence a."), More particularly said addressing sequence linked to the sequence of a molecule of an RNA (in particular an mRNA or lncRNA) of interest.

The application is thus relative to a pseudo-viral (recombinant) particle (which can be obtained by collecting a pseudo-viral particle produced during the implementation of the recombinant RNA production method of the application), and which is characterized in that the pseudo-viral particle comprises an RNA encapsulated by a protein polymer, wherein:

- the protein polymer comprises the Gag protein of a yeast Ty retrotransposon,
- the Gag protein of a yeast Ty retrotransposon is a Gag protein of a yeast Ty2 or Ty3 retrotransposon, and the sequence of this Gag protein is the sequence of SEQ ID NO: 3 or a sequence which is at least 90% identical to the sequence of SEQ ID NO: 3,
- the nucleotide sequence of the encapsulated RNA comprises the sequence of SEQ ID NO: 16 or a fragment of at least 150 nucleotides of the sequence of SEQ ID NO: 16 (but preferably does not comprise a reading frame, the first of which codon would be the translation start codon [start] (AUG)), and does not comprise the RNA sequence which is the RNA transcript of SEQ ID NO: 2, and
- the pseudo-viral particle does not comprise a reverse transcriptase, a nucleic acid encoding a reverse transcriptase, or a nucleic acid comprising a sequence encoding such a reverse transcriptase.

Advantageously, the complex RNA, granule, pseudo-viral particle of the application, more particularly the RNA of interest, in particular the mRNA or lncRNA of interest, («a. sequence»), can be provided with a polyA tail at the 3' end (cf. FIGS. 7A, 7B and 7C).

Advantageously, the complex RNA, granule, pseudo-viral particle of the application, more particularly the RNA, in particular the mRNA or lncRNA («a. sequence «), can be provided with a cap in the 5' position, more particularly at its 5' end (cf. FIGS. 7A, 7B and 7C), including a cap which comprises a 7-methylguanosine (linked to the mRNA by three phosphate). This cap can block the action of exonucleases, and may be necessary to stimulate (future) translation of said RNA into mammalian cells.

Advantageously, the complex RNA, granule, pseudo-viral particle of the application, more particularly the RNA of interest, in particular the mRNA or lncRNA («a. sequence»), can be methylated, in particular at the level of one or more of its adenine and/or cytosine and/or pseudouridine residue (s), in particular adenine and/or cytosine residue(s).

This complex, granule, pseudo-viral particle (and in particular the protein polymer of this complex, granule, pseudo-viral particle) may not comprise a protein that would allow the retrotransposition of the RNA (mRNA or lncRNA) of interest (transcriptase reverse, in particular), or nucleic acid that would encode such a protein. This complex, granule, pseudo-viral particle (and in particular the protein polymer of this complex, granule, pseudo-viral particle) may not comprise a reverse transcriptase of a yeast Ty retrotransposon, or nucleic acid encoding such a reverse transcriptase.

This complex, granule, pseudo-viral particle (and in particular the protein polymer of this complex, granule, pseudo-viral particle) may not comprise yeast Ty retrotransposon integrase or nucleic acid encoding such an integrase.

This complex, granule, pseudo-viral particle (and in particular the protein polymer of this complex, granule, pseudo-viral particle) may not comprise a protease of a yeast ty retrotransposon, or nucleic acid encoding such a protease.

More generally, this complex, granule, pseudo-viral particle (and in particular the protein polymer of this complex, granule, pseudo-viral particle) may not comprise a reverse transcriptase or nucleic acid encoding a reverse transcriptase. More generally, this complex, granule, pseudo-viral particle (and in particular the protein polymer of this complex, granule, pseudo-viral particle) may not comprise integrase or nucleic acid encoding an integrase.

More generally, this complex, granule, pseudo-viral particle (and in particular the protein polymer of this complex, granule, pseudo-viral particle) may not comprise a protease or nucleic acid encoding a protease.

The application also relates to the RNA isolated from this complex, granule, pseudo-viral particle.

The complex, granule or pseudo-viral particle may advantageously be used for the production of mRNA or lncRNA exhibiting a polyA tail at the 3' end and/or a 7-methylguanosine (m7G) cap at the 5' end (or even a methylation of one or more adenine and/or cytosine and/or pseudouridine residue(s), especially adenine and/or cytosine residue(s)).

The application also relates to a method for producing (in vitro) DNA (in particular cDNA), which comprises producing an RNA (in particular an mRNA or lncRNA) according to the method of producing RNA from the application, and to retro-transcribe this RNA into DNA (in particular into cDNA), and to collect this DNA (or cDNA).

The application also relates to a method for producing (in vitro) protein, which comprises producing an mRNA according to the RNA production method of the application, and translating this mRNA into protein in vitro (for example in vitro). In vitro, in particular in mammalian cells, especially in human cells), and to collect this protein.

The application also relates to a method for the production of a pharmaceutical composition comprising at least one RNA of interest, in particular at least one mRNA or lncRNA of interest.

The method comprises producing at least one RNA by the RNA production method of the application, and placing the RNA in contact with (in admixture with, in suspension in) or in a pharmaceutically acceptable carrier to produce a pharmaceutical composition.

The term «pharmaceutical composition» is understood in accordance with its usual meaning in the field. It comprises the meaning of a drug, including a vaccine or immunogenic composition.

The term «pharmaceutically acceptable carrier» is meant in accordance with its usual meaning in the art. It comprises the meaning of «physiologically acceptable vehicle», including physio logically acceptable for administration to humans.

For example, a pharmaceutically (or physiologically) acceptable carrier may have one or more of the following functions: diluent functions, excipient, additive, emulsifier, dispersing agent, pH adjusting agent, preservative, surfactant, gelling agent, buffering agent, stabilizing agent, an RNA stabilizing agent (especially an agent protecting the RNA from enzymatic degradation), a solubilizing agent.

Examples of pharmaceutically (or physiologically) acceptable carriers are known to those skilled in the art, and are for example described in «Remington: The Science and Practice of Pharmacy», 20th Edition, Mack Publishing Co. and in «Ansel's Pharmaceutical Dosage Forms and Drug Delivery Systems», Ansel, Popovich and Allen Jr., Lippincott Williams and Wilkins (Ninth Edition).

Examples of pharmaceutically (or physiologically) acceptable vehicles may for example comprise injectable fluids, such as water, physiological saline, buffers, emulsions.

The pharmaceutical composition (or drug) may in particular be intended for:

- the prevention or the treatment of a microbiological infection, in particular bacterial and/or viral and/or parasitic (infectious diseases or bio-defense),
- the prevention or the treatment of a tumor proliferation,
- the prevention or the treatment of a chronic disease (eg cystic fibrosis),
- a tissue or cell regeneration therapy (cardiovascular diseases, rare diseases), or
- a gene therapy (in particular by gene correction or a genetic deficit, in particular by re-expression of protein that is found to be non-functional or non-expressed).

For example, an RNA produced according to demand can be formulated as:

- an RNA vaccine or an immunogenic RNA composition (the administered RNA being intended to be translated into the cells, in particular the dendritic cells, of the subject, in particular the human subject, to which it is administered);
- an anti-tumor drug;
- a drug for the treatment or palliation of cystic fibrosis (for example, by the introduction of RNA encoding CFTR); or
- a drug or tissue or cell regenerative product.

The fact that the RNA produced in accordance with the application can have a polyA tail at the 3' end and/or a 7-methylguanosine (m7G) cap at the 5' end, or even a methylation of adenine and/or cytosine and/or pseudouridine residue(s), in particular adenine and or cytosine, makes it directly competent for translation into mammalian cells, especially in human cells.

In the application, unless otherwise specified, or the context dictates otherwise, all terms have their usual meaning in the area (s) concerned. The term «comprising», with which «including» or «containing» is synonymous, is an open term, and does not exclude the presence of one or more element (s), ingredient (s) or step (s) of additional method (s) that would not be explicitly stated, while the term «consistent» or «constituted» is a closed term, which excludes the presence of any additional element, step, or ingredient that does not would not be explicitly exposed. The term «substantially consisting of» or «essentially consisting of» is a partially open term, which does not exclude the presence of one or more element (s), ingredient (s) or additional step (s) in the to the extent that such element (s), ingredient (s) or additional step (s) do not materially affect the basic properties of the invention.

Therefore, the term «comprising» (or «comprises (comprise)») comprises the terms «consisting», «consisting», as well as the terms «consisting essentially» and «essentially consisting».

In order to facilitate the reading of the application, the description has been separated into various paragraphs and sections. These separations should not be considered to disconnect the substance of a paragraph or section from that of another paragraph or section. On the contrary, the description encompasses all possible combinations of the different paragraphs, sections and sentences it contains.

The content of the bibliographic references cited in the application is specifically incorporated by reference into the content of the application.

The following examples are given for illustrative purposes only. They are in no way limiting.

EXAMPLES

Example 1

Have been Produced:

plasmid constructs encoding the Gag protein (under the control of an inducible promoter), optionally in fusion with a purification tag (6His tag) or with a detection marker (eGFP) [cf. FIG. 6A construction i.; cf. FIG. 7A], as well as plasmid constructs encoding a heterologous RNA of interest linked to a retrosomal addressing sequence (under the control of an inducible promoter), for example plasmid constructs containing (in insert) a DNA encoding an eGFP mRNA (heterologous RNA) linked (3') to a GAG DNA sequence lacking the expression promoter of the Gag protein (as a retrosomal addressing sequence) [cf: FIG. 6A construction ii.; cf. FIG. 7B], and implemented for transformation of a yeast strain lacking endogenous Ty retrotransposon (*Saccharomyces paradoxus*).

The yeast cells thus transformed produce T-retrosomes (T-bodies or pseudo-viral particles) which contain the heterologous RNA, without retro-transcribing this heterologous RNA or retro-integrating it into the genome.

The heterologous RNA thus produced were purified.

Material and Methods

1. Strains and Plasmids Used

Strains:

A strain of *Escherichia coli* DH5 bacteria is available from ATCC® under the number 67877™

A wild yeast strain *Saccharomyces paradoxus* is available from ATCC® under the number 76528™

Yeast strain YAM13 is a strain of *S. paradoxus* MATalpha Ty0 leu2 lys2 ura3.

The yeast strain YAM13 ΔSrb2 is a *S. paradoxus* YAM13 strain whose Srb2 gene has been deleted.

The YAM13 yeast strain ΔSpt21 is a *S. paradoxus* YAM13 strain, whose Spt21 gene has been deleted.

A wild yeast strain *Saccharomyces cerevisiae* is available from ATCC® under the number 52530™.

ATCC® is the American Type Culture Collection (10801 University Blvd.; Manassas, Virginia 20110-2209; USA.).

*S. paradoxus* is naturally devoid of retrotransposon, in particular Ty1 retrotransposon, unlike *S. cerevisiae* which is naturally provided with Ty1 retrotransposon.

Construction encoding the Gag protein (cf. FIG. 7A):

For the construction encoding the Gag protein, two plasmids were used, one to amplify the GAG sequence (SEQ ID NO: 1) and the other to express the Gag protein with and without a poly-histidine tag (tag 6-His).

The DNA, RNA and protein sequences of the 6-His tag are the sequences of SEQ ID NO: 4, 5 and 6, respectively.

The first plasmid (pBDG1 130Apo 1) contains the GAG sequence and served as a template for the amplification and addition of the 6-His tag upstream and/or downstream (SEQ ID NO: 7, SEQ ID NO: 9 and SEQ ID NO: 11) of this sequence by PCR.

The second plasmid pAG425GAL-ccdB was used to express Gag proteins with or without 6-His tag in the N-terminal and/or C-terminal position in yeast (*S. paradoxus* YAM13 ΔSrb2). The proteins were inducibly expressed by the presence of the galactose GAL1 promoter. This plasmid consists of an origin of bacteria and eukaryotic replication (2μ-20-50 copies per cell) which allows the amplification of the plasmid in *E. coli* DH5 bacteria and an expression of the proteins in the yeast. In order to specifically select the cells transfected with the plasmid, different selection markers were used. For the *E. coli* bacteria, the ampicillin resistance gene allowed for the selection of transfected bacteria and the ccdB gene was used to induce the death of transfected bacteria that did not recombine between the sequence of interest and the plasmid. For the yeast strain, the leucine synthesis gene (LEU2) allowed the selection of yeasts transformed by the plasmid.

The YAM13 yeast ΔSrb2 is auxotrophic for this amino acid and the transformation with the plasmid allows the yeast to grow on a medium lacking leucine (−LEU).

The expression medium of the proteins of interest by the yeasts was thus made on a medium −LEU and containing 2% of galactose.

A similar plasmid construct was produced to express the Gag protein (SEQ ID NO: 3 in fusion with the eGFP protein within the plasmid pAG426-ccdB-eGFP (cf. FIG. 7A). The plasmid pAG426-ccdB-eGFP has the uracil synthesis gene (URA3) which allows the selection of yeasts transformed by the plasmid. The YAM13 yeast ΔSrb2 is auxotrophic for this amino acid and the transformation with the plasmid allows the yeast to grow on a medium lacking in uracil (−URA).

The DNA, RNA and protein sequences of eGFP are the sequences of SEQ ID NO: 25, 26 and 27, respectively.

Construction encoding the heterologous RNA having the Gag addressing sequence (cf. FIG. 7B; cf. construction ii) of FIG. 6A):

An mRNA encoding eGFP (Enhanced Green Fluorescent Protein) has been implemented as heterologous RNA.

Luciferase encoding mRNA has been implemented as heterologous RNA and the luciferase DNA, RNA and protein sequences are the sequences of SEQ ID NOs: 28, 29 and 30, respectively.

The Gag addressing sequence is a retrosomal addressing RNA sequence (RNA sequence which addresses the heterologous RNA to which it is linked, to the retrosomes which are otherwise formed by the Gag protein). The retrosomal addressing sequence is a non-coding Gag sequence (Gag coding sequence which has been modified by deletion of the Gag expression promoter, non-coding Gag sequence which can also be designated as «mini-GAG» or «MiniGag» or «EndGAG»).

The DNA and RNA sequences of the Gag addressing sequence are the sequences of SEQ ID NO: 13 and 14, respectively.

The DNA encoding the heterologous mRNA and the DNA encoding the Gag addressing sequence were inserted into a plasmid (plasmid pAG425-GAL-ccdB).

2. Cloning of the episomal plasmid encoding GAG protein 2.1. GAG sequence with and without Tag 6-His 2.1.1. Amplification of the GAG sequence for the addition of Tag 6-His by PCR The strategy adopted for cloning is a strategy based on the ligation between two nucleotide sequences having cohesive ends obtained by enzymatic digestion.

Expression of the Gag protein with the 6-His tag facilitates purification on a nickel column. The coding GAG sequence (SEQ ID NO: 1) was amplified so as to have, upstream and/or downstream, a sequence allowing the expression of the 6-His tag (SEQ ID NO: 7, SEQ ID NO: 9 and SEQ ID NO: 11). Restriction sites for SpeI and HindIII were added from both sides, and the sequences were cloned into plasmid pAG425GAL-ccdB. PCR (Polymerase Chain Reaction) was used to amplify the GAG sequence and allow the addition of the restriction sites and the sequence encoding the 6-His tag. The PCR was performed using the KAPA HIFI HOTSTART READYMIX PCR kit (KAPABIOSYSTEMS) according to the supplier's recommendations, using different primer pairs:

- amplification of the GAG coding sequence with 6-His tag upstream of SEQ ID NO: 7 (called 6His-GAG): sense primer FQ3 of SEQ ID NO: 19 and antisense primer RQ3 of SEQ ID NO: 20;
- amplification of the GAG coding sequence with 6-His tag downstream of SEQ ID NO: 9 (called GAG-6His): sense primer FQ4 of SEQ ID NO: 21 and antisense primer RQ4 of SEQ ID NO: 22;
- amplification of the GAG coding sequence with 6-His tag upstream and downstream of SEQ ID NO: 11 (called 6His-GAG-6His): sense primer FQ3 of SEQ ID NO: 19 and antisense primer RQ4 of SEQ ID NO: 22.

Primers RQ3 and FQ4 were used to amplify GAG and add restriction sites to the extremities. The PCR reaction was carried out with final concentrations of 0.3 μM primers, 1× KAPA HIFI HOTSTART READYMIX PCR™ and 200 ng/μL of DNA. Dimethylsulfoxide (DMSO), at a final concentration of 5%, was added for the amplification reactions with the FQ4/RQ4 and FQ3/RQ4 primer pairs to avoid the secondary structures that can be taken up by the primers. The template DNA used is the plasmid pBDG1 130 containing the GAG sequence to be amplified.

The denaturation was carried out at 95° C. for 30 min, followed by 30 cycles of 20 sec at 98° C. and then 15 sec at 65° C. (pair of primers FQ3/RQ3) or at 60° C. (pairs of primers FQ4/RQ4, FQ3/RQ4 and FQ4/RQ3), and 1 min at 72° C. Terminal elongation was done at 72° C. for 3 min. At the end of the amplification reaction, 8 of PCR product were added with 2×5× loading buffer. The mixture obtained was deposited on a 0.6%+5% ethidium bromide (BET) agarose gel and the migration is then carried out for 1 hour at 80 V. The size marker used is 1 KB DNA LADDER™ (NEW ENGLAND BIOLABS). After migration, a revelation under UV allowed to verify that there was specific amplification.

Specific PCR products were extracted with CLEAN-UP PCR Kit, GEL EXTRACTION™ (MACHEREY-NAGEL) according to the supplier's recommendations. The extracted fragments are quantified with NANODROP and then digested with HindIII and SpeI to be ligated with the expression plasmid pAG425GAL-ccdB.

2.1.2. ligation

Enzymatic digestion with HindIII and SpeI of the episomal expression plasmid pAG425GAL-ccdB and inserts (GAG with C-terminal 6-His tag (SEQ ID NO: 7), GAG with N-terminal 6-His tag (SEQ ID NO: 9), GAG with C-terminal and N-terminal 6-His tag (SEQ ID NO: 11) made it possible to linearize the plasmid and form cohesive protruding ends between the plasmid and the various inserts. The digestion by the two restriction enzymes was made in one reaction under the following conditions: 1 μg of DNA (insert or plasmid), 5 U/mL of each of the two enzymes HindIII and SpeI, IX Buffer CUTSMART™ 10× for a reaction volume of 40 μL. The digestion was carried out for 1 h30 at 37° C. After digestion, the reaction mixture is deposited on 0.6% agarose gel in order to verify that there has been digestion and a gel extraction of the fragment of interest was made with the CLEAN-UP GEL EXTRACTION™ PCR kit. (MACHEREY-NAGEL) according to the supplier's recommendations.

After quantification of the extracts, the ligation was made according to a molar ratio of pDNA/insert of 1: 3. The reaction was carried out at 25° C. for 5 min (Quick ligation kit NEB). After obtaining the different recombinant plasmids, an amplification by *E. coli* DH5α was carried out of plasmids constructed pAG425GAL-GAG, pAG425GAL-6His-GAG pAG425GAL-GAG-6His, pAG425GAL-6His-GAG-6His.

2.2 GAG-eGFP Merge Sequence 2.2.1. Amplification of the GAG sequence for fusion with eGFP The coding GAG sequence (SEQ ID NO: 1) was amplified by PCR without the stop codon (TGA) so as to allow fusion with eGFP. The amplification primers make it possible to have the restriction sites Spel and EcoRI upstream and downstream of the amplified sequence. The PCR was performed using the KAPA HIFI HOTSTART READYMIX PCR™ kit (KAPABIOSYSTEMS) according to the supplier's recommendations, using the primer pair:

- amplification of the coding sequence GAG without stop codon (TGA): forward primer FQ5 of SEQ ID NO: 31 and antisense primer RQ5 of SEQ ID NO: 32.

The PCR reaction was carried out with final concentrations of 0.3 μM primers, 1× KAPA HIFI HOTSTART READYMIX PCR™ and 200 ng/μL of DNA. Dimethylsulfoxide (DMSO), at a final concentration of 5%, was added for the amplification reactions with the FQ5/RQ5 primer pairs. The template DNA used is the plasmid pBDG1130 containing the GAG sequence to be amplified.

At the end of the amplification reaction, 8 μL of PCR product were added 2 μL of 5× loading buffer. The mixture obtained was deposited on a 0.6%+5% ethidium bromide (BET) agarose gel and the migration is then carried out for 1 hour at 80 V. The size marker used is 1 KB DNA LADDER™ (NEW ENGLAND BIOLABS). After migration, a revelation under UV allowed to verify that there was specific amplification.

Specific PCR products were extracted with CLEAN-UP PCR Kit, GEL EXTRACTION™ (MACHEREY-NAGEL) according to the supplier's recommendations. The extracted fragments are quantified with NANODROP and then digested with SpeI and EcoRI to be ligated with the expression plasmid pAG426GAL-ccdB-eGFP.

2.2.2. Digestion and ligation

The enzymatic digestion with SpeI and EcoRI of the pAG426GAL-ccdB-eGFP expression plasmid and the insert (GAG without stop codon (SEQ ID NO: 37) made it possible to linearize the plasmid and form cohesive protruding ends between the plasmid and the insert. The digestion by the two restriction enzymes was made in one reaction under the following conditions: 1 μg of DNA (insert or plasmid), 5 U/mL of each of the two enzymes HindIII and Spe1, IX Buffer NEB 2.1 IX for a reaction volume of 40 μL. The digestion was carried out for 1 h30 at 37° C. After digestion, the reaction mixture is deposited on 0.6% agarose gel in order to verify that there has been digestion and a gel extraction of the fragment of interest was made with the CLEAN-UP GEL EXTRACTION™ PCR kit. (MACHEREY-NAGEL) according to the supplier's recommendations. After quantification of the extracts, the ligation was made according to a molar ratio of pDNA/insert of 1: 3. The reaction was carried out at 25° C. for 5 min (Quick ligation kit NEB).

After obtaining the different recombinant plasmids, an *E. coli* DH5a amplification was carried out of the plasmid construct pAG426GAL-GAGeGFP.

2.3 GAG-eGFP-6-His sequence with and without 3MS2

2.3.1. Synthesis and digestion of the GAG-eGFP-6-His-3MS2 sequence

The «GAG-eGFP-6HIS-3MS2» cassette is ordered (SEQ ID NO: 38) and synthesized by GenScript and inserted into the plasmid pUC57 (pUC57-GeGHM). This sequence codes for the Gag-eGFP fusion protein with a C-terminal histidine tag with 3' of this sequence three MS2 repeats (SEQ ID NO: 35).

Plasmid pUC57-GAG-eGFP-6HIS (pUC57-GeGH) is cloned by removing the sequence 3MS2 (SEQ ID NO: 35) by NotI digestion followed by ligation at 25° C. for 5 min (Quick ligation kit NEB).

Plasmids pUC57-GeGHM and pUC57-GeGH are digested with the restriction enzymes Spe1 and KpnI. The fragment corresponding to the sequence GAG-eGFP-6HIS-3MS2 (SEQ ID NO: 38) (2369 bp) and GAG-eGFP-6HIS (SEQ ID NO: 39) (2101 bp) are purified after deposition on gel 0.6% agarose to verify digestion and gel extraction of the fragment of interest was made with CLEAN-UP GEL EXTRACTION™ PCR Kit (MACHEREY-NAGEL) according to the supplier's recommendations.

2.3.2. Ligation

Spel and KpnI enzymatic digestion of the pAG426GAL-ccdB-eGFP expression plasmid and GAG inserts without a stop codon (SEQ ID NO: 37) made it possible to linearize the plasmid and form cohesive protruding ends between the plasmid and the inserts. GAG-eGFP-6HIS-3MS2 (SEQ ID NO: 38) and GAG-eGFP-6HIS (SEQ ID NO: 39). After digestion, the reaction mixture is deposited on 0.6% agarose gel in order to verify that there has been digestion and a gel extraction of the fragment of interest was made with the CLEAN-UP GEL EXTRACTION PCR™ kit. (MACHEREY-NAGEL) according to the supplier's recommendations. After quantification of the extracts, the ligation was made according to a molar ratio of pDNA/insert of 1: 3. The reaction was carried out at 25° C. for 5 min (Quick ligation kit NEB). After obtaining the different recombinant plasmids, amplification with *E. coli* DH5a was carried out.

After quantification of the extracts, the ligation was made according to a molar ratio of pDNA/insert of 1: 3. The reaction was carried out at 25° C. for 5 min (Quick ligation kit NEB). After obtaining the various recombinant plasmids, an amplification by *E. coli* DH5α was carried out of the plasmids constructed pAG426GAL-GeGHM and pAG426GAL-GeGH.

3. Cloning of the Integrative Plasmid Encoding the GAG Protein 3.1. Amplification of the GAL-GAG-eGFP sequence by PCR The GAL-GAG-eGFP sequence encoding the Galactose promoter Gag-eGFP fusion protein (SEQ ID NO: 42) was amplified by PCR. The amplification primers make it possible to have the SacI and KpnI restriction sites upstream and downstream of the amplified sequence.

The PCR was performed using the KAPA HIFI HOT-START READYMIX PCR™ kit (KAPABIOSYSTEMS) according to the supplier's recommendations, using the primer pair:

- amplification of the GAG-eGFP coding sequence: sense primer FQ5 of SEQ ID NO: 31 and antisense primer RQ5 of SEQ ID NO: 32.

At the end of the amplification reaction, 8 μL of PCR product were added 2 of 5× loading buffer. The mixture obtained was deposited on a 0.6%+5% ethidium bromide (BET) agarose gel and the migration is then carried out for 1 hour at 80 V. The size marker used is 1 KB DNA LADDER™ (NEW ENGLAND BIOLABS). After migration, a revelation under UV allowed to verify that there was specific amplification.

3.2. ligation

The integrative yeast plasmid pRS306 has a URA3 marker and a Ampiciline AmpR resistance gene.

The pRS306 expression plasmid underwent enzymatic digestion with SacI and KpnI.

The digestion by the two restriction enzymes was made in one reaction under the following conditions: 1 μg of DNA (insert or plasmid), 5 U/mL of each of the two enzymes Sac1 and KpnI, IX of Buffer NEB 1.1 IX for a reaction volume of 40 μL. The digestion was carried out for 1 h30 at 37° C. After digestion, the reaction mixture is deposited on 0.6% agarose gel in order to verify that there has been digestion and carry out a gel extraction of the fragment of interest was made with the PCR kit CLEAN-UP GEL EXTRACTION™ (MACHEREY-NAGEL) according to the supplier's recommendations. The ligation is carried out using the Gibson Assembly kit under the following conditions: Gibson Master Mix+50 ng of pRS306 vector digested with SacI/KpnI (427 lpb)+0.5 pM, ie 926 ng of GAL-GAG-EGFP PCR+Qsp H20 10 μL. The reaction is incubated at 50° C. After obtaining the different recombinant plasmids, amplification with *E. coli* DH5a was carried out.

4. Cloning of the plasmid encoding heterologous RNA

An mRNA encoding eGFP (Enhanced Green Fluorescent Protein) has been implemented as heterologous RNA. The DNA, RNA and protein sequences of eGFP are the sequences of SEQ ID NO: 25, 26 and 27, respectively.

An mRNA encoding luciferase has been implemented as heterologous RNA. The DNA, RNA and protein sequences of luciferase are the sequences of SEQ ID NO: 28, 29 and 30, respectively 4.1 Luciferase sequence as heterologous RNA 4.1.1. EndGAG Sequence as Addressing Sequence The «Luc-EndGAG-3M52» cassette is ordered (SEQ ID NO: 43) and synthesized by GenScript and inserted into the plasmid pUC57 (pUC57-LEGM). This sequence encodes for the 3 luciferase protein of this sequence the addressing sequence in the EndGAG T-bodies followed by three MS2 repeats (SEQ ID NO: 35).

Plasmid pUC57-Luc-EndGAG (pUC57-LEG) is cloned by removing the sequence 3MS2 (SEQ ID NO: 35) by NotI digestion followed by ligation at 25° C. for 5 min (Quick ligation kit NEB).

Plasmids pUC57-LEGM and pUC57-LEG are digested with the restriction enzymes Spe1 and HindIII. The fragment corresponding to the sequence Luc-EndGAG-3MS2 (SEQ ID NO: 43) (3425 bp) and Luc-EndGAG (SEQ ID NO: 44) (3039 bp) are purified after depositing on a 0.6% agarose gel in order to verify that digestion and gel extraction of the fragment of interest were made with the CLEAN-UP GEL EXTRACTION PCR™ Kit (MACHEREY-NAGEL) according to the supplier's recommendations. Enzymatic digestion with SpeI and KpnI of the pAG425GAL-ccdB expression plasmid and the Luc-EndGAG-3MS2 (SEQ ID NO: 43) and Luc-EndGAG (SEQ ID NO: 44) inserts made it possible to linearize the plasmid and form cohesive protruding ends between the plasmid and the inserts. After digestion, the reaction mixture is deposited on a 0.6% agarose gel in order to verify that there has been digestion and a gel extraction of the fragment of interest was made with the CLEAN-UP GEL EXTRACTION™ PCR kit. (MACHEREY-NAGEL) according to the supplier's recommendations.

After quantification of the extracts, the ligation was made according to a molar ratio of pDNA/insert of 1: 3. The reaction was carried out at 25° C. for 5 min (Quick ligation kit NEB). After obtaining the different recombinant plasmids, an amplification by *E. coli* DH5a was carried out of the plasmids constructed pAG425GAL-LEGM and pAG425GAL-LEG.

4.1.2 GAGm sequence as a addressing sequence

The sequence «GAGm» is controlled (SEQ ID NO: 13) and synthesized by GenScript and inserted into the plasmid pUC57 (pUC57-Gm). This sequence is the addressing sequence in complete and mutated T-bodies (SEQ ID NO: 14).

The plasmid pAG425GAL-LEGM is digested with the restriction enzyme NdeI and then partially with the restriction enzyme NotI. The fragments corresponding to the plasmid released from the EndGAG sequence (9850 bp) and to the plasmid released from the sequence EndGAG and 3MS2 (9464 bp) are purified after deposition on 0.6% agarose gel in order to verify that there has been digestion and a gel extraction of the fragment of interest was made with the CLEAN-UP GEL EXTRACTION™ PCR kit (MACHEREY-NAGEL) according to the supplier's recommendations.

The plasmid pUC57-GAGm is digested with the restriction enzymes NdeI and NotI. The fragment corresponding to GAGm (1336 bp) is purified after deposition on 0.6% agarose gel and a gel extraction of the fragment of interest was made with CLEAN-UP GEL EXTRACTION™ PCR kit (MACHEREY-NAGEL) according to the supplier's recommendations.

After quantification of the extracts, the ligation was made according to a molar ratio of pDNA/insert of 1: 3. The reaction was carried out at 25° C. for 5 min (Quick ligation kit NEB). After obtaining the various recombinant plasmids, an amplification by *E. coli* DH5a was carried out of plasmids constructed pAG425GAL-LGmM and pAG425GAL-LGm.

4.2 Sequence eGFP as heterologous RNA

The eGFP sequence is amplified by PCR from plasmid pCMV-eGFP. The amplification primers make it possible to have the Spel and Alel restriction sites upstream and downstream of the amplified sequence. PCR was performed using the KAPA HIFI HOTSTART READYMIX PCR kit (KAPA-BIOSYSTEMS) according to the supplier's recommendations, using the primer pair. At the end of the amplification reaction, 8 μL of PCR product were added 2 of 5× loading buffer. The mixture obtained was deposited on a 0.6%+5% ethidium bromide (BET) agarose gel and the migration is then carried out for 1 hour at 80 V. The size marker used is 1 KB DNA LADDER™ (NEW ENGLAND BIOLABS). After migration, a revelation under UV allowed to verify that there was specific amplification.

Plasmids pAG425GAL-LGmM, pAG425GAL-LGm, pAG425 GAL-LEGM and pAG425GAL-LEG are digested with restriction enzymes SpeI and AleI. The fragments corresponding to the plasmids released from luciferase are purified after deposition on 0.6% agarose gel and a gel extraction of the fragment of interest was made with the CLEANUP GEL EXTRACTION™ (MACHEREY-NAGEL) PCR kit according to supplier's recommendations.

After quantification of the extracts, the ligation was made according to a molar ratio of pDNA/insert of 1: 3. The reaction was carried out at 25° C. for 5 min (Quick ligation kit NEB). After obtaining the different recombinant plasmids, amplification by *E. coli* DH5α was carried out using plasmids constructed pAG425GAL-eGFPGmM, pAG425GAL-eGFPGm, pAG425GAL-eGFPEGM and pAG425 GAL-eGFPEG.

5. Amplification of recombinant plasmids by *E. coli* DH5α

The transformation of *E. coli* DH5a bacteria was done by adding 5 μL of the ligation product for 50 μL of competent *E. coli* DH5a bacteria.

A 30 min incubation on ice was made before inducing 30s heat shock at 42° C. The samples were then incubated on ice for 5 minutes before putting them at 37° C. for 50 min in 300 of SOC medium. Transformant bacteria were plated on LB+100 μg/mL ampicillin plates.

After culture of the transformants, several clones were transplanted and taken up in liquid medium in order to extract the recombinant plasmids. The extraction was done using the PLAS MID DNA PURIFICATION™ kit (MACHEREY-NAGEL) according to the supplier's recommendations. After purification, enzymatic digestion with HpaI (NEW ENGLAND BIOLABS) is carried out. This digestion was carried out under the same conditions as those by HindIII/SpeI (NEW ENGLAND BIOLABS). For the recombinant plasmids, two restriction sites were observed while for the non-recombinant plasmids a single restriction site was observed. Three profiles could be found: linearized plasmid not digested with HindIII/SpeI (9249 bp), linearized plasmid digested with HindIII/SpeI (7495 bp) and recombinant linearized plasmid (6752 bp+2036 bp). Sequencing was done for the recombinant plasmids.

6. Yeast transformation 6.1. Transformation with episomal plasmid

The different episomal recombinant plasmids obtained were used to transform the yeasts *S. paradoxus* and *S. cerevisae* (cf. FIGS. 7A and 7B).

The yeasts are washed with water and then with 0.1 M lithium acetate (LiOAc). The pellet was resuspended in 240 μL, 50% PEG, 36 μL of 1 M LiOAc+8 μL of plasmid DNA+5 μL of denatured salmon DNA. The resulting mixture was stirred for 1 min and then incubated for at least 30 min at 25° C. Heat shock was induced at 42° C. or 37° C. for 20 min. The cells are washed and resuspended in sterile distilled water. The transformed yeasts were plated on the leucine-free selective box (in the case of the transformation of a plasmid possessing the Leu2 gene whose backbone is named pAG425) into Uracil (in the case of the transformation of a plasmid containing the URA3 gene whose backbone is named pAG426), Leucine and Uracil (in the case of the transformation of two plasmids, one having the URA3 gene whose backbone is named pAG426 and the other having the Leu2 gene whose backbone is named pAG425).

Examples of *S. paradoxus* strains illustrating this transformation with episomal plasmid have been deposited with the CNCM under the Budapest Treaty, see Table 1 below.

6.2. Transformation with integrative plasmid

The plasmid pRS306-GAL-GAG-EGFP is linearized by digestion with AatII FastDigest (Thermo Scientific) under the following conditions: 2 μL of AatII enzyme+2 μg of pRS306-GAL-GAG-EGFP pRNA+5 μL of Green FastDigest buffer+50 $H_20$. The reaction is incubated for 25 min at 37° C. After digestion, the reaction mixture is deposited on 0.6% agarose gel in order to verify that there has been digestion and a gel extraction of the fragment of interest was made with the CLEAN-UP GEL EXTRACTION™ PCR kit. (MACHEREY-NAGEL) according to the supplier's recommendations.

The yeasts are washed with water and then with 0.1 M lithium acetate (LiOAc). The pellet was resuspended in 240 μL, 50% PEG, 36 μL of 1 M LiOAc+8 μL of plasmid DNA+5 μL of denatured salmon DNA. The resulting mixture was stirred for 1 min and then incubated for at least 30 min at 25° C. Heat shock was induced at 42° C. or 37° C. for 20 min. The cells are washed and resuspended in sterile distilled water. The transformed yeasts were plated on the leucine Uracil-free selective dish (in the case of the transformation of a plasmid possessing the URA3 gene whose backbone is called pRS306), Leucine and Uracil (in the case of two plasmids, one with the URA3 gene whose backbone is named pRS306 and the other with the Leu2 gene whose backbone is named pAG425).

Examples of *S. paradoxus* strains illustrating this transformation with integrative plasmid have been deposited with the CNCM under the Budapest Treaty, see Table 1 below.

TABLE 1

| Identity of the strain | CNCM Number | Date of deposit |
|---|---|---|
| Strain «TB16» = *S. paradoxus* with replacing the Rpb1 gene with a mutated version (C67Y) of the Rpb1 gene of *S. cerevisae*, integration of the coding sequence for the protein of 2017 Gag-eGFP fusion (SEQ ID NO: 3 - SEQ ID NO: 27) under the influence of a galactose promoter (GAL) [Selective medium URA] | I-5171 | Feb. 24, 2017 |
| Strain «TB17»: *S. paradoxus* with replacing the Rpb1 gene with a mutated version (C70Y) of the Rpb1 gene of *S. cerevisae*, and integration of the coding sequence for the protein of 2017 Gag-eGFP fusion (SEQ ID NO: 3 - SEQ ID NO: 27) under the influence of a galactose promoter (GAL) [Selective medium URA] | I-5172 | Feb. 24, 2017 |
| «TB18» strain: *S. paradoxus* with replacing the Rpb1 gene by a mutated version (H80Y) of the Rpb1 gene of *S. cerevisae*, and integration of the coding sequence for the protein of 2017 Gag-eGFP fusion (SEQ ID NO: 3 - SEQ ID NO: 27) under the influence of a galactose promoter (GAL) [Selective medium URA] | I-5173 | Feb. 24, 2017 |
| «TB21» strain: *S. paradoxus* with deletion of the ΔSrb2 gene and with replacing the gene Rpb1 by a mutated version (H80Y) of the Rpb1 gene of *S. cerevisae*, and integration of the sequence coding for the 2017 Gag-eGFP fusion protein (SEQ ID NO: 3 - SEQ ID NO: 27) under the influence of a galactose promoter (GAL) [Selective medium URA] | I-5174 | Feb. 24, 2017 |
| «TB32» strain: *S. paradoxus* with deletion of the ΔSrb2 gene, and integration into the genome of coding sequence for the Gag-eGP-6His-3MS2 fusion protein (SEQ ID NO: 2017 3 SEQ ID NO: 27- SEQ ID NO: 6) Gag-eGFP-6His-3MS2 under the influence of a galactose promoter (GAL) [Selective medium URA] | I-5175 | Feb. 24, 2017 |
| Strain «TB53»: *S. paradoxus* with deletion of the ΔSrb2 gene; integration of the coding sequence for the Gag-eGFP fusion (SEQ ID NO: 3 - SEQ ID NO: 27) under the influence of a galactose promoter (GAL) [Selective medium URA]; and plasmid transformation allowing expression of a luciferase model RNA (SEQ ID NO: 29) having a complete addressing sequence in 3 ‘ mutagenesis (GAGm = SEQ ID NO: 14) of RNA in T-bodies under the influence of a galactose promoter (GAL) [Selective Medium LEU] | I-5293 | Mar. 15, 2018 |
| Strain «TB54»: *S. paradoxus* with deletion of the ΔSrb2 gene; integration of the coding sequence for the Gag-eGFP fusion (SEQ ID NO: 3 - SEQ ID NO: 27) under the influence of a galactose promoter (GAL) [Selective medium URA]; plasmid transformation allowing expression of a luciferase model RNA (SEQ ID NO: 29) with a partial addressing sequence (or minimal) (SEQ ID NO 18) of RNA in T-bodies under the influence of a galactose promoter (GAL) [Selective Medium LEU] | I-5294 | Mar. 15, 2018 |

7. Induction of expression and extraction of T-bodies 7.1. Galactose induction

In order to produce T-bodies and to express the Gag protein (SEQ ID NO: 3) with or without a 6-His tag (SEQ ID NO: 8, SEQ ID NO: 10 and SEQ ID NO: 12), galactose induction is performed.

The cells are centrifuged for 10 min at 3000 rpm and then rinsed twice with sterile water. The cells are then resuspended in the appropriate selective medium for transformed episomal and/or integrative plasmids devoid of glucose and supplemented with 2% galactose. The induction was carried out overnight at 25° C. Various mechanical and chemical extraction techniques have been tested to optimize the conditions for obtaining T-retrosomes (T-bodies or pseudo-viral particles).

7.2. Mechanical lysis by balls

The yeasts were centrifuged for 3 mM at 3000 rpm and then washed in cold lysis buffer (50 mM Tris pH 7.6, 50 mM NaCl, 5 mM MgCl 2, 0.1% NPA, 1 mM β-mercaptoethanol, IX PROTEASE INHIBITOR COMPLETE MINI EDTA FREE™ 0.4 U/μL RNASE INHIBITOR™). The cells are centrifuged. The pellet is taken up in cold lysis buffer supplemented with beads. The resulting mixture was vortexed on ice for 1 mM A centrifugation of 2 mM at 2000g is made and the supernatant was collected and then centrifuged for 10 mM at 10000 g. The pellet was taken up in cold lysis buffer and incubated for 30 min at room temperature. Centrifugation for 10 mM at 10,000 g is made and the pellet is taken up in cold lysis buffer.

7.3. Mechanical lysis by sonication

The yeasts were centrifuged for 10 mM at 10000 g and then resuspended in BINDING BUFFER™ IX containing 80 U/mL of lyticase to obtain spheroplasts. The suspension was incubated for 10 mM at 25° C. Following this incubation, the yeasts were lysed by sonication on ice at a rate of 10×15 sec at 70% with 15 sec of cooling between each sonication. Centrifugation for 15 mM at 5000 g was done to collect inclusion bodies and cell debris.

7.4. Chemical lysis in sodium hydroxide

The yeasts were centrifuged and resuspended in a volume-to-volume mixture of H2O and 0.2M NaOH. The resulting mixture was incubated at room temperature for 5 mM and then centrifuged for 2 mM at 14000 rpm. The pellet obtained was taken up in LAEMMLI™ 2× to be denatured for 15 mM at 95° C. After denaturation, a 2 mM centrifugation at 8000 rpm was done and the supernatant was recovered in a new tube to be stored at 4° C.

7.5. Y-PERTM chemical lysis

Y-PERTM YEAST PROTEIN EXTRACTION REAGENT™ Kit (THERMO SCIENTIFIC) was used as recommended by the supplier.

7.6. Mechanical lysis by high pressure homogenization

Yeasts are lysed by high pressure homogenization 3 passages at 2000 bar in lysis buffer (50 mM Tris pH 7.6, 50 mM NaCl, 5 mM MgCl2, 0.1% NP-40, 1 mM β-mercaptoefhanol, 1× complete inhibitor protease mini EDTA free, 0.4 μL RNase inhibitor) (V/V).

8. Protein dosage

The determination of the protein extracts was carried out by the BCA method (INTERCHIM).

9. Western SDS-PAGE Transfer

The extracted proteins were separated on SDS-PAGE gel in 1× migration buffer. The separation gel used contained 12% acrylamide.

The migration was made during 1h at 180V. The size marker, PRECISION PLUS PROTEIN™ KALEIDOSCOPE™ (BIO-RAD), was deposited at 10 μL/well After migration, the proteins were transferred to a polyvinylidene fluoride (PVDF) membrane by semi-dry transfer. The PVDF membrane was previously activated with methanol before mounting the transfer. The assembly was done as follows, WHATMANN papers moistened in IX transfer buffer, PVDF membrane, 12% acrylamide separation gel and WHATMANN papers moistened in IX transfer buffer. The transfer was made at 2.5 A; 25 V for 7 mM. The membrane was recovered and then washed twice for 10 min with TBS +0.1% TWEEN (TBST). Saturation was done for 1 hour in 0.1% TBST+3-5% milk. After saturation, three 15 mM washes were made in 0.1% TBST and then the primary antibodies were added for overnight incubation at 4° C. Mouse anti-Ty1 primary antibodies and anti-6-His rabbit antibodies were diluted 1/2000 in 0.1% TBST+3% milk. After incubation with the primary antibodies, the membrane was washed three times for 15 mM at 0.1% TBST and the secondary antibodies were added for incubation at room temperature with shaking. The anti-mouse IgG secondary antibodies (HRP) and the anti-rabbit IgG antibody (HRP) were diluted to 1/20 000 in 0.1% TBST+3% milk. After incubation with the secondary antibodies, the membranes were washed 3 times 15 min in 0.1% TBST. The membranes are then revealed by the CLARITY WESTERN ECL BLOTTING SUBSTRATE™ (BIO-RAD). A volume-to-volume (1:1) blend of CLARITY WESTERN PEROXIDE REAGENT™ and CLARITY WESTERN LUMINOL/ENHANCER™ was made and applied to the membranes. The reading was done at PIXI™ or by photographic film.

10. Immunofluorescence analysis with a confocal microscope

In order to verify that the presence of the tag 6-His (SEQ ID NO: 5) does not interfere with the formation of T retrosomes (T-bodies), a marking of these T-bodies was made using the couple anti-Ty1/FITC antibodies.

Before labeling, the induction of the expression of the different proteins was made overnight at 25° C. in –UEU +2% galactose.

The yeasts were then fixed with 4% formaldehyde for 1 h at 25° C. The cells were recovered after centrifugation for 3 min at 2000 rpm and washed three times in 0.1 M $KHPO_4$ solution; pH 6.5 and once in a 1.2M solution of sorbitol; 0.1M $KHPO_4$; pH 6.5. The pellet was resuspended in a solution of 1.2M sorbitol; 0.1M $KHPO_4$; pH 6.5, then the pellet was added volume to volume in a solution composed of 1.2M sorbitol; 0.1M $KHPO_4$; pH 6.5 with 1/100 β-mercaptoethanol added. The resulting mixture was incubated for 5 min at room temperature. Lyticase was added at 50 U/mL final before incubation at 25° C. for 30 min. The spheroplasts obtained were recovered by centrifugation for 2 min at 2000 rpm. Washing was done with a 1.2M solution of sorbitol; 0.1M $KHPO_4$; pH 6.5. Cold methanol was added at equivalent volume for 6 min and then cold acetone for 30 s.

A washing with PBS supplemented with 1% BSA was done before saturating the yeasts for 5-10 min in this same solution. The saturation solution was removed and the anti-Ty1 mouse primary antibody diluted 1/1000 in PBS was contacted with the yeast overnight at 4° C. The following day, the yeasts were washed 5 times with PBS+1% BSA. The fluorescein-coupled anti-mouse IgG secondary antibody (FITC) diluted 1/2000 in PBS+1% BSA was incubated for 2 h at room temperature in the dark. After incubation, 5 washes in PBS+1% BSA and one wash with a 1.2M solution of sorbitol; 0.1M $KHPO_4$; pH 6.5 were made. The yeasts were resuspended in the latter solution before being deposited between slides and lamellae.

11. Fluorescence analysis by flow cytometry

To determine which extraction technique makes it possible to recover the most Gag positive cells (SEQ ID NO: 3), a pair of antibodies coupled to fluorescence was used and then the fluorescence was analyzed by flow cytometry.

Per 100 protein extracts, 400 PBS supplemented with 10% fetal calf serum (FCS) and 0.1% RNAsin (PROMEGA) were added.

The whole was incubated at 4° C. for 30 min. The mouse anti-Ty1 primary antibody diluted 1/100 was incubated for 1 h at 4° C. The anti-mouse IgG secondary antibody Cy5 diluted 1/200 was added and incubated for 30 min at 4° C. The samples were analyzed by flow cytometry.

12. Purification by nickel affinity chromatography

Purification was done using the HIS BIND™ RESIN CHROMATOGRAPHY kit (NOVAGEN).

Purification was based on the immobilization of bivalent nickel ions ($Ni^{+2}$) on a nitrilotriacetic acid (NTA) matrix. The 6-His tag (SEQ ID NO: 6) added in fusion of the Gag protein (SEQ ID NO: 3) consists of several imidazole nuclei which are electron donors that interact strongly with $Ni^{+2}$ ions immobilized on the matrix. The Gag protein in fusion with a 6-His tag in Nter and/or Cter (SEQ ID NO: 8, SEQ ID NO: 10 and SEQ ID NO: 12) is retained on the nickel column. After retention of the protein on the column, a high concentration of imidazole was added to play the role of competitor for the interaction with the Ni 2+. This competition induced an elution of the Gag protein in fusion with a 6-His tag in Nter and/or Cter. The purification was done by the HIS BIND™ RESIN CHROMATOGRAPHY kit (NOVAGEN), according to the supplier's recommendations, by two distinct methods:

- a batch method for low protein concentrations, with the aim of developing the optimal elution condition: this method consists in carrying out the purification in a micro-tube containing the matrix;
- a column chromatography method, with a greater concentration of proteins: the column is connected to a peristaltic pump and a UVICORDSII™ spectrophotometer (AMERSHAM) which makes it possible to obtain a signal when a protein is detected.

13. RNA extraction

After protein purification, RNA extraction was performed to quantify the proportion of Gag-specific RNA.

For a minimum volume of 200 μL of purified T-bodies, a volume of phenol acid/chloroform was added. The mixture obtained was vortexed for 1 min and then centrifuged for 5 min at 14,000 rpm. The supernatant was recovered and a volume of chloroform added. The mixture obtained was vortexed for 1 min and then centrifuged for 5 min at 14,000 rpm. The supernatant was recovered and 1/10 volume 3 M sodium acetate pH 5.2 and 2.5 volumes (supernatant+sodium acetate) of 100% ethanol. The resulting mixture was incubated at −20° C. overnight. The next day, the resulting mixture was centrifuged for 15 min at 14000 rpm at 4° C. The dried pellet was resuspended in nuclease-free water (Nuclease Free Water). The extracted RNAs were quantified with NANODROP™

14. qRT-PCR

Extracted RNAs were reverse transcribed (reverse transcription; RT) for the production of complementary DNA (cDNA) by the REVERTAID RT REVERSE TRANSCRIPTION™ kit (THERMOFISHER SCIENTIFIC), according to the supplier's recommendations, using 500 ng of RNA by reaction with the random hexamer primer (random hexamer primer) of the kit.

The cDNAs obtained are quantified with NANODROP™. QPCR is performed using the QUANTIFFAST SYBR GREEN PCR™ Kit (QUIAGEN), as recommended by the supplier. The standard range was made using plasmid pBDG1130 of λg<1 μL at 0.1 μg/μL. The primers used: qGAGF (SEQ ID NO: 23) and qGAGR (SEQ ID NO: 24) allowed the amplification of 277 bp of GAG. The program used for the amplification was as follows: first a preincubation at 50° C. for 2 min, then a denaturation at 95° C. for 10 min, followed by cycles at 95° C. for 15s, at 60° C. for 30s, at 72° C. for 30s. A melting curve was produced at the end of the experiment to check the absence of contaminants: at 95° C. for 15 s then at 50° C. for 1 min and at 95° C. with acquisitions every 5° C.

Results

Selection and modification of yeast strains (for robust mRNA production in T-bodies)

Figure 1A:
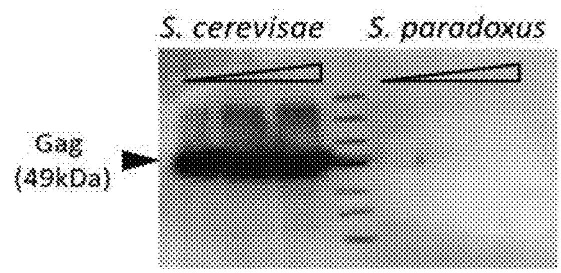
FIG. 1A illustrates the expression of Gag protein (Ty1) in yeasts *Saccharomyces cerevisae* and *Saccharomyces paradoxus*. Gag protein expression analysis was performed by Western anti-Gag transfer (49 kDa) on cell lysate samples. Unlike *S. cerevisiae, S. paradoxus* lacks Ty1 retrotransposon.

The analysis of the expression of the Gag protein (49 kDa, SEQ ID NO: 3) on cell lysate samples of *S. cerevisiae* and *S. paradoxus* yeast confirms that the *S. paradoxus* strain is devoid of the retrotransposition element. Ty1 (cf. FIG. 1A).

Figure 1B:
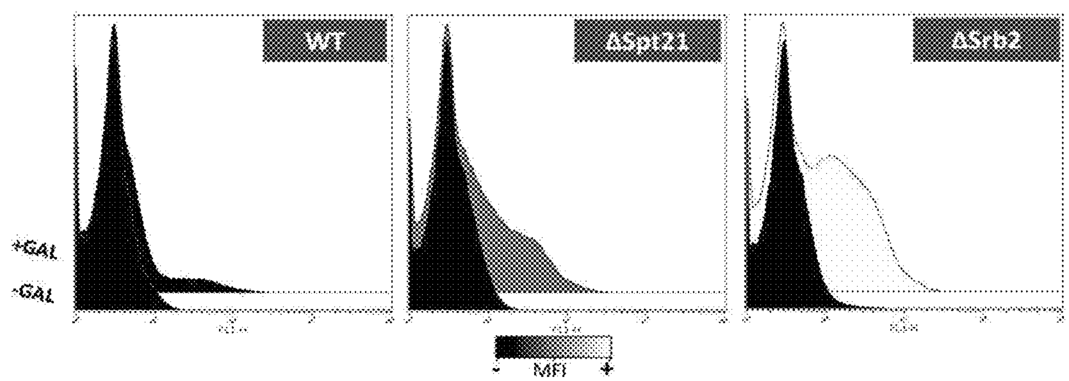
FIG. 1B illustrates the flow cytometric measurement of eGFP expression in wild *S. paradoxus* yeast (WT), and the ΔSpt21 and ΔSrb2 transcriptional mutants. After transformation of the yeasts with a plasmid encoding eGFP under the control of a galactose inducible promoter, the transcriptional mutants allow a significant increase in the number of eGFP positive cells as well as the intensity of the fluorescence (quantity per cell, T-bodies (pseudo-viral particles) whose Gag protein is labeled by eGFP).

Transformation of yeast *S. paradoxus* with a plasmid encoding eGFP under the control of a galactose-inducible promoter shows that the ΔSpt21 and/or ΔSrb2 transcriptional mutations allow a significant increase in the number of eGFP positive cells as well as in the intensity of fluorescence. The results are illustrated in FIG. 1B.

Construction of expression vectors for T-bodies formation and EGFP mRNA addressing in T-bodies The confocal fluorescence microscopy analyzes of the expression of the eGFP and the Gag-eGFP fusion protein in the *S. paradoxus* yeast and the ΔSpt21 and ΔSrb2 transcriptional mutants were carried out. The results are illustrated by FIGS. 2A and 2B. An increase in the number of T-bodies positive cells (FIG. 2A) as well as an increase in the number of T-bodies per cell in the ΔSpt21 and ΔSrb2 transcriptional mutants are observed (FIG. 2B). Flow cytometric analysis of the expression of T-bodies eGFP (Gag-eGFP fusion protein) in the transcriptional mutant of the yeast *S. paradoxus* ΔSrb2 after an 8-hour treatment with tunicamycin (TUNI) was carried out (Tunicamycin is an antibiotic produced by bacteria of the genus *Streptomyces* that have an action on N-glycosylation and on the cell cycle). The results are illustrated in FIG. 2C. An 8-hour treatment with tunicamycin causes an increase in the number of T-bodies (11% YS 48%).

Fluorescence in situ hybridization experiments (fluorescence in situ hybridization, FISH) were performed to locate the model mRNAs encoding the eGFP protein by using primers addressing Cy5-labeled eGFP mRNA on yeast *S. paradoxus* ΔSrb2 transformed with a Gag-eGFP fusion plasmid or with a MiniGag-eGFP fusion plasmid. The results are illustrated by FIGS. 3A and 3B.

Perfect collocation between the Gag protein and the corresponding mRNA is observed (FIG. 3A). A study was conducted to look for deleted Gag nucleotide sequence that allows addressing of mRNAs in T-bodies. This sequence is called MiniGag in FIG. 3B.

Purification of T-bodies

The protocol for extracting T-bodies from yeast *S. paradoxus* expressing the Gag-eGFP fusion protein after galactose induction is based on a mechanical yeast lysis followed by differential centrifugations.

Figures 4A, 4B:
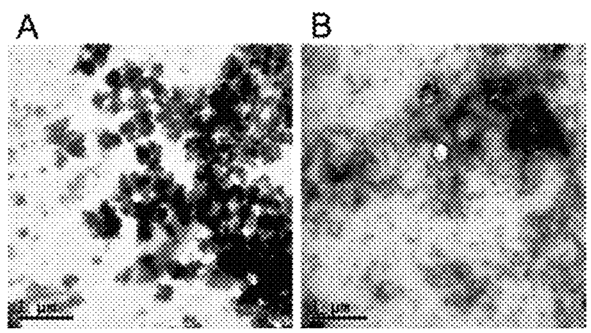

Two different mechanical extraction techniques (ball lysis and sonication method) were tested. The results are illustrated by FIGS. 4A (glass beads) and 4B (sonication). After extraction with the aid of glass beads (FIG. 4A), the T-bodies appear as spherical-shaped particles with a diameter of 200 nm. On the other hand, the method of sonication lysis induces a destruction of T-bodies with debris observable by electron microscopy (FIG. 4B). The method of lysis by the beads seems to be the best suited to get the most integrity T-bodies.

The purification of the T-bodies was carried out on a nickel column by virtue of the presence of the 6-histidine motif (6His tag). Three constructs were made, where the Gag protein has a 6His tag:

in N-terminal (6His-GAG), in C-terminal (GAG-6His), in N and C-terminal (6His-GAG-6His).

These constructs were transformed into the mutant ΔSrb2 of the yeast *S. paradoxus*. The formation of T-bodies was observed by immunofluorescence (FIG. 5A). Expression of the Gag protein was verified by Western blotting (FIG. 5B). The purification was carried out on a nickel column by competition with imidazol. The results are shown in FIG. 5C (elution of T-bodies at 800 mM imidazole for GAG-6His construction).

Example 2

*Saccharomyces* yeasts of species other than *paradoxus* (in this case, *S. cerevisiae* yeasts), and yeasts of other genus than *Saccharomyces* (in this case, yeasts of the *Pichia* genus) were transformed by the plasmid constructs described. in example 1 above, namely by:

- a plasmid construct encoding the Gag protein (under the control of an inducible promoter), possibly in fusion with a purification tag (6His tag) or with a detection marker (eGFP) [cf. FIG. 6A construction i.; cf. FIG. 7A], and by
- a plasmid construct encoding a heterologous RNA of interest linked to a retrosomal addressing sequence (under the control of an inducible promoter), for example a plasmid construct containing (in insert) a DNA encoding an eGFP mRNA (for heterologous RNA) linked (3') to a GAG DNA sequence lacking the expression promoter of the Gag protein (as a retrosomal addressing sequence) [cf. FIG. 6A construction ii.; cf. FIG. 7B].

Yeasts thus transformed produce retrosomes containing the heterologous RNA, without retro-transcribing this RNA or retro-integrating it.

Samples of some of these yeasts were deposited with the CNCN under the Budapest Treaty.

TABLE 2

| Identity of the strain | CNCM Number | Date of deposit |
|---|---|---|
| Strain «TBScl»: *S. cerevisiae* strain, virgin of Ty element (TyO), and transformed by a plasmid episomal for the expression of a protein GAG (Tyl) fusion (SEQ ID NO: 3) and eGFP in 2017 the influence of a galactose promoter (SEQ ID NO: 27) (GAL) [Selective Medium URA] | I-5176 | Feb. 24, 2017 |

CNCM is the National Collection of Culture of Microorganisms (Institut Pasteur, 28 rue du Dr Roux, 75724 Paris Cedex 15, France).

Example 3: Transfection (and Expression) of RNA Extracted from T-bodies (Virus-Like Particles) in Mammalian Dendritic Cells RNAs were produced as described in Example 1 and were transfected (liposomally) into mammalian cells, in this case dendritic cells.

RNA transfection experiments were performed in mouse dendritic cells (DC2.4 line, available from THERMOFISHER SCIENTIFIC).

The eGFP mRNAs that were produced in yeast *S. paradoxus* were transfected ΔSrb2 (cf. example 1 above) transformed by:

- a construct responsible for forming the T-bodies structure (plasmid encoding the Gag protein of SEQ ID NO: 3; FIG. 6A (i)), and
- a construct for the transcription of an eGFP RNA having a miniGAG sequence («EndGAG», SEQ ID NO: 14) 3' which addresses this eGFP RNA within T-bodies (FIG. 6A (ii)).

The eGFP mRNAs produced in the T-bodies of this yeast were extracted and purified as described in Example 1 above (extraction of the T-bodies mechanically-balls, then purification of the eGFP mRNAs contained in these T-bodies), then vectorized on cationic liposomes (liposomes 100 or Lip100). Liposomes 100 are composed equally of a cationic lipid (lipid 1), and a neutral colipid pH sensitive (lipid 2). Lipid 1 is a cationic lipid of permanent charge carried by an N-methylimidazolium group, for the complexation of nucleic acids. Lipid 2 has protonable acidic pH which promotes endosomal escape after destabilization of the membrane in acidic medium. In these lipids it is not a quaternary ammonium but a phosphorus atom which is the link between the carbon chains and the imidazole nucleus. These lipids are lipophosphoramidates whose structure is inspired by those of lipid membranes which are less toxic both in vitro and in vivo.

Liposomes 100 have in particular been described in Perche et al. 2010, Perche et al. 2011, Mevel et al. 2008a, and Mevel et al. 2008b.

Mouse dendritic cells were incubated for 20 hours with these liposomes, or with RNA synthetically produced in vitro as a control. The results are illustrated in FIG. 6B. RNA synthetically produced in vitro as a control gives a very low transfection rate of 0 to 1.5%, with a dose of 100 ng mRNA eGFP in vitro (FIG. 6B, left cytogram). On the other hand, after transfection with the liposomes containing T-bodies RNA, 32.77% of the cells express the fluorescent protein (FIG. 6B, right cytogram).

These results illustrate that the ARs produced by the yeast T-bodies of the application can be transfected into a mammalian cell, more particularly into a dendritic cell, and that the protein that these mRNAs encode can be correctly translated into this cell. host cell. These results support the medical, and in particular vaccine, applications of the RNAs produced by these T-bodies (RNA vaccination).

Example 4: Mass Spectrometry Study of Transcriptional Changes Present on RNAs Extracted from T-bodies (Virus-Like Particles)

A mass spectrometric study of the chemical modifications present at the biotech model model luciferase messenger RNA as described in Example 1 was carried out after «pull out» of the luciferase mRNA as follows.

A first hybridization step is carried out between 10 μg RNA extracted complexes, granules, pseudo-viral particles and 1 μM of biotinylated single-stranded DNA oligonucleotide, complementary to the bioproduct RNA luciferase sequence (SEQ ID NO: 45 5'-TCCATCTTCCAGCGGATAGAATGGCGCCGGGCCTTTCTT-TATGTTTTTGGCGTC TTCCATAAA 3') in 5× SSC buffer (750 mM sodium chloride and 75 mM trisodium citrate (adjusted to pH 7.0 with HCl) in a final volume of 100 μL. The reaction volume is incubated for 3 min at 90° C., then 10 mM at 65° C. The hybridization reaction is then stored at room temperature. In parallel, MyOneT1 Dynabeads magnetic beads grafted with streptavidin are washed. 100 μL of beads are collected by pipetting and vortexed at half speed. To separate the beads from the supernatant the beads are centrifuged briefly, then placed on a magnetic medium for 2 mM, the supernatant is removed gently (still tube on the magnetic medium).

The beads are resuspended in an equal volume of B & W IX buffer (5 mM Tris-HCl (pH 7.5) 0.5 mM EDTA 1 M NaCl). This step is repeated 3 times. A last wash is carried out in 5×SSC buffer. The hybridization reaction is placed in the presence of vortex-blended beads at half speed and stirred (600 rpm) for 30 min at 25° C. The beads are washed once in 50 of 1×SSC buffer and 3 times in 25 μL of 0.1×SSC. The supernatant is removed and the beads are resuspended in MilliQ water. The beads are heated at 75° C. for 3 min. The beads are centrifuged briefly, then placed on a magnetic support for 2 mM, the supernatant is collected (still on the magnetic medium) and transferred to a new tube. During the elution step, part of the immobilized oligonucleotide is cleaved from the beads, it can be removed by digestion with DNasel (RNase-free, 3.5 μg/μL final) for 2 hours at 37° C. The sample can be stored at −20° C. The volume of the sample is reduced to 180 μL with MiliQ water, 18 μl, 3 M sodium acetate solution and 2 μL of glycogen (10 mg/mL) are added and vortexed. 600 μL of 100% ethanol are added.

The reaction is vortexed and incubated at −20° C. for at least 1 hour. The reaction is then centrifuged at 10,000 g for 30 min at 4° C. The pellet is rinsed twice with 200 μL of 70% ethanol and then dried at ambient temperature for 5 minutes. The pellet is then taken up in MiliQ water.

A mass spectrometry study of the chemical modifications present at the level of the RNA messenger bioproduced was carried out on this sample. This technique is based on a mass spectrometric analysis (LC-MS) of the fragments obtained after complete hydrolysis by R ase T1 of the RNA studied. 1 μg of RNA is digested into nucleosides and the internal standard (SILIS) is added.

The resulting chromatogram showing common modifications of eukaryotic RNA corresponds to FIG. 8. About twenty modifications of ribonucleosides characteristic of eukaryotes are screened by this technique (cf. FIG. 8). Many modifications are no longer detectable between the RNA before and after <<pull out» in the purified RNA (cf. FIG. 8). Some modifications are detectable after purification «pull out»:

m5U, 5-methyluridine;
m5C, 5-methylcytidine;
m1A, 1-methyladenosine;
Gm, 2'-O-methylguanosine;
M7 G, 7-methylguanosine;
Am, 2'-O-methyladenosine;
Cm, 2'-O-methylcytidine; and
m3C, 3-methylcytidine.

Example 5: Stability of Expression of RNA Extracted from T-bodies (Virus-Like Particles) in Mammalian Dendritic Cells Luciferase RNAs produced and modified in vitro (ARCA cap, PolyA64+tail or pseudouridine) were transfected into murine dendritic cells (DC2.4) in parallel with a bioproduced yeast luciferase RNA (cf. FIG. 9):

Capped RNAs are produced by in vitro transcription by T7 polymerase from linearized DNA templates. The Ambion mMessage mMachine™ ULTRA transcription kit was used according to the provider's protocol. The transcriptional mixture contains an analog of the m7G (5') ppp (5') G mRNA (anti reverse-cap analog (ARCA)) cap which is incorporated by T7 polymerase into 5' transcripts.

The PolyA64+ tail is added in vitro using the E-PAP reagent for additional polyadenylation.

Pseudouridine (N1-Methylpseudouridine-5'-Triphosphate—100 mM Trilink) is incorporated in the reaction mixture (1.5 pseudouridine for 20 reaction volume) in order to incorporate in vitro 50% pseudouridine in the composition. synthesized RNA.

The bioproduced RNAs were as described in Example 1.

50 ng of each of the RNAs was vectorized using Lipofectamine Messenger Max and luciferase activity in the transfected cells was measured in vitro. It is observed that the bioproduced RNA luciferase in yeast T-bodies (TB) is more efficient (3 logs difference) than the most effective RNA synthesized in vitro (cf. FIG. 9).

Example 6: Pre-Industrial Production of RNA Extracted from T-Bodies

Bioproduced RNAs in yeast were obtained in the pre-industrial phase via the implementation of the following protocol:

1/3 pre-cultures (PC) are carried out in YNB medium (6.7 g/L)+CSM-URA-LEU (0.79 g/L)+Glucose (20 g/L) sterilized by autoclaving at 25° C. stirring (230 rpm) as follows:

a. PCI: 5 mL at 25° C. for 24h from an isolated clone;

b. PC2: 100 mL (3.5 mL PCI+96.5 mL of medium) at 25° C. for 24h; then c. PC3: 400 mL (inoculation with D0600 nm 0.1 from PC2) at 25° C. for 24h.

2/A fermentor (5 L capacity) is inoculated at OD 0.2 (from PC3) in YNB medium (6.7 g/L)+CSM-URA-LEU (0.79 g/L)+Glucose (20 g/L). An anti-foam type EXCELLO Antifoam is added: draws 0.5% (v/v) at the end of the day. The agitation of the fermenter is set at 1000 rpm in «local» then passage to «remote» when the $pO_2$ value is 10% below the set value. The pH is maintained at 5.4 and adjusted from sterile phosphoric acid (1.2 M) and ammonia solutions.

3/In parallel, a galactose feeding is performed. The triggering of this galactose feeding is programmed on the peak $pO_2$ with the setpoint $pO_2$: 40%. The rise in $pO_2$ is dependent on the total consumption of glucose. This galactose feeding is carried out from a sterile 20% galactose solution for a final concentration of 2%. The duration of the induction is fixed at 24 hours.

4/Passed these 24 h, the culture volume is collected and centrifuged at 4000 rpm for 15 min 5/The T-bodies are extracted as described in Example 1.

6/Bioproduced RNAs in yeast are extracted from T-bodies as described in Example 1.

BIBLIOGRAPHIC REFERENCES

Mevel et al. 2008a Synthesis and transfection activity of new cationic phosphoramidate lipids: high efficiency of an imidazolium derivative. ChemBioChem 6: 1462-1471

Mevel et al. Novel Neutral Imidazole-lipophosphoramides for transfection assays. Chem Common. 3124-316.

Perche et al. 2010 Selective gene delivery in dendritic cells with mannosylated and histidylated lipopolyplexes. Journal of Drug Addressing 1-11

Perche et al. 2011 Enhancement of dendritic cells transfection in vivo and of vaccination against B 16F melanoma 10 with mannosylated hitidylated lipopolyplexes loaded with tumor antigen messenger RNA. Nanomedicine 7 (4): 445-453.

Rothstein et al. 1983 One-step gene disruption in yeast. Methods Enzymol. 101:202-211

Thomas et al. 1989 Elevated recombination in transcriptionally active DNA. Cell 56: 619-630

WO 2010/084371 in the name of MITOPROD

WO 2011/128444 in the name of EUKARYS

The invention claimed is:

1. A method for the recombinant production of messenger RNA (mRNA) or non-coding long-chain RNA (lncRNA), which comprises:

culturing yeast cells, which have been genetically modified to produce recombinant pseudo-viral particles which comprise said mRNA or lncRNA, and collecting the mRNA or lncRNA which is contained in the virus-like particles thus formed, wherein the yeast cells are cells of a yeast which is free of Ty1 retrotransposon or in which any Ty1 retrotransposon has been genetically modified to not produce a Ty1 retrosome, wherein the genetic modifications made to these yeast cells to produce said virus-like particles comprise transfection of these yeast cells by i. a nucleic acid comprising a first nucleotide sequence, and ii. a nucleic acid comprising a second nucleotide sequence, wherein:

the nucleic acid of i. and the nucleic acid of ii. are carried by the same molecule, or by two distinct or separate molecules, the first nucleotide sequence comprises a DNA sequence which encodes the expression of the Gag protein of a yeast Ty1 retrotransposon, the second nucleotide sequence comprises a DNA sequence having no reading frame, the first codon of which would be the ATG codon, whose RNA transcript contains two parts:

a. the sequence of said mRNA or lncRNA linked to b. the gag addressing sequence comprising the sequence of SEQ ID NO: 16, the nucleic acid of ii. does not comprise a DNA sequence whose RNA transcript would be the complete RNA sequence of said Gag protein of a yeast Ty1 retrotransposon, the Gag protein of a yeast Ty retrotransposon in both nucleic acids is the same Gag protein of a yeast Ty1 retrotransposon, and the nucleic acid of i. and the nucleic acid of ii. do not comprise a sequence encoding the reverse transcriptase of a yeast Ty1 retrotransposon, the nucleic acid of i. and the nucleic acid of ii. thereby encoding the formation, in said yeast cells, of virus-like particles which are formed by the Gag protein translated from the first nucleotide sequence, and which encapsulate said mRNA or lncRNA transcribed from the second nucleotide sequence.

2. The method of claim 1, wherein the yeast is a yeast of the genus *Saccharomyces* or *Pichia*.

3. The method of claim 1, wherein the yeast is a yeast of which one or more of the Rpb1, Spt21, Srb2 and Srb5 genes have been mutated by one or more mutations that comprise one or more mutations selected from:

replacing one or more codons each with another codon or with another nucleotide triplet, and deleting one or more nucleotides, and which stimulate or increase the production of pseudo-viral particles.

4. The method of claim 1, wherein the mRNA or lncRNA comprises at least 150 nucleotides and is heterologous to said yeast, and wherein the mRNA or lncRNA optionally encodes:

a bacteria protein or a polypeptide,
a genomic editing enzyme,
a virus protein or polypeptide,
a human transcription factor,
a human growth factor,
a human CFTR protein,
an antibody or antibody fragment, or
a polypeptide comprising at least one epitope of antigens.

5. The method of claim 1, performed In vitro using a kit comprising at least one nucleic acid comprising a first nucleotide sequence and at least one nucleic acid comprising a second nucleotide sequence, wherein:

the first nucleotide sequence comprises a DNA sequence which encodes the expression of the Gag protein of a yeast Ty1 retrotransposon, the second nucleotide sequence comprises a DNA sequence which comprises the gag addressing sequence comprising the sequence of SEQ ID NO: 16, the DNA sequence of this second nucleotide sequence that does not comprise a reading frame whose first codon would be the ATG codon, the nucleic acid that comprises the second nucleotide sequence does not comprise a DNA sequence whose RNA transcript would be the complete RNA sequence of said retrotransposon Gag protein Ty1 of yeast, and the nucleic acid which comprises the first nucleotide sequence and the nucleic acid which comprises the second nucleotide sequence are carried by the same molecule, or are carried by two distinct or separate molecules, said kit comprising no reverse transcriptase of yeast Ty1 retrotransposon, nor nucleic acid encoding such a reverse transcriptase, nor nucleic acid comprising a sequence encoding such a reverse transcriptase, and said kit may further optionally comprise cells of a yeast which is devoid of Ty1 retrotransposon, or that has been genetically modified to not produce a Ty1 retrosome, wherein the method is performed for the production of mRNA or lncRNA with a polyA tail at the 3' end and/or a 7-methylguanosine cap at the 5' end.

6. A method for producing a pharmaceutical composition which comprises at least one mRNA or lncRNA, said method comprising producing mRNA or lncRNA by the method of claim 1, and placing the mRNA or lncRNA in a pharmaceutically acceptable vehicle for producing a pharmaceutical composition, this pharmaceutical composition being optionally intended for:

the prevention or the treatment of a microbiological infection,
the prevention or the treatment of a tumor proliferation,
the prevention or the treatment of a chronic disease,
a regenerative tissue or cell therapy, or
a gene therapy.

7. The method of claim 2, wherein the yeast is a yeast of which one or more of the Rpb1, Spt21, Srb2 and Srb5 genes have been mutated by one or more mutations that comprise one or more mutations selected from:

replacing one or more codons each with another codon or with another nucleotide triplet, and deleting one or more nucleotides, and which stimulate or increase the production of pseudo-viral particles.

8. The method of claim 2, wherein the mRNA or lncRNA comprises at least 150 nucleotides and is heterologous to said yeast, and wherein the mRNA or lncRNA optionally encodes:

a bacteria protein or a polypeptide,
a genomic editing enzyme,
a virus protein or polypeptide,
a human transcription factor,
a human growth factor,
a human CFTR protein,
an antibody or antibody fragment, or
a polypeptide comprising at least one epitope of antigens.

9. The method of claim 3, wherein the mRNA or lncRNA comprises at least 150 nucleotides and is heterologous to said yeast, and wherein the mRNA or lncRNA optionally encodes:

a bacteria protein or a polypeptide,
a genomic editing enzyme,
a virus protein or polypeptide,
a human transcription factor,
a human growth factor,
a human CFTR protein,
an antibody or antibody fragment, or
a polypeptide comprising at least one epitope of antigens.

* * * * *